(12) United States Patent
Heller et al.

(10) Patent No.: US 9,907,500 B2
(45) Date of Patent: *Mar. 6, 2018

(54) LYOTROPIC LIQUID CRYSTAL COATED ANALYTE MONITORING DEVICE AND METHODS OF USE

(71) Applicants: Abbott Diabetes Care Inc., Alameda, CA (US); Board of Regents of The University of Texas System, Austin, TX (US)

(72) Inventors: Adam Heller, Austin, TX (US); Pawel Rowinski, Piaseczno (PL); Benjamin J. Feldman, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 14/873,633

(22) Filed: Oct. 2, 2015

(65) Prior Publication Data

US 2016/0058351 A1   Mar. 3, 2016

Related U.S. Application Data

(63) Continuation of application No. 14/193,983, filed on Feb. 28, 2014, now Pat. No. 9,149,218, which is a
(Continued)

(51) Int. Cl.
*A61B 5/1486* (2006.01)
*C12Q 1/00* (2006.01)
(Continued)

(52) U.S. Cl.
CPC ........ *A61B 5/14865* (2013.01); *A61B 5/1468* (2013.01); *A61B 5/14532* (2013.01); *C12Q 1/006* (2013.01); *Y10T 29/49117* (2015.01)

(58) Field of Classification Search
CPC ............ A61B 5/14532; A61B 5/14865; C12Q 1/005; G01N 27/3272; Y10S 435/817
See application file for complete search history.

(56) References Cited

U.S. PATENT DOCUMENTS 4,008,717 A   2/1977   Kowarski et al.
5,262,305 A   11/1993  Heller et al.
(Continued)

OTHER PUBLICATIONS

Tsujimura et al. "Novel FAD-Depedent glucose Dehydrogenase for a Dioxygen-Insensitive Glucose Biosensor" Biosci. Biotechnol. Biochem. 70 (3) 654-659, Mar. 2006.*
(Continued)

*Primary Examiner* — Patricia Mallari
*Assistant Examiner* — Michael Catina
(74) *Attorney, Agent, or Firm* — Vorys, Sater, Seymour and Pease LLP

(57) ABSTRACT

The present invention is directed to membranes composed liquid crystals having continuous aqueous channels, such as a lyotropic liquid crystal, including a cubic phase lyotropic liquid crystal, and to electrochemical sensors equipped with such membranes. The membranes are useful in limiting the diffusion of an analyte to a working electrode in an electrochemical sensor so that the sensor does not saturate and/or remains linearly responsive over a large range of analyte concentrations. Electrochemical sensors equipped with membranes of the present invention demonstrate considerable sensitivity and stability, and a large signal-to-noise ratio, in a variety of conditions.

14 Claims, 36 Drawing Sheets

Related U.S. Application Data continuation of application No. 13/568,799, filed on Aug. 7, 2012, now Pat. No. 8,666,470, which is a continuation of application No. 11/948,915, filed on Nov. 30, 2007, now Pat. No. 8,255,034.

(60) Provisional application No. 60/872,243, filed on Nov. 30, 2006.

(51) Int. Cl.
*A61B 5/1468* (2006.01)
*A61B 5/145* (2006.01)

(56) References Cited

U.S. PATENT DOCUMENTS

| | | | |
|---|---|---|---|
| 5,264,104 | A | 11/1993 | Gregg et al. |
| 5,320,725 | A | 6/1994 | Gregg et al. |
| 5,356,786 | A | 10/1994 | Heller et al. |
| 5,593,852 | A * | 1/1997 | Heller .............. C12Q 1/006 435/14 |
| 5,665,222 | A | 9/1997 | Heller et al. |
| 5,972,199 | A | 10/1999 | Heller et al. |
| 6,103,033 | A | 8/2000 | Say et al. |
| 6,120,676 | A | 9/2000 | Heller et al. |
| 6,134,461 | A | 10/2000 | Say et al. |
| 6,143,164 | A | 11/2000 | Heller et al. |
| 6,175,752 | B1 | 1/2001 | Say et al. |
| 6,338,790 | B1 | 1/2002 | Feldman et al. |
| 6,746,582 | B2 | 6/2004 | Heller et al. |
| 2003/0187338 | A1* | 10/2003 | Say .............. A61M 5/1723 600/345 |
| 2006/0141446 | A1 | 6/2006 | Murphy et al. |
| 2006/0178500 | A1* | 8/2006 | Kikuchi .............. C08J 5/2231 528/425 |

OTHER PUBLICATIONS

Hato et al. "Aqueous Phase Behavior of a 1-O-Phytanyl-β-d-xyloside/Water System. Glycolipid-Based Bicontinuous Cubic Phases of Crystallographic Space Groups Pn3m and Ia3d" *Langmuir*, 2004, 20 (26), pp. 11366-11373, Nov. 2004.*

Dong et al. "Bulk and Dispersed Aqueous Phase Behavior of Phytantriol: Effect of Vitamin E Acetate and F127 Polymer on Liquid Crystal Nanostructure" *Langmuir*, 2006, 22 (23), pp. 9512-9518, Oct. 2006.*

Drummond et al. "Surfactant self-assembly objects as novel drug delivery vehicles" *Current Opinion in Colloid & Interface Science* 4 449-456, 2000.*

Tan et al. "Preperation of PVA/chitosan lipase membrane reactor and its application in synthesis of monoglyceride" Journal of Molecular Catalysis B: Enzymatic vol. 18, Issues 4-6, Oct. 23, 2002, pp. 325-331.*

Mezzenga et al. "Shear rheology of lyotropic liquid crystals: a case study" Langmuir. Apr. 12, 2005;21(8):3322-33.*

Bilewicz et al. (2005) "Modified electrodes based on lipidic cubic phases" *Bioelectrochemistry* 66(1-2):3-8.

Hato et al. (2004) "Aqueous Phase Behavior of a 1-O-Phytanyl-.beta.-d-xyloside/Water System. Glycolipid-Based Bicontinuous Cubic Phases of Crystallographic Space Groups Pn3m and Ia3d" *Langmuir* 20(26):11366-11373.

Dong et al. (2006) "Bulk and Dispersed Aqueous Phase Behavior of Phytantriol: Effect of Vitamin E Acetate and F127 Polymer on Liquid Crystal Nanostructure" *Langmuir* 22(23):9512-9518.

Drummond et al. (2000) "Surfactant self-assembly objects as novel drug delivery vehicles" *Current Opinion in Colloid & Interface Science* 4:449-456.

Tan et al. (2002) "Preparation of PVA/chitosan lipase membrane reactor and its application in synthesis of monoglyceride" *Journal of Molecular Catalysis B: Enzymatic* 18(4-6): 325-331.

Tsujimura et al. (2006) "Novel FAD-Depedent glucose Dehydrogenase for a Dioxygen-Insensitive Glucose Biosensor" *Biosci. Biotechnol. Biochem.* 70(3):654-659.

Zhou et al. (2005) "Supported Lyotropic Liquid-Crystal Polymer Membranes: Promising Materials for Molecular-Size-Selective Aqueous Nanofiltration" *Adv. Mater.* 17:1850-1853. doi: 10.1002/adma.200500444.

* cited by examiner

C)

1-O-β-(3,7,11,15-Tetramethylhexadecyl)-D-ribopyranoside

Vitamin E acetate

LYOTROPIC LIQUID CRYSTAL COATED ANALYTE MONITORING DEVICE AND METHODS OF USE

This invention was made with partial Government support under through Grant No. N00014-02-1-0144 awarded by the Office of Naval Research. The Government has certain rights in the invention.

BACKGROUND

Enzyme-based biosensors are devices in which an analyte-concentration-dependent biochemical reaction signal is converted into a measurable physical signal, such as an optical or electrical signal. Such biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. The detection of analytes in biological fluids, such as blood, is important in the diagnosis and the monitoring of many diseases.

Biosensors that detect analytes via electrical signals, such as current (amperometric biosensors) or charge (coulometric biosensors), are of special interest because electron transfer is involved in the biochemical reactions of many important bioanalytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, then the hydrogen peroxide is electrooxidized and correlated to the concentration of glucose in the body fluid.

Some biosensors are designed for implantation in a living animal body, such as a mammalian or a human body, merely by way of example. In an implantable amperometric biosensor, the working electrode is typically constructed of a sensing layer, which is in direct contact with the conductive material of the electrode, and a diffusion-limiting membrane layer on top of the sensing layer. The sensing layer typically consists of an enzyme, an optional enzyme stabilizer such as bovine serum albumin (BSA), and a crosslinker that crosslinks the sensing layer components. Alternatively, the sensing layer consists of an enzyme, a polymeric redox mediator, and a crosslinker that crosslinks the sensing layer components, as is the case in—"wired-enzyme" biosensors.

In an implantable amperometric glucose sensor, the membrane is often beneficial or necessary for regulating or limiting the flux of glucose to the sensing layer. By way of explanation, in a glucose sensor without a membrane, the flux of glucose to the sensing layer increases linearly with the concentration of glucose. When all of the glucose arriving at the sensing layer is consumed, the measured output signal is linearly proportional to the flux of glucose and thus to the concentration of glucose. However, when the glucose consumption is limited by the rate of one or more of the chemical or electrochemical reactions in the sensing layer, the measured output signal is no longer controlled by the flux of glucose and is no longer linearly proportional to the flux or concentration of glucose. In this case, only a fraction of the glucose arriving at the sensing layer is contributing to the current. The current no longer increases linearly with the glucose concentration but becomes saturated, meaning that it increases less and less for a given increment of glucose concentration, and eventually stops increasing with the concentration of glucose. In a glucose sensor equipped with a diffusion-limiting membrane, on the other hand, the membrane reduces the flux of glucose to the sensing layer such that the sensor does not become saturated, or becomes saturated only at much higher glucose concentrations and can therefore operate effectively resolve an increase in the concentration of glucose when the glucose concentration is high.

There are various glucose-diffusion-limiting membranes. The membranes are, however, usually made of polymers, and either their average thickness and/or the microscopic uniformity of their thickness is difficult to control and/or reproduce. As a result, the glucose fluxes through the membranes, which determine the sensitivities of the glucose sensors employing such membranes are widely scattered, indicative of lack of adequate control in the membrane-making process. Thus, there is a need for a glucose-diffusion-limiting membrane that provides adequate regulation of the flux of glucose to the sensing layer and that is mechanically strong, biocompatible, and easily and reproducibly manufactured.

In an implantable amperometric glucose or other analyte sensor, the membrane can be also beneficial or necessary for regulating or limiting the flux of an interferent to the sensing layer, the interferent affecting the signal, for example the current produced by the analyte. By affecting the signal, the interferent adds to the measurement's error. The preferred membranes reduce the flux of the interferent more than they reduce the flux of the analyte, for example of glucose.

SUMMARY

The present invention is directed to membranes composed liquid crystals having continuous aqueous channels, such as a lyotropic liquid crystal, abbreviated here as LLC, including a cubic phase LLC, and to electrochemical sensors equipped with such membranes. The membranes are useful in limiting the diffusion of an analyte to a working electrode in an electrochemical sensor so that the sensor does not saturate and/or remains linearly responsive over a large range of analyte concentrations, in the case of glucose between about 2 mM and at least about 30 mM and is easily calibrated. Electrochemical sensors equipped with membranes of the present invention demonstrate considerable sensitivity and stability, and a large signal-to-noise ratio, in a variety of conditions.

The present invention provides an electrochemical sensor having a working electrode that includes a sensing layer in contact with a conductive material of the electrode; a cubic phase lyotropic liquid crystal membrane disposed over the sensing layer, and a counter electrode in electrochemical communication with the working electrode. In some embodiments, the sensing layer of the working electrode includes a glucose-responsive enzyme. In some embodiments, the glucose-responsive enzyme is a wired enzyme. In some embodiments, the glucose-responsive enzyme is glucose-dehydrogenase. In some embodiments, the glucose-dehydrogenase is an FAD-dependent glucose dehydrogenase. In some embodiments, the glucose-dehydrogenase is glucose oxidase.

In some embodiments, the sensing layer of the working electrode includes a redox mediator. In some embodiments, the redox mediator comprises a complex selected from the group of a ruthenium-containing complex and an osmium-containing complex. In certain embodiments, the redox mediator is non-leachable with respect to the working electrode. In certain embodiments, the redox mediator is immobilized on the working electrode.

In some embodiments, at least one amphiphile of the cubic phase lyotropic liquid crystal comprises a link between its polar head and its long hydrocarbon tail other than an ester, which makes it not-hydrolyzed in the presence of a lipase. For example, in certain embodiments, the link is an ether. An exemplary amphiphile of a cubic phase lyotropic liquid crystal has the formula:

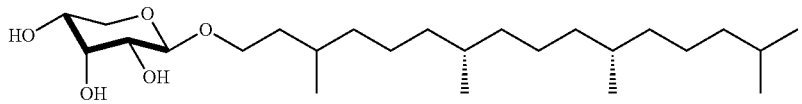

In some embodiments, the cubic phase lyotropic liquid crystal is substantially non-hydrolyzable in the presence of a lipase. In some embodiments, the cubic phase lyotropic liquid crystal membrane is adapted to limit the flux of glucose or lactate thereacross. In certain embodiments, the cubic phase lyotropic liquid crystal membrane limits flux of glucose or lactate thereacross in vivo.

The present invention also provides an electrode for use in a biosensor, including a sensing layer in contact with a conductive material of the electrode, and a cubic phase lyotropic liquid crystal membrane disposed over the sensing layer. In some embodiments, the sensing layer of the working electrode comprises a glucose-responsive enzyme. In some embodiments, the sensing layer of the working electrode includes a redox mediator. In some embodiments, the redox mediator comprises a complex selected from the group of a ruthenium-containing complex and an osmium-containing complex. In certain embodiments, the redox mediator is non-leachable with respect to the working electrode. In certain embodiments, the redox mediator is immobilized on the working electrode.

In some embodiments, at least one amphiphile of the cubic phase lyotropic liquid crystal comprises a link between its polar head and its long hydrocarbon tail other than an ester, which makes it not-hydrolyzed in the presence of a lipase. For example, in certain embodiments, the link is an ether. An exemplary amphiphile of a cubic phase lyotropic liquid crystal has the formula:

In some embodiments, the cubic phase lyotropic liquid crystal is substantially non-hydrolyzable in the presence of a lipase. In some embodiments, the cubic phase lyotropic liquid crystal membrane is adapted to limit the flux of glucose or lactate thereacross. In certain embodiments, the cubic phase lyotropic liquid crystal membrane limits flux of glucose or lactate thereacross in vivo.

The present invention also provides, an analyte sensor assembly, including an electrochemical sensor having an optionally flexible substrate comprising at least one working electrode comprising a sensing layer and a cubic phase lyotropic liquid crystal membrane disposed over the sensing layer, at least one counter electrode, and at least one contact pad coupled to each of the working and counter electrodes, the electrochemical sensor being adapted for implantation of a portion of the electrochemical sensor including the working and counter electrodes through skin; and an electrochemical sensor control unit having a housing adapted for placement on skin, a plurality of conductive contacts disposed on the housing and configured for coupling to the contact pads of the electrochemical sensor; and an RF transmitter disposed in the housing and coupled to the plurality of conductive contacts for transmitting data obtained using the electrochemical sensor. In some embodiments, only one conductive contact is required on the housing.

In some embodiments, the sensing layer of the working electrode comprises a glucose-responsive enzyme. In some embodiments, the sensing layer of the working electrode includes a redox mediator. In some embodiments, the redox mediator comprises a complex selected from the group of a ruthenium-containing complex and an osmium-containing complex. In certain embodiments, the redox mediator is non-leachable with respect to the working electrode. In certain embodiments, the redox mediator is immobilized on the working electrode.

In some embodiments, at least one amphiphile of the cubic phase lyotropic liquid crystal comprises a link between its polar head and its long hydrocarbon tail other than an ester, which makes it not-hydrolyzed in the presence of a lipase. For example, in certain embodiments, the link is an ether. An exemplary amphiphile of a cubic phase lyotropic liquid crystal has the formula:

In some embodiments, the cubic phase lyotropic liquid crystal is substantially non-hydrolyzable in the presence of a lipase. In some embodiments, the cubic phase lyotropic liquid crystal membrane is adapted to limit the flux of glucose or lactate thereacross. In certain embodiments, the cubic phase lyotropic liquid crystal membrane limits flux of glucose or lactate thereacross in vivo.

The present invention also provides a method for monitoring a level of an analyte using the analyte monitoring system by inserting the electrochemical sensor into skin of a patient, attaching the electrochemical sensor control unit to the skin of the patient, coupling a plurality of conductive contacts disposed in the sensor control unit to a plurality of contact pads disposed on the sensor, collecting data, using the sensor control unit, regarding a level of an analyte from signals generated by the sensor, transmitting the collected data to the display unit using the RF transmitter of the sensor control unit, displaying an indication of the level of the analyte on the display of the display unit. In some embodiments, only one conductive contact is required on the housing.

In some embodiments, at least one amphiphile of the cubic phase lyotropic liquid crystal comprises a link between its polar head and its long hydrocarbon tail other than an ester, which makes it not-hydrolyzed in the presence of a lipase. For example, in certain embodiments, the link is an ether. An exemplary amphiphile of a cubic phase lyotropic liquid crystal has the formula:

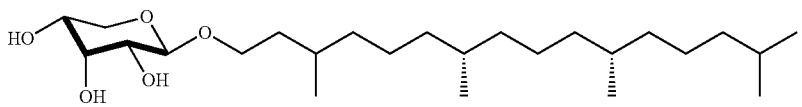

In some embodiments, the collecting data includes generating signals from the sensor and processing the signals into data. In certain embodiments, the data includes the signals from the sensor. In certain embodiments, the method further includes activating an alarm if the data indicates an alarm condition. In certain embodiments, the method further includes administering a drug in response to the data. In some embodiments, the drug is insulin.

In certain embodiments, the method further includes obtaining a calibration value from a calibration device to calibrate the data. In some embodiments, the calibration device is coupled to the display unit. In certain embodiments, the method further includes transmitting the calibration value from a transmitter in the display unit to a receiver in the sensor control unit.

The present invention also provides a method of fabricating an electrode for use in a biosensor by contacting a sensing layer in contact with a conductive material of an electrode with a cubic phase lyotropic liquid crystal membrane to dispose the cubic phase lyotropic liquid crystal membrane over the sensing layer. In some embodiments, the lyotropic liquid crystal is disposed on the sensing layer by doctor blading.

In some embodiments, the sensing layer of the working electrode comprises a glucose-responsive enzyme. In some embodiments, the sensing layer of the working electrode includes a redox mediator. In some embodiments, the redox mediator comprises a complex selected from the group of a ruthenium-containing complex and an osmium-containing complex. In certain embodiments, the redox mediator is non-leachable with respect to the working electrode. In certain embodiments, the redox mediator is immobilized on the working electrode.

In some embodiments, at least one amphiphile of the cubic phase lyotropic liquid crystal comprises a link between its polar head and its long hydrocarbon tail other than an ester, which makes it substantially not-hydrolyzed in the presence of a lipase. For example, in certain embodiments, the link is an ether. An exemplary amphiphile of a cubic phase lyotropic liquid crystal has the formula:

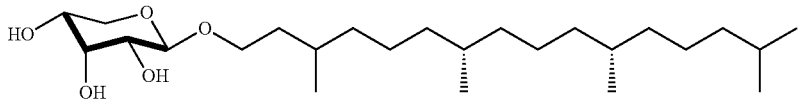

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
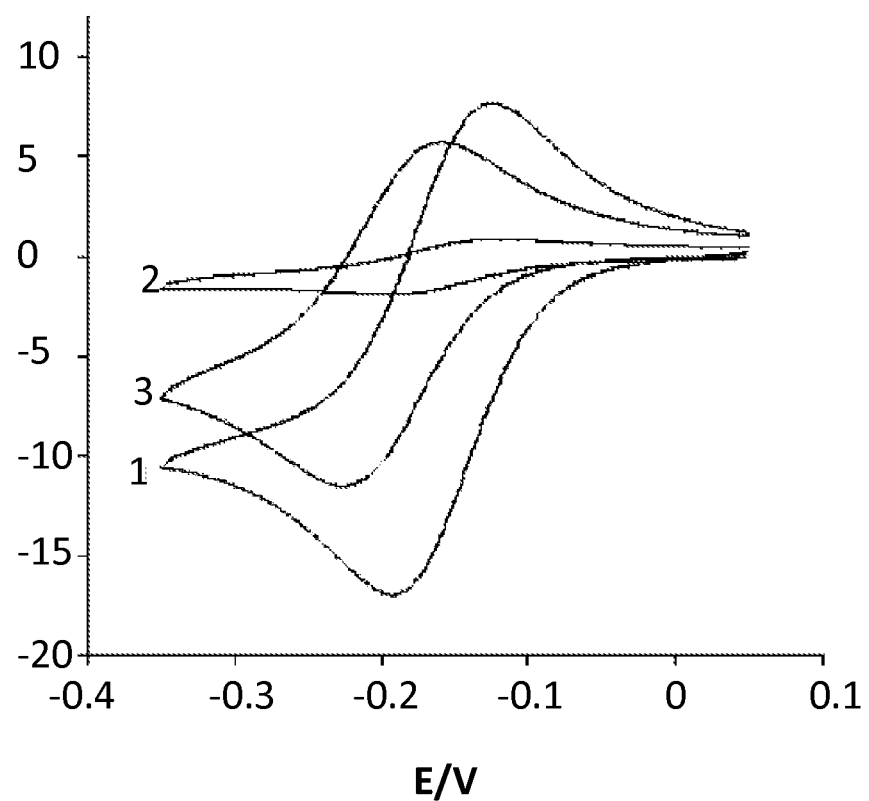
FIG. 1 shows cyclic voltammograms of 1 mM of [Ru (NH$_3$)$_6$]$^{3+}$ (Panel A); 1 mM Fe(CN)$_6$$^{3-}$ (Panel B); 0.5 mM urate (Panel C). 1 is the bare vitreous carbon electrode; 2 is the vitreous carbon electrode modified with the monoolein:water liquid crystal; 3 is the vitreous carbon electrode modified with monoolein:water:2 mol % 1,2-dioleoyl-sn-glycero-3-phosphate liquid crystal. Voltammogram 4 in panel C is of the bare electrode in buffer without an added redox active solute. 5 mm diameter, smooth, vitreous carbon electrodes; deoxygenated pH 7.3, 0.15M NaCl, 0.02 M phosphate buffer; 37.5° C.; 10 mV s$^{-1}$ scan rate; 150 μm lyotropic liquid crystal film thickness.
Figure 1:
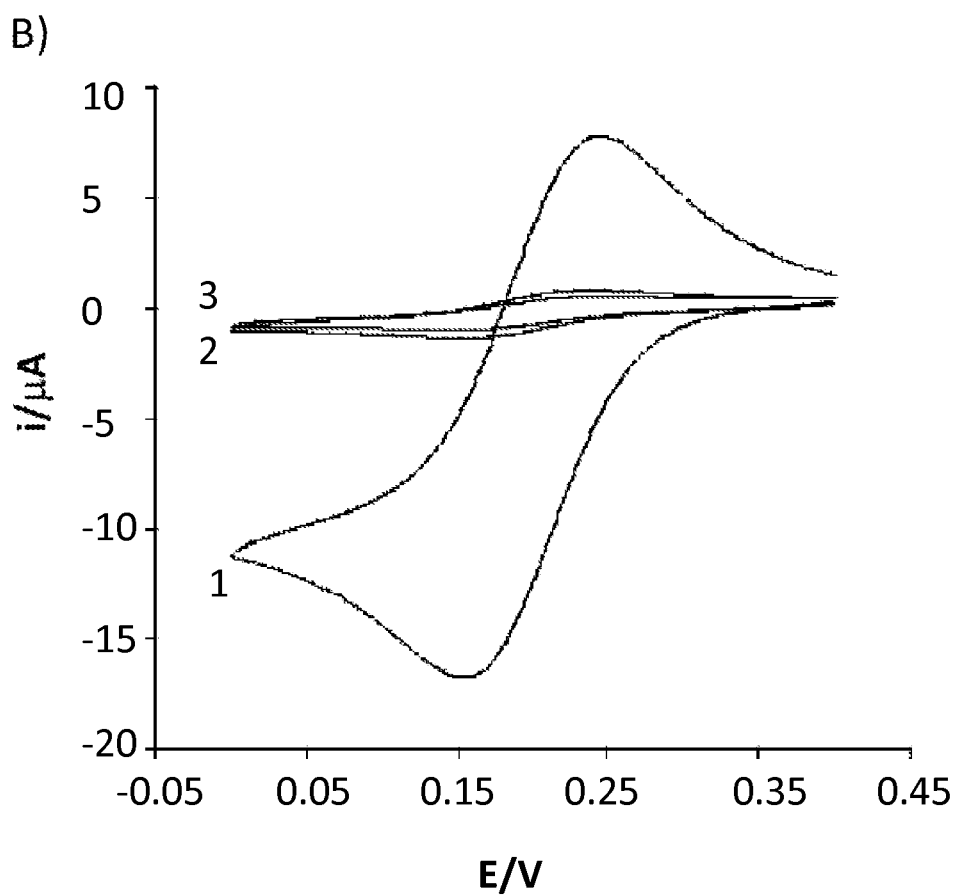
Figure 1:
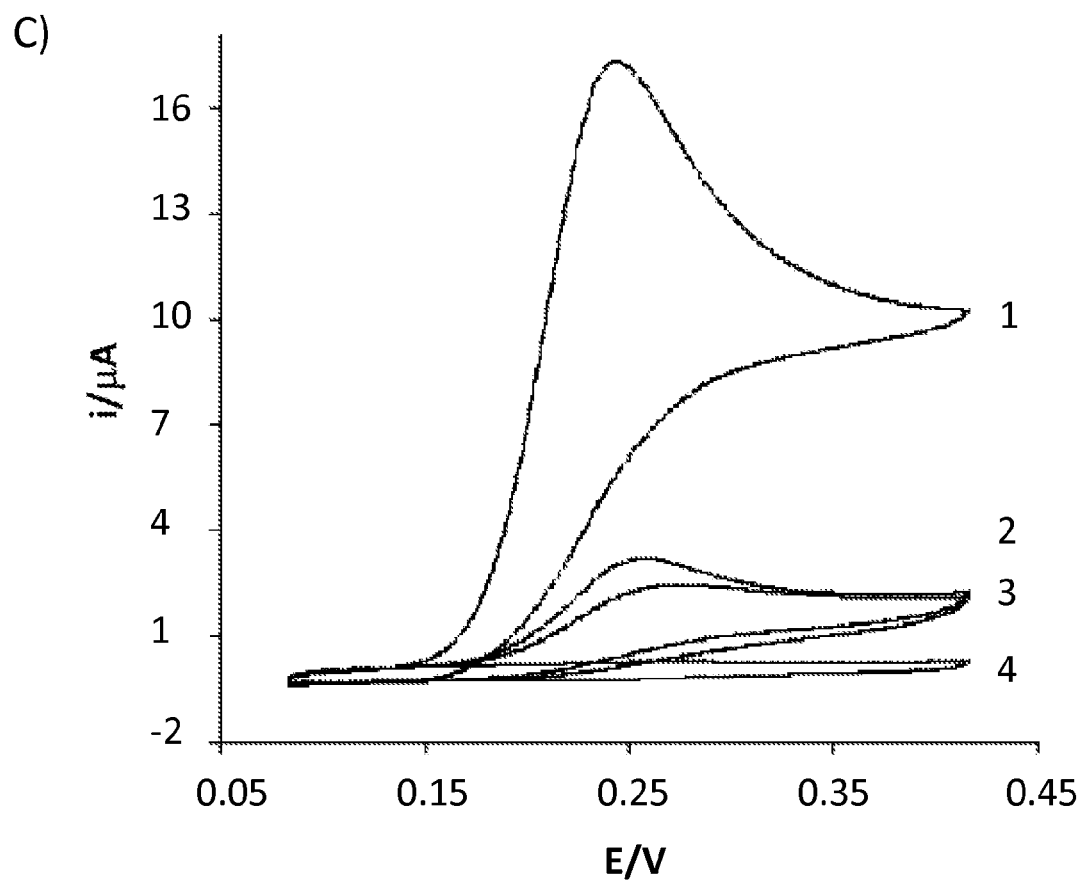

A "counter electrode" refers to an electrode paired with the working electrode, through which passes a current about equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample, via an electrochemical oxidation or reduction reaction on the sensor, or via a sequence of chemical reactions where at least one of the chemical reactions is an electrochemical oxidation or reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is chemisorbed, irreversibly adsorbed, entrapped on, or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes their loss by out-diffusion.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte, or a compound whose level depends on the level of the analyte, is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and electron conducting polymers.

A "biological fluid" or "biofluid" is any body fluid or body fluid derivative in which the analyte can be measured, for example, blood, interstitial fluid, plasma, dermal fluid, sweat, and tears.

A "redox mediator" is an electron-transfer agent for carrying electrons in one or more of the steps of the signal producing reaction or the reactions, for example between an analyte, an analyte-reduced or analyte-oxidized enzyme, and an electrode, either directly, or via one or more additional electron-transfer agents. A redox mediator that includes a polymeric backbone may also be referred to as a "redox polymer".

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

The term "wired enzyme" means an immobilized oxidoreductase comprising redox centers electrically connected to an electrode through an also immobilized redox mediator, such as a redox polymer.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention is directed to membranes composed of liquid crystals having continuous aqueous channels, such as a lyotropic liquid crystal, including a cubic phase lyotropic liquid crystal, and to electrodes and electrochemical sensors equipped with such membranes. The membranes are useful in limiting the diffusion of a water soluble analyte to a working electrode in an electrochemical sensor extending thereby the upper concentration limit at which the sensor is responsive, such as linearly responsive, to higher analyte concentrations and is easily calibrated. Electrochemical sensors equipped with membranes of the present invention demonstrate good sensitivity and stability, and a large signal-to-noise ratio, in a variety of conditions.

Diffusion Limiting Membranes

In manufacturing practice, reproduction of a deposited membrane-mass, i.e., its average thickness when dry, is feasible. However, equal-mass membranes can differ can microscopically differ in the extent of non-uniformity of distribution of their matter, making their transport characteristics difficult to reproduce. For this reason, and because of differences in their biological environments, all implanted sensors are calibrated and usually re-calibrated in-vivo. In the case of membranes that are formed by the cross-linking of soluble precursors, there are drying and curing-associated differences, even if uniformly thick precursor-films are applied by doctor-blading, as their curing is time-profile, temperature and humidity dependent. When the membranes are cast, variations in their microscopic distribution cause variations in glucose-transport. For example, two equal-mass membranes, one uniformly thick reducing ten-fold the glucose transport, the other non-uniform, comprising 50% pinholes and 50% zones of twice the average thickness, differ five-fold in their rate of glucose-permeation. When membranes are made by solvent-casting, dipping or spraying, their homogeneity depends on their history of solvent-evaporation. Solvent evaporation cools the surface of the droplet, the cooling leading to a particular temperature gradient and liquid-microcirculation pattern first, which is sensitive to variations in the air-flow and humidity of the droplet's microenvironment. Hence, films deposited from evaporating liquids are rarely of uniform thickness.

To avoid the variations in the glucose-transport characteristics of polymer-films, we disclose here uniformly thick lyotropic liquid crystal (LLC) bicontinuous cubic phase films, applied by doctor-blading. Because of their rheological properties—low viscosity mixtures are formed upon stirring the amphiphiles with water, which then set to form non-flowing phases—there is no need to crosslink. Single-phase, two-component, thermodynamically stable, LLCs are spontaneously and reproducibly-formed from amphiphiles and water. Even though organization of mixtures is entropically disfavored, the two or three-component phases are thermodynamically stable because of hydrophobic bonding of the long aliphatic chains and, in some cases, also hydrogen-bonding of polar head-groups. The bonding leads to microscopic phase-separation of the amphiphile and water, resulting in some systems in cubic-phase Ia3d, Pn3m or Im3m space group-structures with bi-continuous amphiphilic and aqueous domains. The cubic phases are clear, isotropic, non-flowing substances. In the exemplary case of monoolein/water, the water channels are of ~5 nm diameter, and the water-contacted specific-surface is massive, 500-600 $m^2g^{-1}$. The bi-continuous phases can host, for example, an agent like heparin, preventing blood clotting.

The preferred LLCs are thermodynamically stable in the presence of an excess of the physiological aqueous solution through the 20-45° C. temperature range; and they withstand drying and re-hydration without flowing, i.e. without changing shape or position.

The diffusion limiting membranes of the present invention include liquid crystals having continuous aqueous channels, such as a cubic phase lyotropic liquid crystal. In certain embodiments, the lyotropic liquid crystal includes lipids that are resistant to hydrolysis by lipases, e.g., lipids that are stable in the presence of lipases. Cubic phase LLC membranes formed of phytantriol—a liquid at ambient temperature—and water, are not hydrolyzed, but they change their shape and size in a dehydration and re-hydration cycle. Because glucose sensors are sterilized and stored in a sealed package in a dry atmosphere, it is preferred that upon drying and re-hydration not change substantially the transport characteristics.

In certain embodiments the hydrolysis resistant lipids have a covalent bond between the polar head and alkyl chain that is an ether instead of an ester. In further embodiments, the lipids have a sugar derived polar head, such as a ribose-derived head, instead of a glycerol derived head. An exemplary lipid suitable for use in the lyotropic liquid crystal membrane is 1-O-phytanyl-β-D-riboside [β-Rib(Phyt)], 1-O-phytanyl-β-D-riboside [β-Rib(Phyt)]:

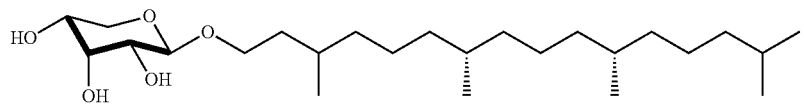

A preferred LLC was formed of water and 1-O-β-(3,7,11,15-tetramethylhexadecyl)-D-ribopyranoside containing 7 wt. % of vitamin E acetate. When this preferred LLC was applied to wired glucose oxidase bioelectrocatalyst, sensors of reproducible glucose-sensitivity were formed. At 0.1 mm thickness it reduced the glucose flux five-fold and increased the 90% response-time by less than 2 min. The membrane was mechanically rugged, withstanding the ~1 N m$^{-2}$ maximal shear stress at 5 mm diameter electrodes rotating at 4000 rpm. The activation energy for glucose permeation through this cubic phase liquid crystal was reduced to 15.6 kJ/mol, making the sensors's current less temperature-dependent than that of polymeric-membrane overcoated implantable glucose-sensors.

The resulting cubic phase lyotropic liquid crystal membrane is capable of limiting the diffusion of an analyte from one space, such as a space associated with a biofluid, to another space, such as space associated with an enzyme-containing sensing layer. An amperometric glucose sensor constructed of a wired-enzyme sensing layer and a glucose-diffusion-limiting layer of the present invention is very stable and has a large linear detection range.

The lyotropic liquid crystal can be coated over a variety of biosensors that may benefit from having a membrane disposed over the enzyme-containing sensing layer. Examples of such biosensors include, but are not limited to, glucose sensors and lactate sensors. (See U.S. Pat. No. 6,134,461 to Heller et al., which is incorporated herein in its entirety by this reference.) The coating process may comprise any commonly used technique. The preferred process is doctor blading, optionally followed by curing under ambient conditions, typically for 1 to 2 days. The particular details of the coating process may vary.

Doctor blading utilizes a tape having via holes or slots of the desired size and shape. The tape is placed on the surface to be coated. The holes or slots are filled with a mixture of comprising constituents of the liquid crystal. Using a scraping blade, known as the "doctor" the excess of the mixture is removed substances from the surface being coated, which is optionally a moving surface. The tape is then removed, leaving on the surface the shaped, uniformly thick films of the liquid crystal. The liquid crystalline films, that are optionally circular or slot-shaped, can be as thick as about 3 mm or as thin as about 5 μm.

Sensor fabrication typically includes depositing an enzyme-containing sensing layer over a working electrode and coating, preferably by doctor blading, the diffusion-limiting membrane layer over the sensing layer, and optionally, but preferably, also over the counter and reference electrodes. Sensors having other configurations such as a three-electrode design can also be prepared using similar methods.

Electrochemical Sensors

An electrochemical sensor, that includes at least one working electrode with membranes, at least one membrane comprising a liquid crystal having continuous aqueous channels, such as a cubic phase lyotropic liquid crystal disposed thereon, can be formed on a substrate. The sensor may also include at least one counter electrode (or counter/reference electrode) and/or at least one reference electrode. The counter electrode and/or reference electrode may be formed on the substrate or may be separate. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852.

The working electrode or electrodes are formed using conductive traces disposed on the substrate. The counter electrode and/or reference electrode, as well as other optional portions of the sensor, such as a temperature probe, may also be formed using conductive traces disposed on the substrate. These conductive traces may be formed over a smooth surface of the substrate, for example by patterning a metal film like gold, or within channels formed by, for example, embossing, indenting or otherwise creating a depression in the substrate and filling with a conductive paste, such as a carbon paste.

The sensing layer is often formed proximate to or on at least one of the working electrodes to facilitate the electrochemical detection of the analyte and the determination of its level in the sample fluid, particularly if the analyte can not be electrolyzed at a desired rate and/or with a desired specificity on a bare electrode. The sensing layer may include an electron transfer agent to transfer electrons directly or indirectly between the analyte and the working electrode. The sensing layer may also contain a catalyst to catalyze a reaction of the analyte. The components of the sensing layer may be in a fluid or gel that is proximate to or in contact with the working electrode. Alternatively, the components of the sensing layer may be disposed in a polymeric or sol-gel matrix that is proximate to or on the working electrode. In general, the components of the sensing layer are non-leachably disposed within the sensor. For example, the components of the sensor are immobilized within the sensor. In addition to the electrodes and the sensing layer, the sensor may also include a temperature probe, a biocompatible layer, and/or other optional components.

For example, a glucose or lactate sensor may include a first sensing layer which is spaced apart from the working electrode and contains an enzyme, for example, glucose oxidase or lactate oxidase. The reaction of glucose or lactate in the presence of the appropriate enzyme depletes oxygen and forms hydrogen peroxide. A second sensing layer is provided directly on the working electrode and contains an oxygen reduction catalyzing enzyme, such as an enzyme comprising a tri-nuclear copper center exemplified by bilirubin oxidase and an electron transfer agent to generate a signal at the electrode in response to oxygen, or a peroxidase enzyme and an electron transfer agent to generate a signal at the electrode in response to the hydrogen peroxide. The level of oxygen or hydrogen peroxide indicated by the sensor then correlates to the level of glucose or lactate. Another sensor which operates similarly can be made using a single sensing layer with both the glucose or lactate oxidase and the peroxidase being deposited in the single sensing layer. Examples of such peroxidase sensors are described in U.S. Pat. No. 5,593,852, U.S. patent application Ser. No. 08/540,789, and PCT Patent Application No. US98/02403.

In some embodiments, one or more of the working electrodes do not have a corresponding sensing layer, or have a sensing layer which does not contain one or more components (e.g., an electron transfer agent or catalyst) needed to electrolyze the analyte. The signal generated at this working electrode typically arises from interferents and other sources, such as electrooxidizable or electroreducible ions, in the fluid, and not in response to the analyte (because the analyte is not electrooxidized or electroreduced). Thus, the signal at this working electrode adds to a background signal. The background signal can be subtracted from the analyte signal obtained from other working electrodes that are associated with fully-functional sensing layers.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. One advantage of an implantable sensor having a rigid substrate is that the sensor may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the patient during operation of the sensor. However, the barb is typically small enough so that little damage is caused to the subcutaneous tissue when the sensor is removed for replacement.

At least one conductive trace is formed on the substrate for use in constructing a working electrode. In addition, other conductive traces may be formed on the substrate for use as electrodes (e.g., additional working electrodes, as well as counter, counter/reference, and/or reference electrodes) and other components, such as a temperature probe. The conductive traces may extend most of the distance along a length of the sensor, although this is not necessary. The placement of the conductive traces may depend on the particular configuration of the analyte monitoring system (e.g., the placement of control unit contacts and/or the sample chamber in relation to the sensor). For implantable sensors, particularly subcutaneously implantable sensors, the conductive traces typically extend close to the tip of the sensor to minimize the amount of the sensor that must be implanted.

Typically, each of the conductive traces includes a contact pad. The contact pad may simply be a portion of the conductive trace that is indistinguishable from the rest of the trace except that the contact pad is brought into contact with the conductive contacts of a control unit (e.g., the sensor control unit). More commonly, however, the contact pad is a region of the conductive trace that has a larger width than other regions of the trace to facilitate a connection with the contacts on the control unit. By making the contact pads relatively large as compared with the width of the conductive traces, the need for precise registration between the contact pads and the contacts on the control unit is less critical than with small contact pads.

To electrolyze the analyte, a potential (versus a reference potential) is applied across the working and counter electrodes. The minimum magnitude of the applied potential is often dependent on the particular electron transfer agent, analyte (if the analyte is directly electrolyzed at the electrode), or second compound (if a second compound, such as oxygen or hydrogen peroxide, whose level is dependent on the analyte level, is directly electrolyzed at the electrode). The applied potential usually equals or is more oxidizing or reducing, depending on the desired electrochemical reaction, than the redox potential of the electron transfer agent, analyte, or second compound, whichever is directly electrolyzed at the electrode. The potential at the working electrode is typically large enough to drive the electrochemical reaction to or near completion.

When a potential is applied between the working electrode and the counter electrode, an electrical current will flow. The current is a result of the electrolysis of the analyte or a second compound whose level is affected by the analyte. In one embodiment, the electrochemical reaction occurs via an electron transfer agent and the optional catalyst. Many analytes B are oxidized (or reduced) to products C by an electron transfer agent species A in the presence of an appropriate catalyst (e.g., an enzyme). The electron transfer agent A is then oxidized (or reduced) at the electrode. Electrons are collected by (or removed from) the electrode and the resulting current is measured.

As an example, an electrochemical sensor may be based on the reaction of a glucose molecule with two non-leachable ferricyanide anions in the presence of glucose oxidase to produce two non-leachable ferrocyanide anions, two hydrogen ions, and gluconolactone. The amount of glucose present is assayed by electrooxidizing the non-leachable ferrocyanide anions to non-leachable ferricyanide anions and measuring the current.

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), a source of nitric oxide, such as described in U.S. Pat. No. 7,128,904, as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect. Preferably, the anticlotting agent is incorporated in the lyotropic liquid crystal of this invention. For example, water-soluble heparin can be incorporated in, and be released from aqueous channels of the cubic phase lyotropic liquid crystals of this invention.

Insertion Device

An insertion device can be used to subcutaneously insert the sensor into the patient. The insertion device is typically formed using structurally rigid materials, such as metal or rigid plastic. Preferred materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, such as a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that operate the sensor and the analyte monitoring device system. The electronic components of the sensor control unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, such as transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Because both the thicknesses transport characteristics, such as glucose permeabilities, are well controlled in the optionally cubic phase lyotropic crystal films, for example when manufactured by doctor blading, the sensors can be optionally factory precalibrated.

If calibration is, however, desired then, in general, the calibration is preferably performed by measuring a signal at a particular point in time, meaning by one point calibration, as described in U.S. Pat. No. 5,593,852.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a sensor. In these embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display.

A threshold value is exceeded if the data-point has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the data-point indicates that the patient is hypoglycemic as defined by the threshold value. However, a data-point which correlates to a glucose level of 75 mg/dL would not exceed the same threshold value for hypoglycemia because the data-point does not indicate that particular condition as defined by the chosen threshold value.

An alarm may also be activated if the sensor readings indicate a value that is beyond a measurement range of the sensor. For glucose, the physiologically relevant measurement range is typically about 50 to 250 mg/dL, preferably about 40-300 mg/dL and ideally 30-400 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In general, lyotropic liquid crystals are single phase two component thermodynamically stable systems, where a lipid (or water) serves as a dispersant for water (or a lipid). The lyotropic liquid crystals form spontaneously and reproducibly in mixtures of amphiphilic lipids and water. Formation of a particular phase results of the hydrophobic bonding of the long lipid chains. Because of the affinity of the lipid chains for each other, the lipid microscopically phase separates from the water, and a continuous lipid domain and an also continuous aqueous domain are formed. In some, the resultant bi-continuous cubic phases, continuous and ordered aqueous channels are spontaneously and reproducibly formed. The cubic phases are clear, isotropic, hard, soap-like substances. The best researched cubic phase is formed of monoolein (glycerol monooleate) and water.

Although monoolein is hydrolyzed in the presence of serum lipases, we use in part of the experiment the well studied exemplary monoolein:water system, which forms a bi-continuous Pn3m diamond-like space group phase. It has four continuous aqueous channel systems, connected at knots. Its water-contacting specific surface is exceptionally large, 500-600 $m^2$ $g^{-1}$. This liquid crystal is stable in water.

Urate is an electro-oxidizable anionic interferent, common in serum and other biological fluids. It not only interferes with assays of analytes, but also destabilizes sensors. The following examples show that the undesired flux of urate to the wired enzyme coated cathode is reduced much more that the flux of oxygen, the analyte by a film of a cubic phase lyotropic liquid crystal. The film is applied by doctor blading. The following examples also show that mechanically strong films of a cubic phase lyotropic liquid crystal can be made by doping the liquid crystal having a lipid with a single long hydrophobic chain with a second lipid, having two long hydrophobic chains.

Chemicals and Materials

Bilirubin oxidase (BOD) from *Trachyderma tsunodae* (Tt) (1.89 U/mg, Amano, Lombard, Ill.), poly(ethylene glycol) (400) diglycidyl ether (PEGDGE) (Polysciences, Warrington, Pa.), uric acid (Sigma, St. Louis, Mo.) were used as received. Monoolein (1-oleoyl-rac-glycerol) was purchased from Sigma, and 1,2-dioleoyl-sn-glycero-3-phosphate monosodium salt from Avanti Polar Lipids, Inc. (Alabaster, Ala.). The measurements were performed in a pH 7.3 physiological buffer, containing 20 mM phosphate and 0.15 M of NaCl. The urate solution was prepared by dissolving uric acid in 20 mM NaOH then buffered to pH 7.3 with 20 mM $KH_2PO_4$, to produce a 10 mM urate stock solution. The wire used, a copolymer of acrylamide and N-vinylimidazole in which all the imidazole functions were complexed with $[Os(4,4'\text{-dichloro-2,2'-bipyridine})_2Cl]^{+/2+}$, (PAA-PVI-[Os(4,4'-dichloro-2,2'-bipyridine)$_2$Cl]$^{+/2+}$), was synthesized as described (Mano et al., *Journal of the American Chemical Society* 2002, 124, 6480-6486).

Preparation of the Electrodes

The rotating carbon cloth $O_2$-electrodes were prepared as reported (Mano et al., *Journal of the American Chemical Society* 2002, 124, 6480-6486; Barton et al., *Journal of the American Chemical Society* 2001, 123, 5802-5803). Smooth 0.196 $cm^2$ vitreous carbon electrodes (Pine Instruments, Raleigh, N.C.) were polished using 0.05 µm alumina, rinsed and dried, then a 0.35 mm thick, 5 mm diameter carbon cloth disc (Toray TGPH-120, E-TEK, Somerset, N.J.) was attached using conducting carbon paste (Structure Probe, Inc. West Chester, Pa.). After drying for 1 h, the cloth was made hydrophilic by exposure to $O_2$ plasma (10 min, 1 Torr $O_2$). 10 µL aliquots of a mixture of 20 µL of 6 mg/mL wiring redox polymer solution in water, 3.6 µL of 30 mg/ml bilirubin oxidase in phosphate buffer, and 4.1 µL of 4 mg/mL PEGDGE in water and 13 µL of the physiological phosphate buffer were pipetted onto the carbon cloth. The electrocatalyst composition and loading were: 0.15 mg/$cm^2$ redox polymer; 0.135 mg/$cm^2$ bilirubin oxidase; and 0.021 mg/$cm^2$ of PEGDGE. The wired bilirubin oxidase film formed was cured at room temperature overnight.

Preparation of the Cubic Phase Lyotropic Liquid Crystals

The cubic phase lyotropic liquid crystals were prepared according to published procedures and phase diagrams (Koynova et al., *Chemistry and Physics of Lipids* 2002, 115, 107-219; Li, S. J.; Yamashita et al., *Biophysical Journal* 2001, 81, 983-993). The monoolein: water lyotropic liquid crystal comprising of 58 wt % monoolein and 42 wt % physiological buffer solution. The monoolein was weighed in an Eppendorf tube, the buffer solution was added, and the tube was closed and centrifuged several times for 5 minutes in a 5412 Eppendorf centrifuge at 15,000 G. The 1,2-dioleoyl-sn-glycero-3-phosphate-doped monoolein: water crystals were similarly prepared, but first the 1,2-dioleoyl-sn-glycero-3-phosphate was weighed, than monoolein was added to produce 0.5 to 10 mol % 1,2-dioleoyl-sn-glycero-3-phosphate containing monoolein. To avoid phase-separation by fractional crystallization, the lipids were dissolved in a drop of chloroform, which was flash evaporated at ~60° C., then the buffer was added to 30 weight % lipids. The Eppendorf tube was then tightly closed, and the mixture was aged for at least a day. When placed between crossed polarizers, just before their application, the cubic phase lyotropic liquid crystals appeared dark and featureless, except at their rim, where water was lost by evaporation and the phase was no longer cubic. The undoped monoolein: water lyotropic liquid crystal was stable for about six months, but the monoolein:water:10 mol % of 1,2-dioleoyl-sn-glycero-3-phosphate liquid crystal was stable only for about three weeks, because of slow hydrolysis of the lipid.

Coating of the Electrodes with Lyotropic Liquid Crystals

The liquid crystal coating was applied by placing a 6 mm ID, 0.50 mm high plastic spacer on the 0.35 mm thick carbon cloth, already cemented to the vitreous carbon rotating electrode. Alternatively the vitreous carbon rotating electrode itself was coated with the lyotropic liquid crystal, using a 0.15 mm high spacer. The spacer was filled with the liquid crystal using a pipette tip, and the excess of the liquid crystal was removed with a spatula, before lifting off the spacer. The weight of the liquid crystal on the carbon cloth bound to the carbon disc was 5.5-6.0 mg, and that on the 5 mm diameter vitreous carbon disc was 4.0-4.5 mg. The liquid crystal film on the carbon cloth did not substantially penetrate the pores and its thickness equaled the height of the spacer, 0.15 mm.

Instrumentation and Cell

The electrodes were rotated with a Pine Instruments (Grove, Pa.) rotator. The measurements were performed using a Model CHI832 potentiostat (CH-Instruments, Austin, Tex.) in a three electrode cell, maintained at 37.5° C. by an isothermal circulator (Fisher Scientific, Pittsburgh, Pa.). The cell had a platinum wire counter electrode and an Ag/AgCl (3 M NaCl) reference electrode.

Example 1

Increase of Permeation of the $Ru(NH_3)_6^{3+}$ Cation and Decrease of the Permeation of the $Fe(CN)_6^{3-}$ Anion Upon 1,2-Dioleoyl-Sn-Glycero-3-Phosphate-Doping of the Monoolein:Water Lyotropic Liquid Crystal The voltammetric data in Table 1, obtained at a 10 mV $s^{-1}$ scan rate, summarize the observations for uncoated (bare) smooth vitreous carbon electrodes, for vitreous carbon electrodes coated with undoped monoolein:water, and for vitreous carbon electrodes coated with monoolein:water doped with 2 mol % of 1,2-dioleoyl-sn-glycero-3-phosphate. In Table 1, the potentials (E) are in mV; $I_{be}$ refers to the current of the bare electrode; $E_f$ is the formal potential; $E_a-E_c$ is the difference between the anodic and the cathodic maxima. The electrochemically reversible reduction of the cation $Ru(NH_3)_6^{3+}$ (1 mM) to $Ru(NH_3)_6^{2+}$ and of the anion $Fe(CN)_6^{3-}$ (1 mM) to $Fe(CN)_6^{4-}$ were probed, along with the irreversible oxidation of urate (0.5 mM). (FIG. 1) The electrolyte was an aqueous, pH 7.3, 0.15 M NaCl, 20 mM phosphate solution. Application of the monoolein:water lyotropic liquid crystal reduced the voltammetric peak height of the $Ru(NH_3)_6^{3+}$ wave 11 fold and of height of the $[Fe(CN)_6]^{3-}$ wave 18 fold. Doping of the monoolein:water lyotropic liquid crystal with 1,2-dioleoyl-sn-glycero-3-phosphate increased the $Ru(NH_3)_6^{3+}$ peak height 6 fold but decreased that of $[Fe(CN)_6]^{3-}$ 1.8 fold. Because the solution-phase concentrations of $[Ru(NH_3)_6]^{3+}$ and $[Fe(CN)_6]^{3-}$ were the same, and because their diffusion coefficients at 25° C. differ only by 20% ($7.17\times10^{-6}$ cm$^2$s$^{-1}$ at pH 3.0 in 0.5 M KCl for $[Fe(CN)_6]^{3-}$; $5.48\times10^{-6}$ cm$^2$s$^{-1}$ in pH 7.0 phosphate buffer, for $[Ru(NH_3)_6]^{3+}$) (Baur et al., *Journal of Electroanalytical Chemistry and Interfacial Electrochemistry* 1991, 305, 73-81), the observed 40% difference in peak currents after application of the undoped lyotropic liquid crystal is attributed in part to the larger diameter of the $[Fe(CN)_6]^{3-}$ anion, which reduces its diffusion in the narrow water channels of the lyotropic liquid crystal. The 6 fold increase in the peak height of $[Ru(NH_3)_6]^{3+}$ upon doping the liquid crystal with 2 mol % 1,2-dioleoyl-sn-glycero-3-phosphate is attributed to the anionic phosphate in the aqueous channel walls. Because the anionic charge is balanced by the charge of solution-phase cations, including $[Ru(NH_3)_6]^{3+}$, the concentration of $[Ru(NH_3)_6]^{3+}$ in the liquid crystal is higher than in the solution, and the permeability, which is the product of the diffusion coefficient and the concentration, increases for the cation, but not for the anion, correspondingly. The 1.8 fold decrease in the peak height for $[Fe(CN)_6]^{3-}$ upon 1,2-dioleoyl-sn-glycero-3-phosphate doping is attributed to its electrostatic repulsion of the anionic walls of the aqueous channels, which narrows the effective channel diameter for anion-diffusion.

TABLE 1

Effects of liquid crystal film coatings on the voltammetric characteristics of smooth vitreous carbon electrodes

| | $[Ru(NH_3)_6]^{3+}$ | | | $[Fe(CN)_6]^{3-}$ | | |
|---|---|---|---|---|---|---|
| Coating | $E_f$ | $E_a - E_c$ | % of $I_{be}$ | $E_f$ | $E_a - E_c$ | % of $I_{be}$ |
| None | −159 | 69 | 100.0 | +199 | 88 | 100.0 |
| monoolein: water | −158 | 76 | 8.6 | +197 | 87 | 5.5 |
| monoolein: water: 2% 1,2-dioleoyl-sn-glycero-3-phosphate | −192 | 68 | 60.0 | +196 | 102 | 3.0 |

Coating the smooth vitreous carbon electrode with monoolein:water:2 mol % 1,2-dioleoyl-sn-glycero-3-phosphate shifted the formal potential of $[Ru(NH_3)_6]^{2+/3+}$ by +33 mV, but did not change the peak separation. The up-shift is attributed to greater ion pairing of $[Ru(NH_3)_6]^{3+}$ than of $[Ru(NH_3)_6]^{2+}$ with wall anions. While the peak height of $[Ru(NH_3)_6]^{3+}$ is as much as 60% of that of the bare electrode when the carbon electrode is coated with the anionic lipid doped liquid crystal, the peak current of $[Fe(CN)_6]^{3-}$ is only 3.0% of that of the bare electrode when the electrode is coated with the anionic lipid doped liquid crystal. Unlike the formal potential of $[Ru(NH_3)_6]^{2+/3+}$, which is up-shifted by the preferred electrostatic interaction of the oxidized member of the redox couple, the formal potential of $[Fe(CN)_6]^{3/4-}$ is not changed by 2 mol % 1,2-dioleoyl-sn-glycero-3-phosphate doping. In summary, making the walls of the aqueous channels of the liquid crystals anionic, increases the permeation rate of cations and slightly reduces the permeation rate of anions, increasing 12-fold, from 1.6 to 20, the $[Ru(NH_3)_6]^{3+}/[Fe(CN)_6]^{3-}$ electroreduction current ratio.

Example 2

Figure 2:
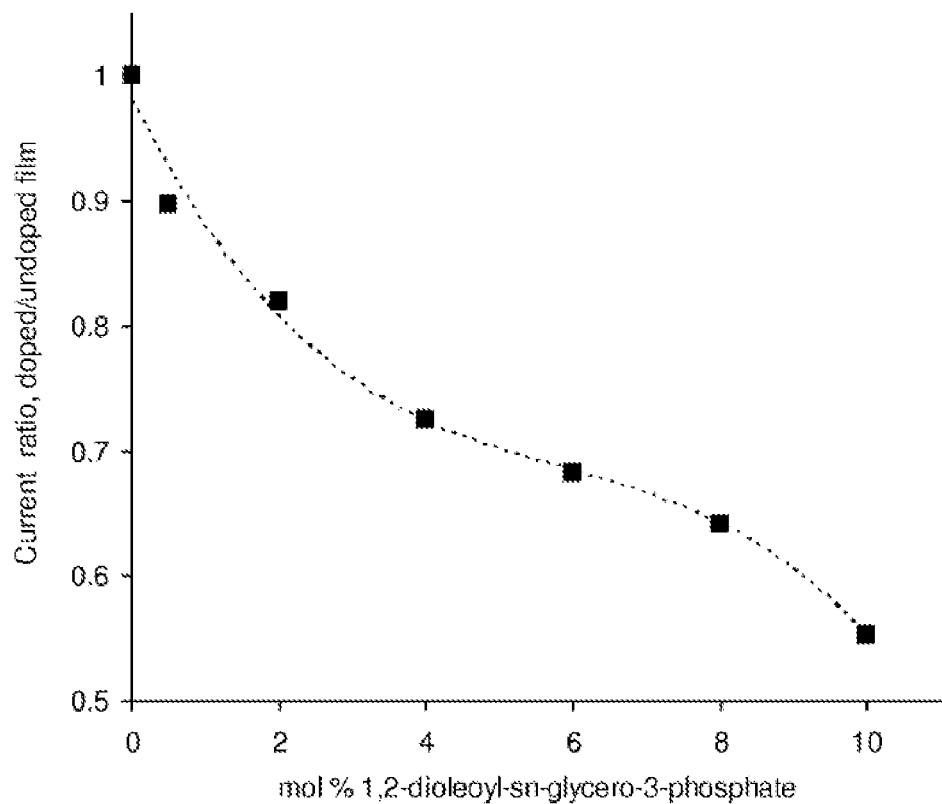
FIG. 2 shows the dependence of the ratio of the peak urate electrooxidation currents of electrodes coated with increasingly 1,2-dioleoyl-sn-glycero-3-phosphate doped monoolein:water and undoped monoolein:water liquid crystal films. Conditions as in FIG. 1.

Reduction of the Urate Electrooxidation Current by Un-Doped and by 1,2-Dioleoyl-Sn-Glycero-3-Phosphate-Doped Monoolein:Water Lyotropic Liquid Crystal Coatings in Stagnant Solutions FIG. 1, panel C and Table 2 show the effect of coating the smooth vitreous carbon electrodes with monoolein:water and with monoolein:water:2 mol % 1,2-dioleoyl-sn-glycero-3-phosphate on the electrooxidation of 0.5 mM urate. In the absence of the liquid crystal coatings, the urate electrooxidation wave peaks in the first voltammogram at +0.341 V then shifts positive as the electrode is increasingly fouled by the electrooxidative polymerization product of urate (Binyamin et al., A. *Journal of Electroanalytical Chemistry* 2001, 500, 604-611). The monoolein:water coating shifted the peak potential by +21 mV and the monoolein:water:2 mol % 1,2-dioleoyl-sn-glycero-3-phosphate coating by +47 mV. The shifts are attributed to reduced urate surface concentration on the carbon electrodes. Because the charge of urate is only ⅓$^{rd}$ of that of $Fe(CN_6)^{3-}$, it is less electrostatically repelled from the anionic channel walls, allowing the urate to diffuse through a larger fraction of the cross-sectional channel area. Thus 2 mol % 1,2-dioleoyl-sn-glycero-3-phosphate doping decreased the permeation of urate only by about 25%, while it decreased the permeation of $Fe(CN_6)^{3-}$ by 40%. Higher 1,2-dioleoyl-sn-glycero-3-phosphate doping resulted in greater wall charge, and the increased electrostatic repulsion confined the urate to a lesser cross sectional area, reducing its permeation. (FIG. 2) With water, greater doping (>0.5 mol % of 1,2-dioleoyl-sn-glycero-3-phosphate) changes the Pn3m diamond-like space group cubic phase liquid crystal to the also cubic, but more hydrated, Im3m phase (Li et al., *Biophysical Journal* 2001, 81, 983-993). This is not the case, however, in 0.15 M NaCl, where the space group of the monoolein:water:10 mol % 1,2-dioleoyl-sn-glycero-3-phosphate remains cubic Pn3m. At 0.15 M NaCl concentration the urate electrooxidation current is only 9.3% of that on the bare electrode after the electrode is coated with monoolein:water:10 mol % 1,2-dioleoyl-sn-glycero-3-phosphate. The voltammetric peak for monoolein:water:10 mol % 1,2-dioleoyl-sn-glycero-3-phosphate coated electrode is +0.35V, downshifted by −0.04 V from that of monoolein:water:2 mol % 1,2-dioleoyl-sn-glycero-3-phosphate, showing that the wall charge reduces the dissociation of uric acid, i.e. increasing its effective p$K_a$, and facilitating its oxidation.

TABLE 2

Urate Electooxidation on Uncoated and Lyotropic Liquid Crystal-Coated Smooth Vitreous Carbon Electrodes

| Coating | $E_p$ [mV] | % of $I_{be}$ |
|---|---|---|
| None | +341 | 100.0 |
| monoolein: water | +362 | 16.5 |

TABLE 2-continued

Urate Electooxidation on Uncoated and Lyotropic Liquid Crystal-Coated Smooth Vitreous Carbon Electrodes

| Coating | $E_p$ [mV] | % of $I_{be}$ |
|---|---|---|
| monoolein: water (2 mol % 1,2-dioleoyl-sn-glycero-3-phosphate) | +388 | 12.5 |

*$I_{be}$ is the urate electrooxidation current on uncoated smooth vitreous carbon. $E_p$ is the potential of the voltammetric peak of the first scan. 10 mV s$^{-1}$ scan rate.

Example 3

Figure 3:
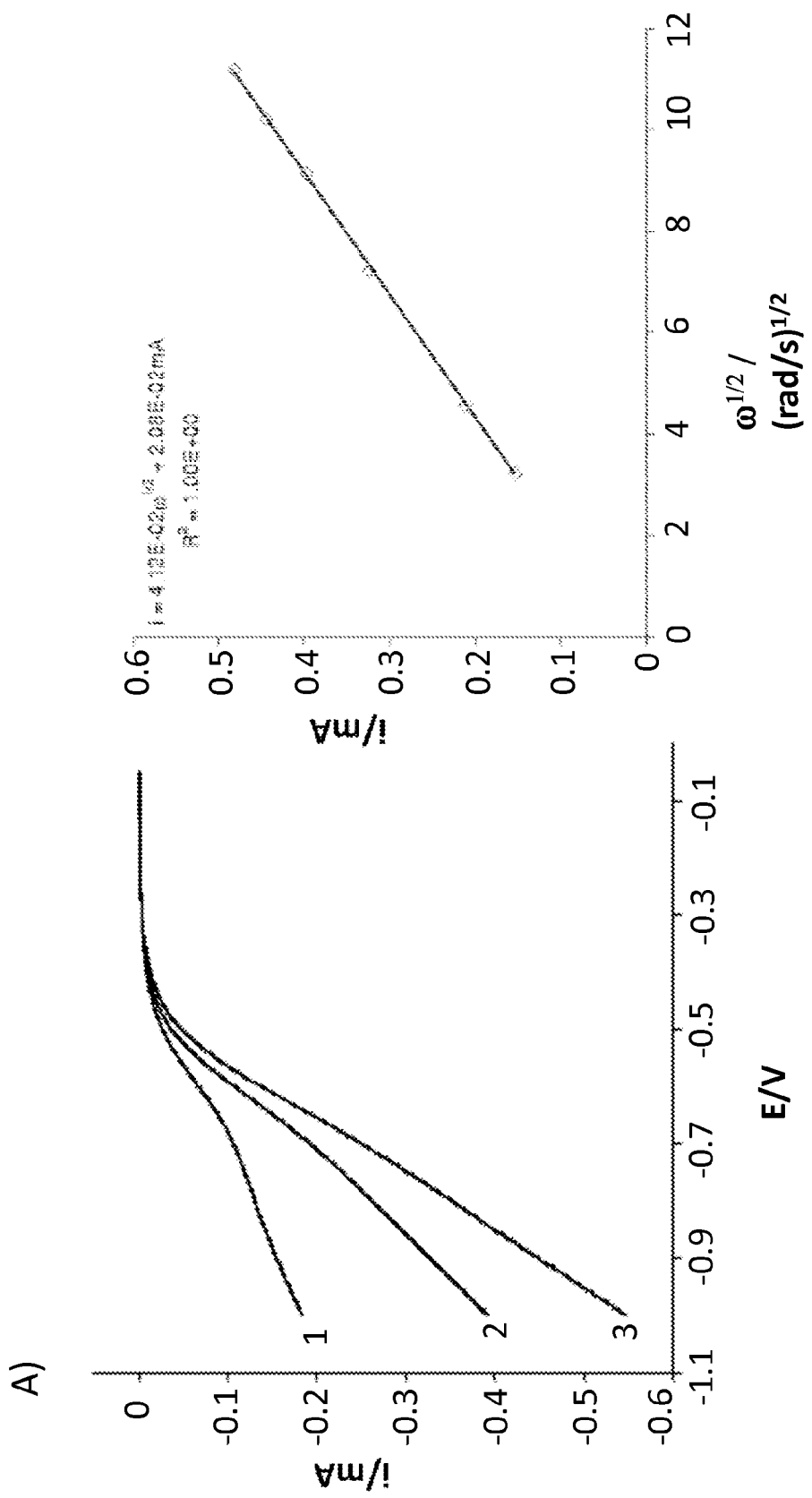
FIG. 3 shows polarizations of O$_2$ cathodes without the wired bilirubin oxidase electrocatalyst and their Levich plots measured at −0.9 V (Ag/AgCl). Bare (left) and smooth (right) vitreous carbon (Panel A); coated with monoolein:water:10 mol % 1,2-dioleoyl-sn-glycero-3-phosphate liquid crystal (Panel B, left (bare), right (smooth)); Koutecky-Levich plots (Panel C) of the bare (open rhombs) and modified (solid rhombs) electrodes poised at −0.9 V (Ag/AgCl). 1-100 rpm; 2-500 rpm; 3-1000 rpm. Scan rate 5 mVs$^{-1}$; 1 atm O$_2$; other conditions as in FIG. 1.
Figure 3:
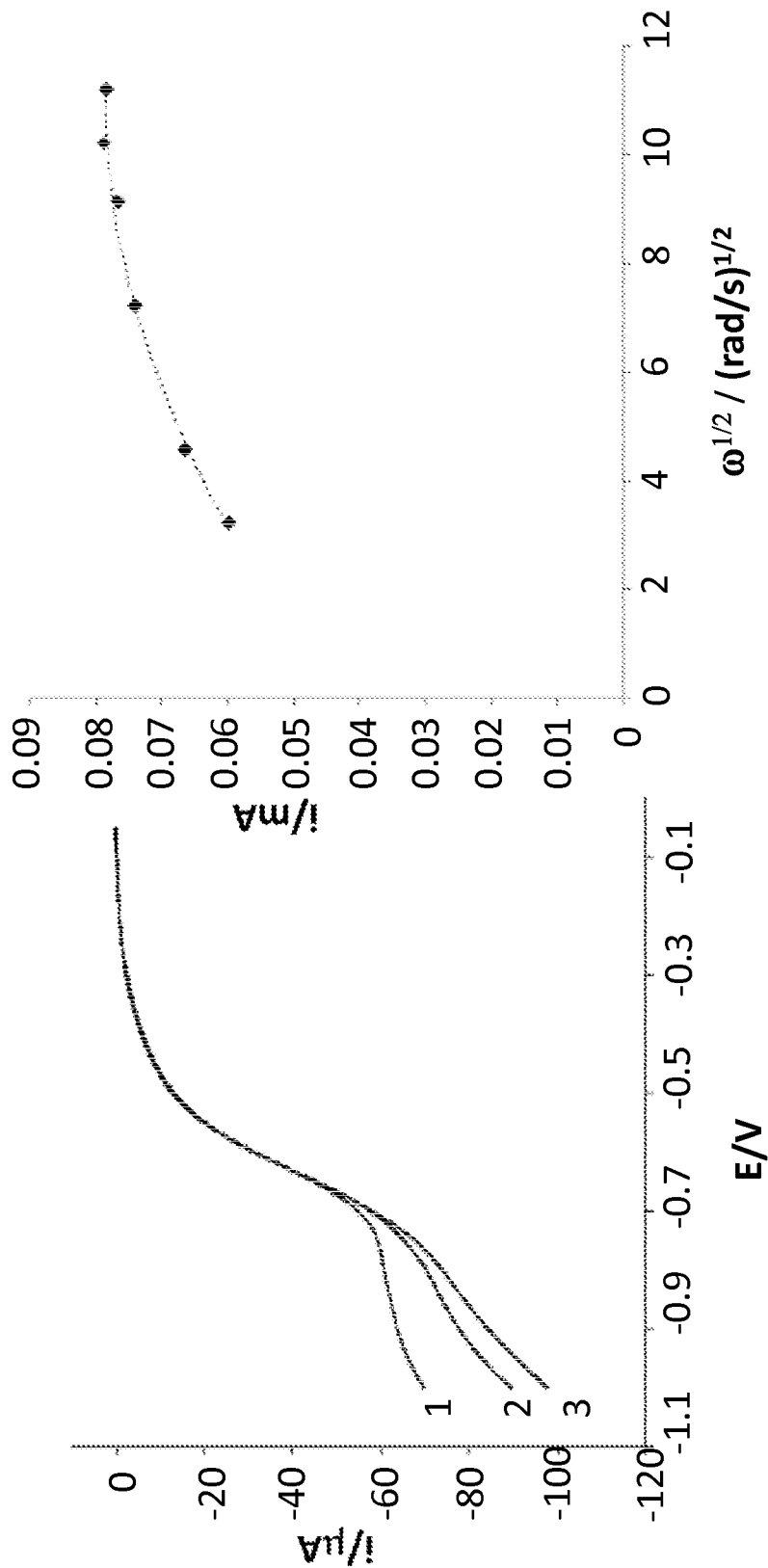
Figure 3:
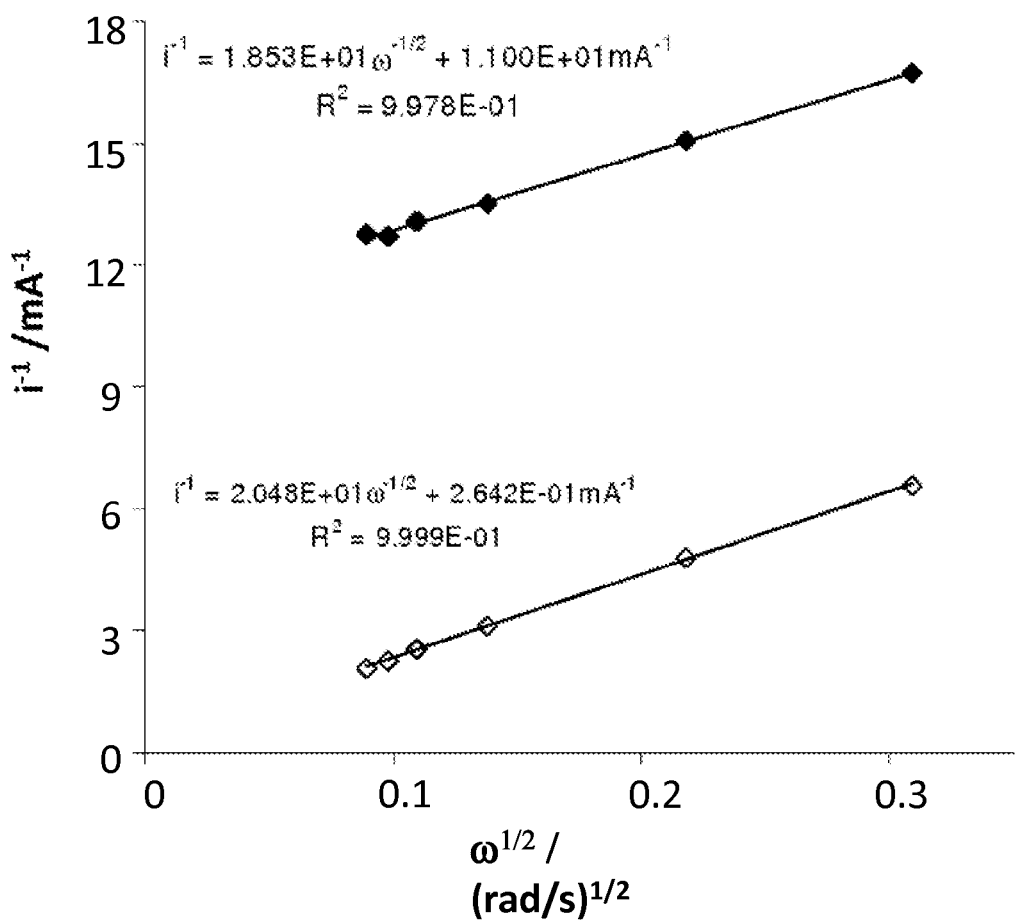

Change in the Oxygen Flux Upon Applying the Monoolein/Water 10 Mol % 1,2-Dioleoyl-Sn-Glycero-3-Phosphate Film to Rotating Smooth Vitreous Carbon Electrodes FIG. 3, panel A, shows the potential dependence of the $O_2$ electroreduction current as a function of the angular velocity for the bare vitreous carbon electrode. In the Levich plot (Equation 1) (FIG. 3, panel A, right panel) the mass transport limited current increases, as expected, linearly with the square root of the angular velocity between 100 to 1200 rpm. This is represented by equation 1:

$$i = 0.620 nFAD^{2/3}\omega^{1/2}\nu^{-1/6}C_s \qquad (1)$$

where n is the number of electrons exchanged, F is a Faraday's constant, D is the diffusion coefficient of the electroactive species, v is the kinematic viscosity, $C_s$ is the concentration of $O_2$ and ω is the angular velocity. FIG. 3, panel b, shows the potential dependence of the $O_2$ electroreduction current as a function of the angular velocity for the electrode coated with monoolein:water:10 mol % 1,2-dioleoyl-sn-glycero-3-phosphate. Although the current still increased with $\omega^{1/2}$, the increase was no longer linear, especially at the higher rotation rates (FIG. 3, panel B, right panel). Such behavior was observed by Gough and Leypoldt (Gough et al., Analytical Chemistry 1980, 52, 1126-1130; Gough et al., Analytical Chemistry 1979, 51, 439-444) in rotating polymeric membrane-covered disc electrodes, for which the current, $i_d$, was where i is the $$i_d = i\left[\frac{1}{1+\frac{P_s}{P_m}}\right] \qquad (2)$$

current in the absence of membrane (the current from the Levich equation (1)); $P_m$ and $P_s$ are the respective permeabilities of the membrane and the solution; $D_m$ is the diffusion coefficient of $$P_m = \frac{\alpha D_m}{\delta_m} \qquad (3)$$

$$P_s = \frac{D}{\delta_d} \qquad (4)$$

electroactive probe in the membrane; a is a partition coefficient, i.e. the concentration in the membrane divided by the concentration in the solution; $\delta_m$ is the thickness of the membrane; D is the diffusion coefficient of the probe in the solution; and $\delta_d$ is the thickness of the diffusion layer. For mixed membrane and solution transport control, Equation 2 predicts linear dependence of the current with rotation rate at slow rotation rates and high membrane permeability. For low membrane permeability, the current is membrane transport controlled and is independent of rotation rate. Equation 2 can be rewritten (Leddy et al., Journal of Electroanalytical Chemistry and Interfacial Electrochemistry 1983, 153, 223-242) as Equation 5, where $i_{lim}$ is a steady state limiting current of the membrane-covered $$\frac{1}{i_{lim}} = \frac{1}{i} + \frac{\delta_m}{nFA\alpha D_m C_s} \qquad (5)$$

rotating disc electrode at a sufficiently large over-potential for the reaction not to be limited by the electron transfer rate on the electrode. According to Equation 5, the plots of the reciprocal of the currents vs. the reciprocal of the angular velocity, i.e. the Levich-Koutecky plots, have identical slopes for the modified and the bare electrodes, but the intercepts for the membrane coated electrodes are now defined by the permeability of the membrane. Indeed, as seen in FIG. 3, panel C, both plots, for the bare and for the modified electrodes, have slopes differing only by 10%. While application of the lyotropic liquid crystal reduces the effective electrode area on which $O_2$ is electroreduced, the crystal is permeable to $O_2$ and the current still increases, though no longer linearly, with the square root of the angular velocity.

Example 4

Figure 4:
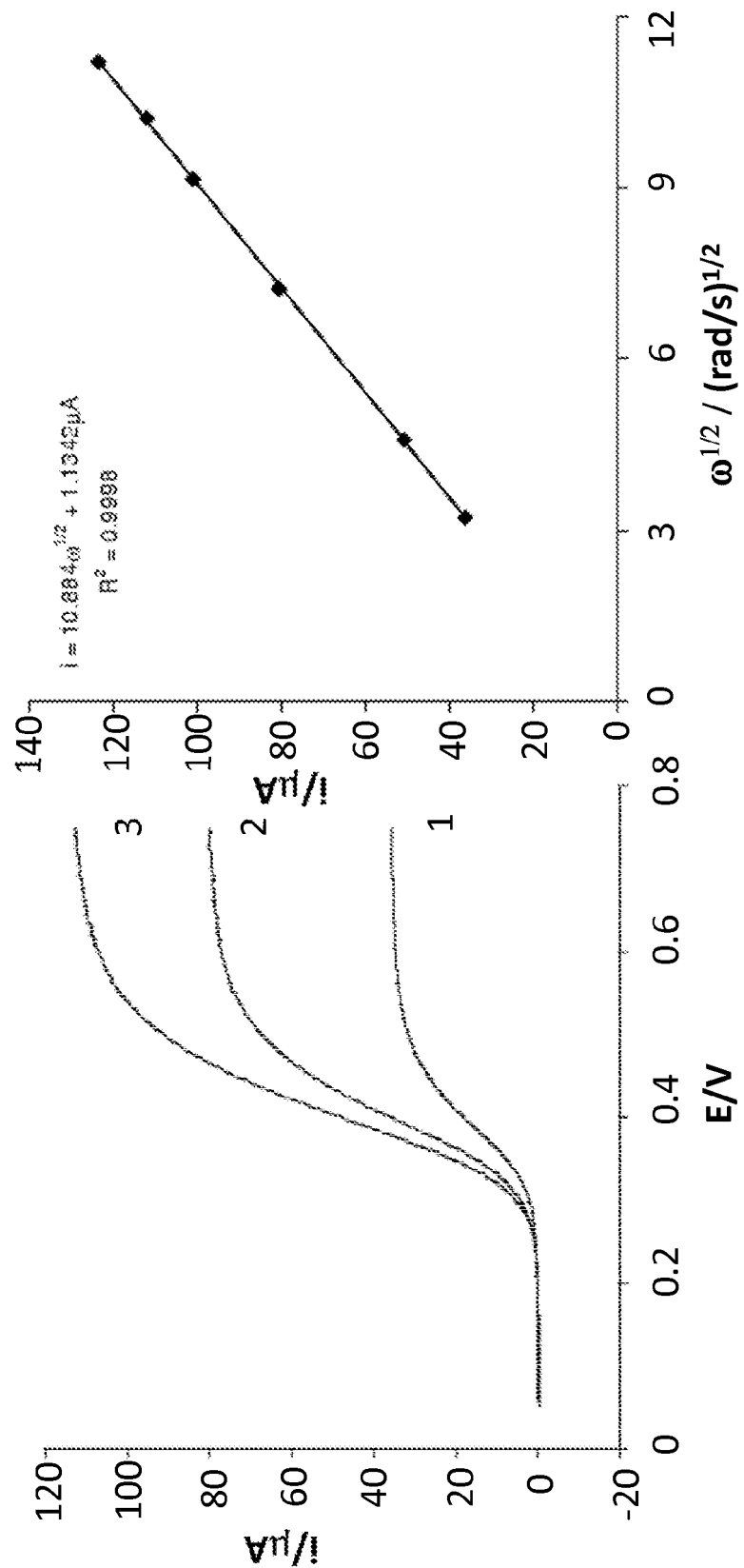
FIG. 4 shows polarizations (left) of the 0.5 mM urate-electrooxidizing rotating vitreous carbon electrodes and their Levich plots (right) measured with the electrodes poised at +0.7 V (Ag/AgCl). Bare electrode (Panel A); monoolein:water:10 mol % 1,2-dioleoyl-sn-glycero-3-phosphate liquid crystal coated electrode (Panel B). The Levich plots (Panel B, right) are of an electrode coated with monoolein:water:10 mol % 1,2-dioleoyl-sn-glycero-3-phosphate. 1-100 rpm, 2-500 rpm, and 3-1000 rpm; scan rate 5 mVs$^{-1}$; other conditions as in FIG. 1.
Figure 4:
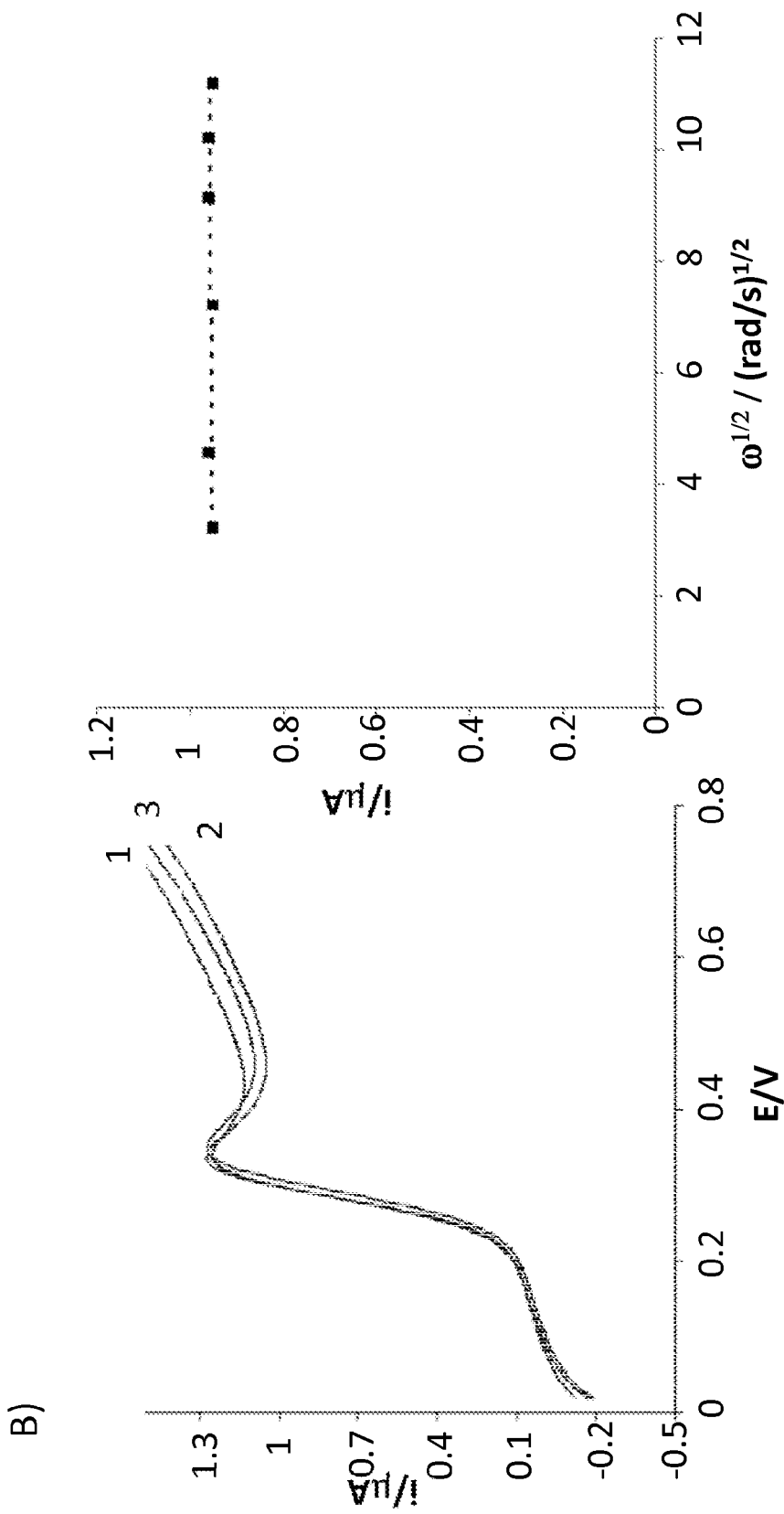

Increasing the $O_2$-Electroreduction: Urate-Electrooxidation Current Ratio by Rotating the Monoolein:Water:10 Mol % 1,2-Dioleoyl-Sn-Glycero-3-Phosphate Coated Electrode The urate electrooxidation current on the bare electrode poised at +0.7 V (FIG. 4 top, left) is solution transport controlled, increasing linearly with $\omega^{1/2}$ (FIG. 4, top, right). In contrast, the urate oxidation current at the monoolein:water:10 mol % 1,2-dioleoyl-sn-glycero-3-phosphate overcoated electrode does not change when the rotation rate is increased from 100 to 1200 rpm (FIG. 4, bottom left). The urate transport is controlled now by the monoolein:water:10 mol % 1,2-dioleoyl-sn-glycero-3-phosphate film. Because the $O_2$ transport increases with the rotation rate, but the urate transport does not, the ratio of the $O_2$ electroreduction/urate electrooxidation currents increases with the rate of rotation, reducing the fraction of the current lost to electrooxidation of urate and to $O_2$ scavenging by the intermediate urate electrooxidation product. For the bare carbon electrode in the stagnant solution the urate electrooxidation current was about 30% of the $O_2$ electroreduction current. It dropped to 2% upon coating with monoolein:water:10 mol % 1,2-dioleoyl-sn-glycero-3-phosphate, then dropped further, to 1%, when the electrode was rotated at 1000 rpm. The permeation of urate was drastically reduced, yet the $O_2$ electroreduction current for the rotating electrode coated with the 150 μm thick monoolein:water:10 mol % 1,2-dioleoyl-sn-glycero-3-phosphate film was 20% of that for the bare electrode. Unlike the urate, the $O_2$ permeated through both the lipid substructure and through the aqueous channels of the cubic phase lyotropic liquid crystal.

Example 5

Improving the Shear Strengths of the Lyotropic Liquid Crystals by their Doping

The monoolein:water:10 mol % 1,2-dioleoyl-sn-glycero-3-phosphate film on the 5 mm carbon disc was mechanically stable for at least 4 hours under the high, 0.1 N m$^{-2}$, average shear stress, produced by rotation at 1000 rpm in the physiological buffer solution, while the undoped and the less doped monoolein:water:2 mol % 1,2-dioleoyl-sn-glycero-3-phosphate films were unstable. Both the undoped monoolein: water and the monoolein:water:2 mol % 1,2-dioleoyl-sn-glycero-3-phosphate films rapidly lost their cubic structure, the currents dropping to nil because of discontinuity of the water channels in the altered phases. The improvement in the mechanical strength is attributed to the hydrophobic bonds between the long and aligned alkyl chains of the lipids in the lyotropic liquid crystals. Lipids with two alkyl chains (Scheme 1) form two sets of hydrophobic bonds, acting in a manner analogous to crosslinkers of polymers, well known to mechanically strengthen plastics.

Example 6

Figure 5:
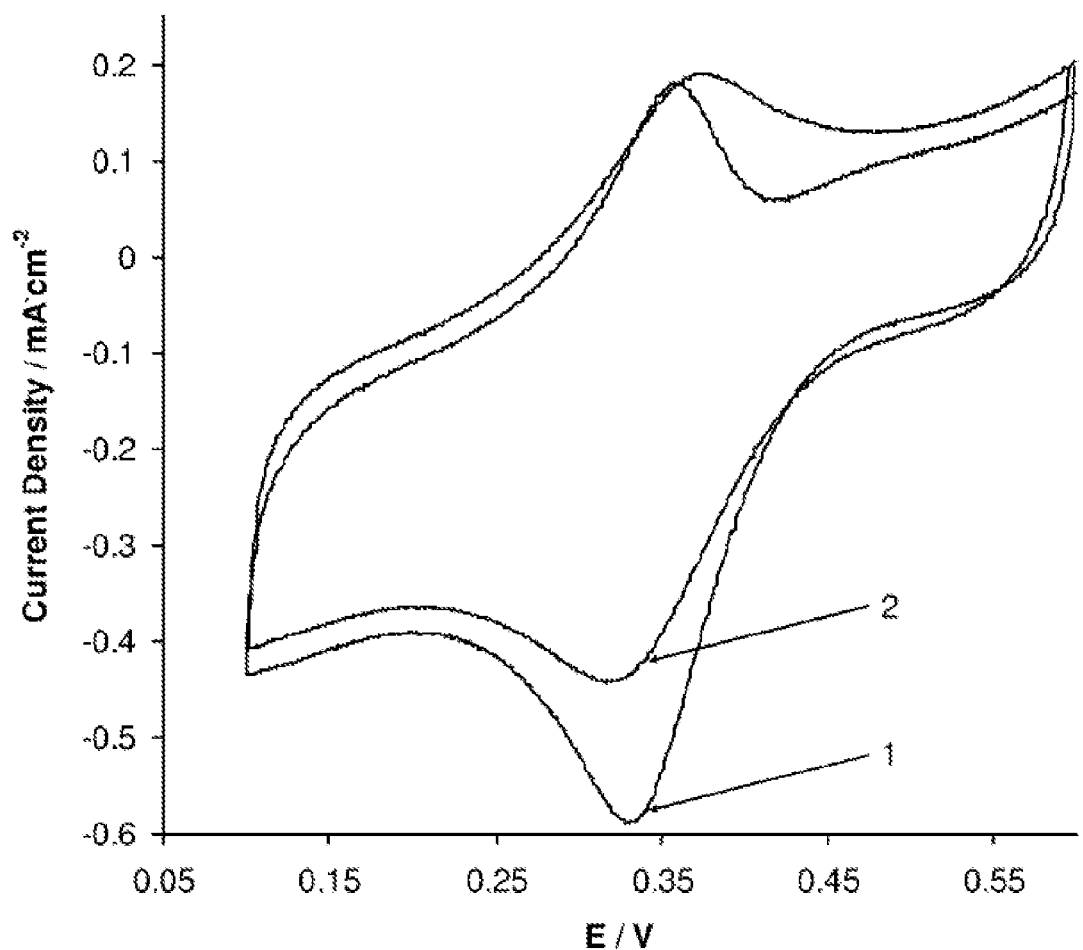
FIG. 5 shows cyclic voltammograms of the wired bilirubin oxidase-coated carbon cloth O$_2$ cathode. Line 1 represents no coating; line 2 represents coating with a 0.15 mm thick monoolein:water:10 mol % 1,2-dioleoyl-sn-glycero-3-phosphate film. 1 atm O$_2$; scan rate 5 mVs$^{-1}$; other conditions as in FIG. 1.
Figure 6:
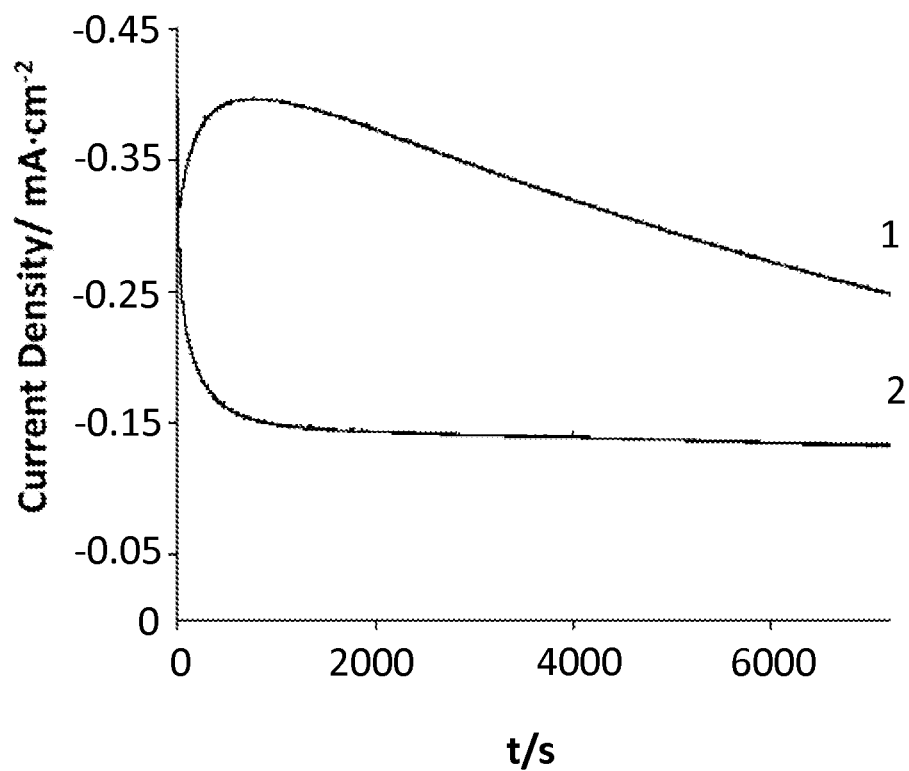
FIG. 6 shows the stabilization of the wired bilirubin oxidase-coated carbon cloth O$_2$ cathodes by lyotropic liquid crystal coating. No urate added (Panel A); urate added to 0.5 mM concentration at 2500 s (Panel B). Line 1 represents no coating; line 2 represents coating with a 0.15 mm thick monoolein:water:10 mol % 1,2-dioleoyl-sn-glycero-3-phosphate lyotropic film. 0.15 V (Ag/AgCl); 1 atm O$_2$; other conditions as in FIG. 1.
Figure 6:
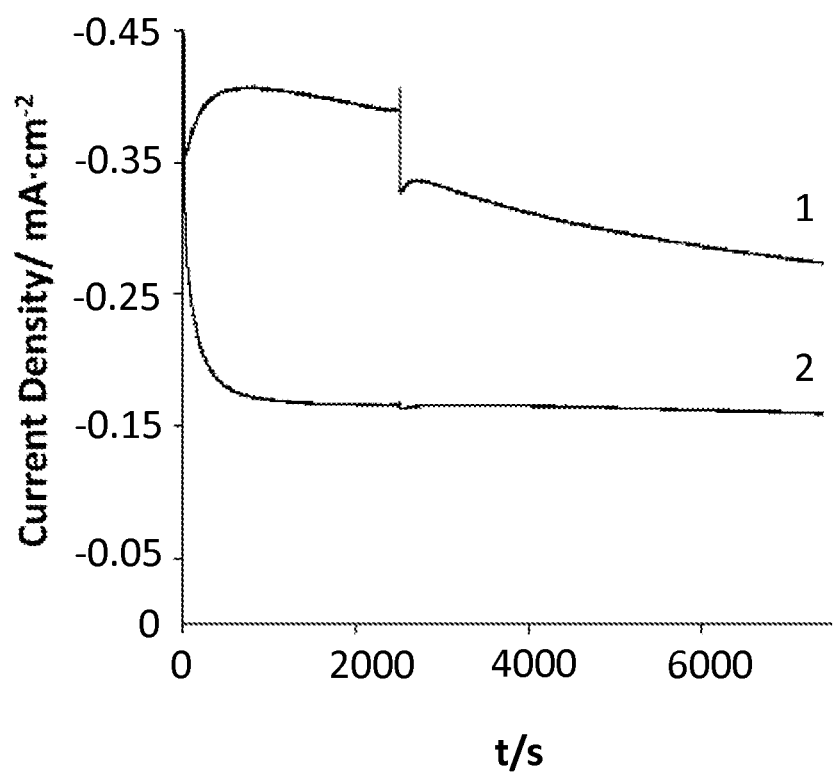

Stabilization of the Rotating Wired Bilirubin Oxidase O$_2$ Carbon Cloth Cathode by Coating with Monoolein:Water:10 Mol % 1,2-Dioleoyl-Sn-Glycero-3-Phosphate Oxygen-electroreducing wired copper enzyme (laccase) coated carbon cloth electrodes were made and characterized by Barton et al. FIG. 5 shows voltammograms of wired bilirubin oxidase carbon cloth O$_2$ cathodes without and with the monoolein:water:10 mol % 1,2-dioleoyl-sn-glycero-3-phosphate film. The stability of their currents is seen in FIG. 6, left, in absence of urate and FIG. 6, right, with urate added at t=2,500 s. The results (mean values +/− standard deviation from three experiments) are summarized in Table 4. In the 4700 s period following t=2,500, 79±12% of the current of the uncoated electrode rotating at 1000 rpm persisted in absence of urate, but 96±3% persisted when the electrode was coated with monoolein:water:10 mol % 1,2-dioleoyl-sn-glycero-3-phosphate. The uncoated, shear-stressed, rotating cathode lost its wired bilirubin oxidase electrocatalyst, while the mechanically strong liquid crystal coated electrode did not. When urate was added, and the protective lyotropic liquid crystal was not applied, the remaining current was 72±6%. However, even in the presence of urate, as much as 96±4% of the O$_2$ electroreduction current persisted when the wired bilirubin oxidase cathode was protected by the permeable monoolein:water:10 mol % 1,2-dioleoyl-sn-glycero-3-phosphate film, which greatly decreased the permeation of urate, but decreased much less the permeation of O$_2$.

TABLE 4

Stabilities of the current densities (j) of bare and monoolein: water (10 mol % 1,2-dioleoyl-sn-glycero-3-phosphate)-coated carbon cloth wired bilirubin oxidase O$_2$- cathodes

| | $j_{coated}/j_{bare}$ at 2450 s | $j_{7200s}/j_{2500s}$ bare cathode | $j_{7200s}/j_{2500s}$ liquid crystal-coated cathode |
|---|---|---|---|
| PBS, O$_2$ | 0.44 ± 0.11 | 0.79 ± 0.12 | 0.96 ± 0.03 |
| PBS, urate, O$_2$ | 0.43 ± 0.04 | 0.72 ± 0.06 | 0.96 ± 0.04 |

Example 7

Implantable Cubic Phase Lyotropic Liquid Crystal Coated Wired Enzyme Glucose Sensors Reproducible, uniform, mechanically strong glucose flux limiting membranes were produced of cubic phase lyotropic liquid crystals. In the process, a template-hole containing spacer is placed on the electrode and the cubic phase lyotropic liquid crystal is doctor-bladed onto the glucose oxidation electrocatalyzing film.

Unless otherwise indicated, the experiments were carried out in a pH 7.35, 0.15 M NaCl, 0.02 M phosphate buffer at 37° C. A three electrode cell with Ag/AgCl reference electrode and a platinum wire as counter electrode were prepared. The wired glucose oxidase film was formed on the 5 mm diameter (0.1963 cm$^2$) vitreous carbon disc working electrode by depositing on it 12 µL of a phosphate buffer solution, made by mixing at 34:41:25 v:v:v ratio solutions of GO$_x$, redox polymer X-7 and crosslinker PEGDGE400, each of 10 mg/mL concentration. The film was allowed to dry under ambient conditions and to cure overnight.

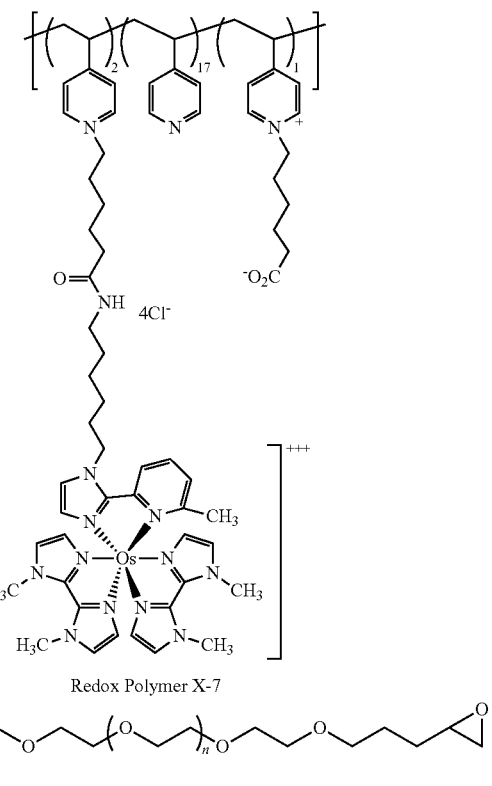

Redox Polymer X-7

Cross Linker (PEGDGE)

Where n = ca. 10

The lipid of the cubic phase lyotropic liquid crystal comprised 90 mol % monoolein (MO) and 10 mol % 1,2-dioleoyl-sn-glycero-3-phosphate To form the liquid crystal, the lipid (30 weight %) was mixed with the phosphate buffer solution (70 weight %). The lyotropic liquid crystal was applied to the wired glucose oxidase film coated working electrode by doctor blading, using a 0.10-0.11 mm thick polyester film in which a 5 mm diameter circular hole was cut. The hole, overlapping the vitreous carbon disk but not overlapping its Teflon rim was filled with an excess of the liquid crystal and the excess was removed using as a blade the straight edge of a stainless steel spatula.

The monoolein-saline water (0.06 M to 1.2 M NaCl) cubic phase can be doped with up to 10 mol % of anionic 1,2-dioleoyl-sn-glycero-3-phosphate retaining diamond type structure. The cubic phase lyotropic liquid crystal forms spontaneously from a mixture of lipids and an aqueous solution. It is a clear, isotropic, highly viscous, jelly-like substance, having ordered, continuous, fixed-diameter water channels of about 5 nm.

Figure 10:
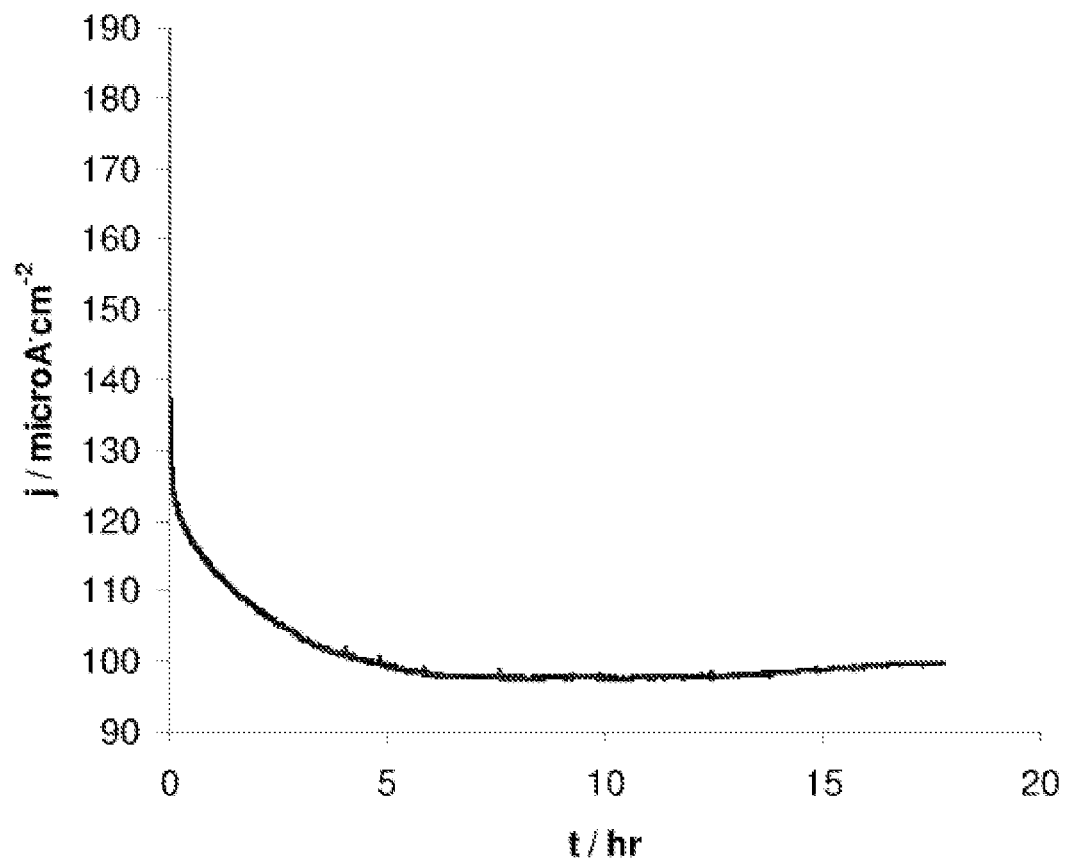
FIG. 10 shows the time dependence of the current density of the electrode of FIG. 7 operating under the conditions of FIG. 9 in a 50 mM glucose PBS solution at 37° C.

To mechanically strengthen the monoolein: water cubic phase lyotropic liquid crystal we dope it with an anionic surfactant, 1,2-dioleoyl-sn-glycero-3-phosphate. (Scheme 1) The doping mechanically strengthens the lyotropic liquid crystal. The membrane formed is not sheared off under its expected subcutaneous insertion and its conditions of use and it shields mechanically an electrically wired glucose oxidase film on a 5 mm diameter vitreous carbon disk electrode when the electrode is rotated at 1000 rpm. Because the walls of the water channels of the cubic phase lyotropic liquid crystal are tailored to be anionic, the influx of electrooxidizable anionic interferents is also reduced, improving the sensor's specificity for glucose.

ibility of the membranes, as reflected by the slopes of the calibration curves, was ±5% (n=10). FIG. 10 shows the stability of the current, i.e. the time dependence of the current density of the electrode of FIG. 7 poised at 0.12 V (Ag/AgCl) in a 50 mM glucose solution.

Figure 11:
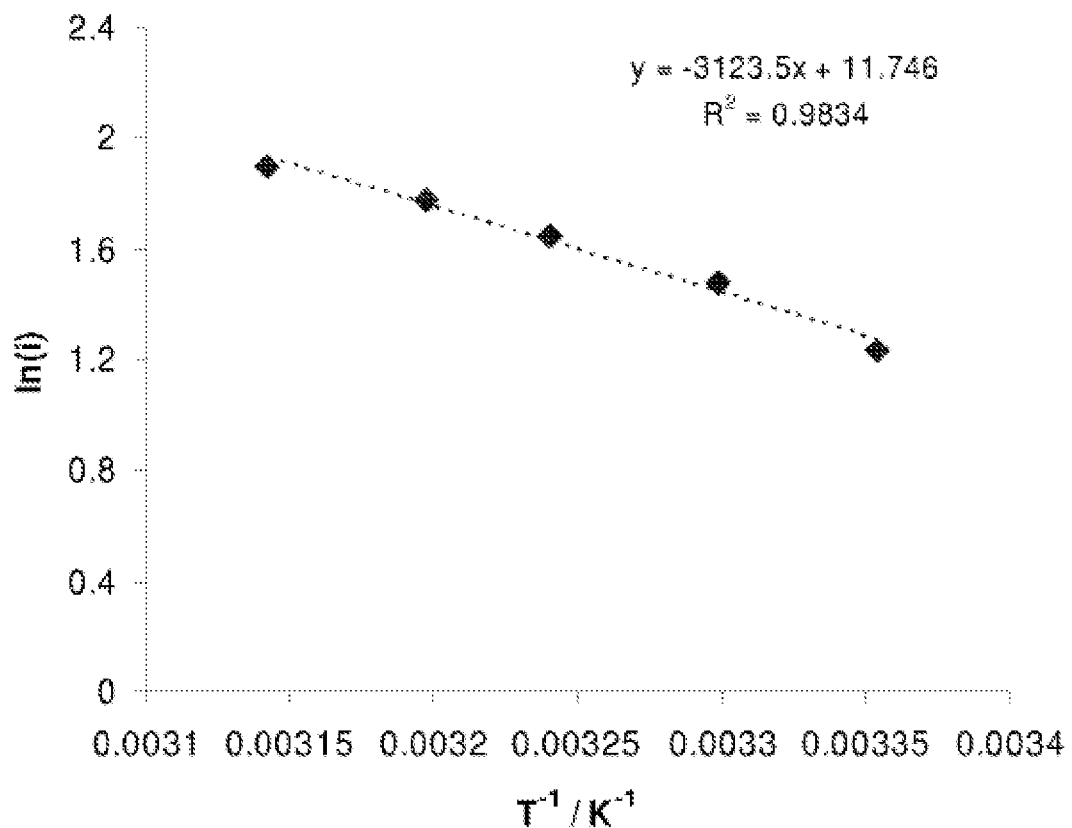
FIG. 11 shows the dependence of the logarithm of the current on the reciprocal temperature in 5 mM glucose in PBS.

Because the walls of the aqueous channels of the monoolein: 10 mol % 1,2-dioleoyl-sn-glycero-3-phosphate cubic phase lyotropic liquid crystal are anionic, adding 0.1 mM ascorbate did not measurably affect the current density at 5 mM glucose concentration. The activation energy, 26 kJ/mol, was calculated from the increase of the glucose electrooxidation current when the temperature was raised from 25° C. to 45° C., with the electrode poised at 0.12 V (Ag/AgCl) and rotated at 100 rpm in 5 mM glucose in PBS. (FIG. 11) It is advantageously smaller than in other wired GOx electrodes and is attributed to the small activation energy for glucose transport through the cubic phase lyotropic liquid crystal. The response times of the 5 mm diameter sensor coated with 4.5 mg of cubic phase lyotropic liquid crystal are seen it Table 5. Here the glucose oxidase was wired with $PVI_7$-[Os(dmebpy)$_2$Cl] and the electrode was poised at 0.45 V (Ag/AgCl).

TABLE 5

Response time of a 5 mm diam. glucose sensor coated with 4.5 mg of LLC

| Glucose concentration change initial→ final, mM | Time to 90% of the final current density | Time to >99% of the final current density |
|---|---|---|
| 0→1 | 6.2 min | 9 min |
| 1→6 | 6.2 min | 11.4 min |

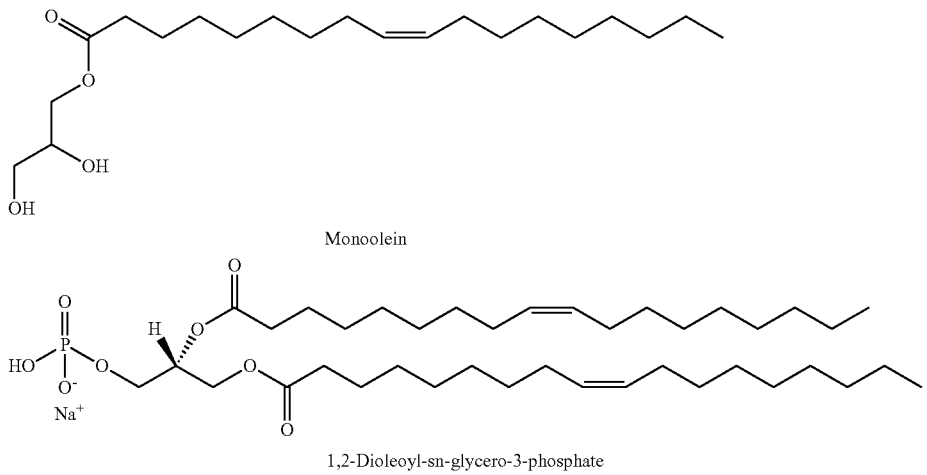

Scheme 1: Lipids of the Membrane

Monoolein 1,2-Dioleoyl-sn-glycero-3-phosphate

Figure 7:
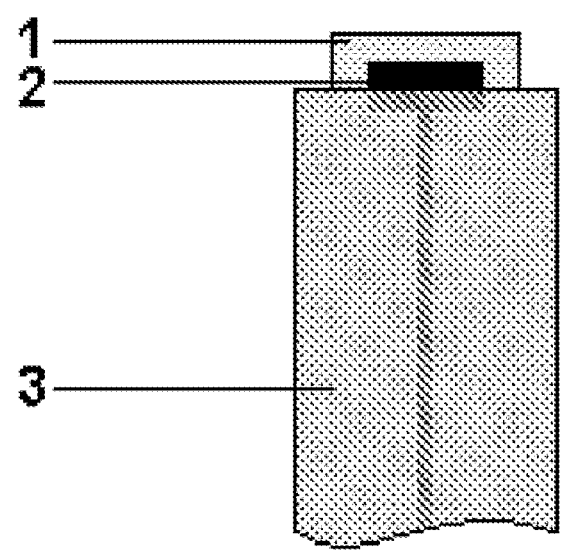
FIG. 7 shows the glucose electrooxidizing electrode. Element 1 is the cubic phase lyotropic liquid crystal membrane; element 2 is the wired glucose oxidase electrocatalyst; element 3 is the vitreous carbon electrode. Coatings 1 and 2 cover the entire surface of the 5 mm diameter vitreous carbon disk electrode.
Figure 8:
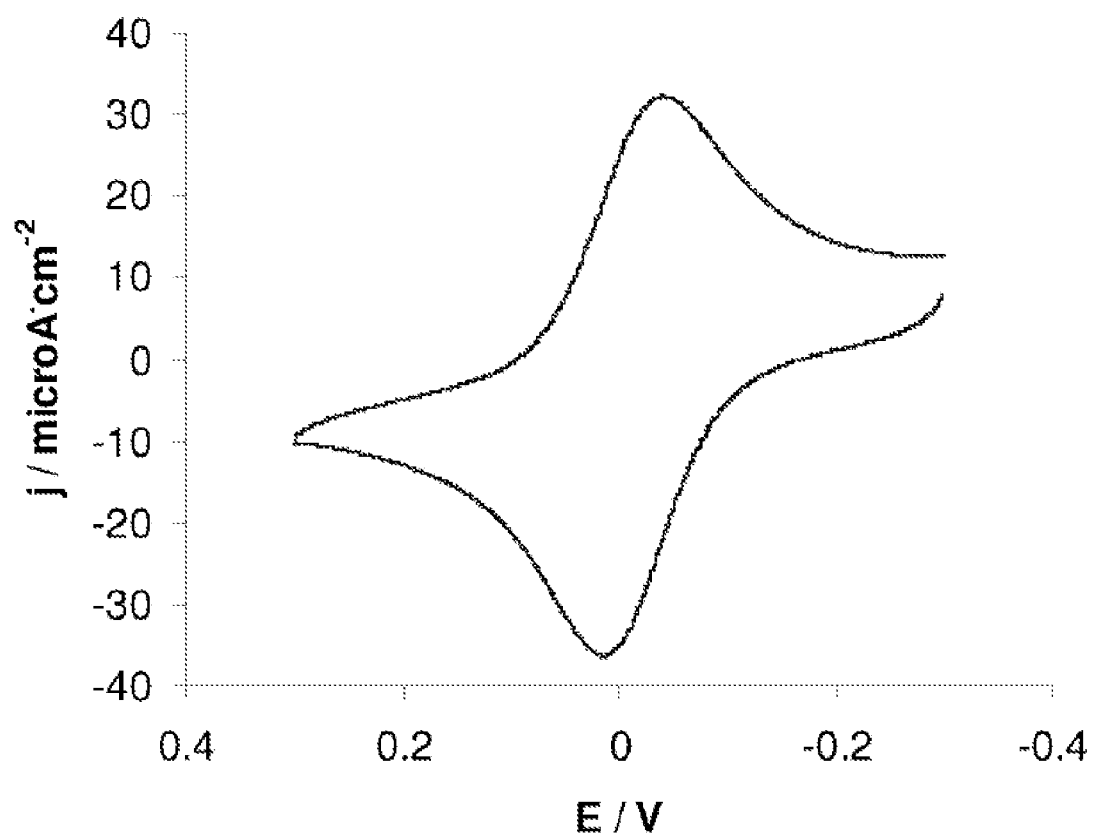
FIG. 8 is a cyclic voltammogram, in the absence of glucose and under argon, of the redox polymer X-7 wired glucose oxidase coated vitreous 5 mm diameter vitreous carbon disk electrode, overcoated with the 2.5 mg of the monoolein: 10 mol % 1,2-dioleoyl-sn-glycero-3-phosphate cubic phase lyotropic liquid crystal membrane. The thickness of the membrane is 0.105±0.05 mm. Scan rate 10 mV/s.

The 0.1 mm thick LLC film reduced the current density of glucose flux by about one order of magnitude. A schematic of the LLC coated sensor is seen in FIG. 7. FIG. 8 shows a cyclic voltammogram of the electrode coated with the wired glucose oxidase film and overcoated with the monoolein: 10 mol % 1,2-dioleoyl-sn-glycero-3-phosphate cubic phase lyotropic liquid crystal. The separation of the voltammetric peaks is 55 mV, shows mobility of the redox functions of the wire. The formal redox potential was −0.0135V (Ag/AgCl).

Figure 9:
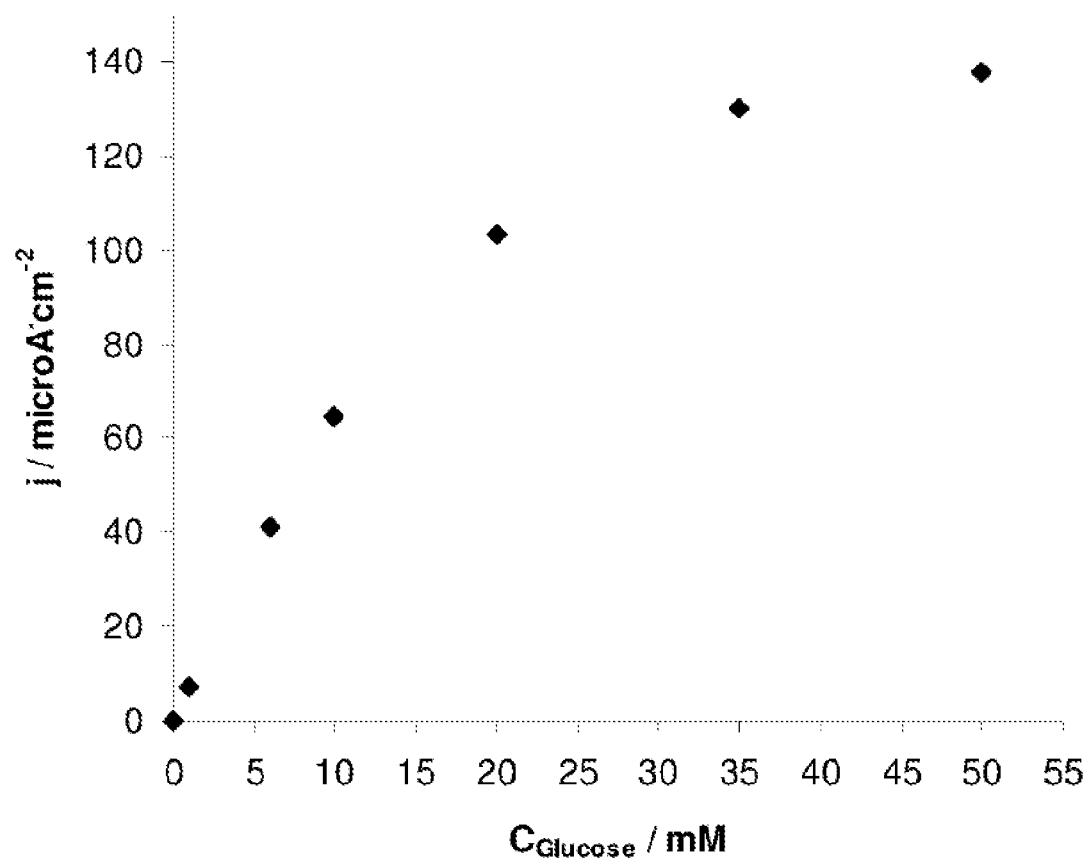
FIG. 9 shows the dependence of the steady state glucose electrooxidation current density on the glucose concentration at 37° C. The electrode of FIG. 7 was poised at 0.12V (Ag/AgCl) and was rotated at 100 rpm under argon.

FIG. 9 shows, for the electrode of FIG. 7 poised at 0.12V (Ag/AgCl) and rotated at 100 rpm, the calibration curve, i.e. the dependence of the steady state glucose electrooxidation current density on the glucose concentration. The reproduc- TABLE 5-continued Response time of a 5 mm diam. glucose sensor coated with 4.5 mg of LLC

| Glucose concentration change initial→ final, mM | Time to 90% of the final current density | Time to >99% of the final current density |
|---|---|---|
| 6→10 | 5.0 min | 10.3 min |
| 10→20 | 6.2 min | 12 min |
| 20→35 | 3 min | 6.7 min |
| 35→50 | 1.8 min | 4 min |

We found that because of the high activity of serum lipase, the cubic phase lyotropic liquid crystal is rapidly hydrolyzed in serum: After 5 hours, no LLC was present on the electrode. Such hydrolysis could be prevented by using lipids forming cubic phase Lyotropic liquid crystals that are resistant to hydrolysis by lipases, such as 1-O-phytanyl-β-D-riboside [β-Rib(Phyt)], where the covalent bond between the polar head is an ether, instead of an ester and because the polar head is not glycerol derived, but is derived of a sugar, such as a ribose.

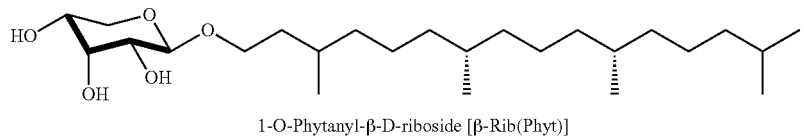

1-O-Phytanyl-β-D-riboside [β-Rib(Phyt)]

The replacement of the presently used polymer based overcoating of the subcutaneously implantable wired glucose oxidase glucose electrooxidizing anodes by a cubic phase lyotropic liquid crystal coating, doped with a two-chained lipids like 1,2-dioleoyl-sn-glycero-3-phosphate offers several advantages.

The LLC offers the advantage of manufacturability of reproducible glucose transport controlling membranes that provide the basis for ex-vivo pre-calibration of the sensors. The LLC film is applied by doctor blading. The process involves cutting a hole, similar in shape but larger than the wired enzyme coated sensing area, in a plastic spacer. The LLC is smeared on the entire surface, to fill the hole(s) and its excess is removed with a blade. The spacer with the hole is then lifted off, and the film is annealed in water or in humid air for 24 hours.

In addition, the LLC offers the advantage of mechanical strength. Because 1,2-dioleoyl-sn-glycero-3-phosphate, unlike monoolein, has two, not one, lipid chains, and because the bonding in the lyotropic liquid crystals is through hydrophobic bonds between the long chains, the 1,2-dioleoyl-sn-glycero-3-phosphate acts as a crosslinker of a plastic film, mechanically strengthening the cubic phase lyotropic liquid crystal. On our 5 mm diameter rotating electrodes the 1,2-dioleoyl-sn-glycero-3-phosphate-doped cubic phase lyotropic liquid crystal withstood, in a 24 hour test, the shear stress produced by 1000 rpm rotation, while the undoped cubic phase was instantaneously damaged. We expect that the cubic phase lyotropic liquid crystal coated on a polyester strip will easily withstand the shear stress of shooting the strip into the skin.

Also, the LLC offers the advantage of providing a nontoxic, bioinert surface. Because monoolein and 1,2-dioleoyl-sn-glycero-3-phosphateare, respectively, are blood and cell membrane constituents, the cubic phase lyotropic liquid crystal is expected to be bioinert, i.e. not likely to trigger blood coagulation or immune reaction.

Furthermore, the LLC also offers the advantage of providing an anionic interferent exclusion. The 1,2-dioleoyl-sn-glycero-3-phosphate made the walls of the 5-6 nm aqueous channels anionic. This increased the cation/anion permeability ratio and made the cubic phase lyotropic liquid crystal function as a cation exchange membrane.

Figure 12:
FIG. 12 shows the structures of 1-O-β-3,7,11,15-tetramethylhexadecyl-D-ribopyranoside abbreviated as β-Rib (Phyt)) and of vitamin E acetate, abbreviated as VitEA.
Figure 12:
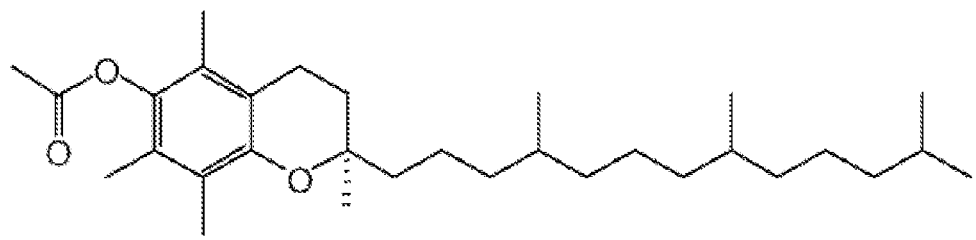

Monosubstituted glycolipids—lipids having sugar head-groups—have generally high Krafft temperatures, i.e. temperature at which they form LLC phases, because not are not only hydrophobically-bound, but also form hydrogen-bonds at their sugar head-groups. Here we disclose the synthesis of a new amphiphile, 1-O-β-(3,7,11,15-tetramethylhexadecyl)-D-ribopyranoside, abbreviated as β-Rib(Phyt), characterize its lyotropic properties, and engineer, by adding Vitamin E acetate (FIG. 12) an amphiphile forming in excess water an LLC cubic phase of which we form membranes controllably and reproducibly limiting the glucose-flux to the glucose-electrooxidizing "wired" glucose oxidase anode.

Chemicals and Materials.

The $CH_2Cl_2$ used in the following syntheses was dried with anhydrous $CaCl_2$, refluxed over $CaH_2$ for 1 h, then distilled. Phytol was purchased from Pfaltz & Bauer Inc (Waterbury, Conn.). 1-O-acetyl-2,3,5-tri-O-benzoyl-β-D-riboside, monoolein (1-oleoyl-rac-glycerol), Vitamin E acetate (96%) and α-tocopherol and bovine serum albumin, glutaraldehyde and catalase (bovine liver) were purchased from Sigma-Aldrich (St. Louis, Mo.). Phytantriol was purchased from TCI (Portland, Oreg.). The redox polymer (X-7) was a gift of Abbott Diabetes Care (Alameda, Calif.). PEGDGE (poly(ethylene glycol) (400) diglycidyl ether) was purchased from Polysciences (Warrington, Pa.). Glucose oxidase (from *A. niger*) was purchased from Fluka (St. Louis, Mo.). The silica gel (230-400 mesh) used for column chromatography was purchased from Fischer Chemicals (Pittsburgh, Pa.). The electrochemical measurements were performed in a pH 7.3 physiological buffer, containing 20 mM phosphate and 0.15 M NaCl, or in fetal calf serum from Biomeda (Foster City, Calif.). An antibiotic-antimycotic solution (Sigma-Aldrich, St. Louis, Mo.) was added to the serum to prevent growth of organisms.

Instrumental Analyses.

The 1H NMR spectra were obtained with a Varian Mercury-400 spectrometer in $CDCl_3$ containing $Si(CH_3)_4$ as internal standard. The mass spectra (ESI-MS) were recorded at low resolution with a Mariner (PerSeptive Biosystems Inc, Framingham, Mass.) mass spectrometer. The small angle X-ray structural analyses were performed using a Molecular Metrology Optics, (Northampton, Ma.) diffractometer, equipped with a Cu anode source (CuKαλ=1.5418 Å).

Syntheses.

The syntheses were carried out under dry conditions. The silica gel TLC plates (Fluka 60 F 254) were visually observed under UV light, or were made observable by charring with a 5% solution of sulfuric acid in ethanol, or by oxidation in a $KMnO_4$ solution.

Synthesis of 1-O-β-(3,7,11,15-tetramethylhexadecyl)-D-ribopyranoside (β-Rib(Phyt))

3,7,11,15-Tetramethyl-2-hexadecan-1-ol. 20 g (6.75 mmol) of phytol in 200 ml of ethanol was hydrogenated (1 atm $H_2$) by stirring with 2-3 g of Raney nickel for ~6 h at the ambient temperature, the hydrogenation monitored by TLC. It was stopped after immersion in a $KMnO_4$ solution no longer resulted in color in the TLC plate. After filtering the solution to remove the catalyst, the solvent was evaporated, and the residue was subjected to column chromatography on silica gel with hexane:ethyl acetate (3:1, v/v) as eluent, to yield the 3,7,11,15-tetramethyl-2-hexadecan-1-ol (yield 88%), a colorless oil, $R_f=0.36$ (hexane:ethyl acetate =3:1, v/v). $^1$H NMR (CDCl$_3$, δ, ppm): 0.84 (d, 6H, J=6.6 Hz), 0.86 (d, 6H, J=6.5 Hz), 0.89 (d, 3H, J=6.6 Hz), 1.00-1.40 (m, 21H), 1.52 (sept, 1H, J=6.5 Hz), 1.58 (m, 2H), 3.67 (m, 2H). 1-O-β-(3,7,11,15-Tetramethylhexadecyl)-2,3,5-tri-O-benzoyl-D-ribopyranoside. 1.5 g (2.98 mmol) of 1-O-acetyl-2,3,5-tri-O-benzoyl-β-D-riboside was dissolved in 30 mL dry CH$_2$Cl$_2$ and reacted with an equimolar amount of SnCl$_2$ at 0° C. The clear solution was stirred for 10 min at room temperature. An equimolar amount (0.88 g) of dihydrophytol was then added drop-wise and the homogenous solution was stirred for an additional 5 h, then poured into a saturated solution of NaHCO$_3$, from which the compound was extracted twice with 15-mL CH$_2$Cl$_2$. The extract was dried over Na$_2$SO$_4$ and the CH$_2$Cl$_2$ was evaporated in vacuo to give the crude glycoside (β-anomer) containing also the α-anomer and traces of 1-O-acetyl-2,3,5-tri-O-benzoyl-β-D-riboside and dihydrophytol. After column chromatography on silica gel, with hexane:ethyl acetate=3:1, v/v as eluent, a light-yellow oil containing 1-O-β-(3,7,11,15-tetramethylhexadecyl)-2,3,5-tri-O-benzoyl-D-ribopyranoside (62%) was obtained. $R_f=0.48$ (hexane:ethyl acetate=3:1, v/v). ESI (+) m/z 765 [M+Na]$^+$, calculated for C$_{46}$H$_{62}$O$_8$, 742 [M]$^+$. $^1$H NMR (CDCl$_3$, δ, ppm): 0.8-0.87 (15H, CH$_3$ in phytanyl chain); 0.96-1.39 (m, 22H, 9 CH$_2$ and 4 CH in phytanyl chain); 1.53 (m, 2H, —CH$_2$—CH$_2$—O— in phytanyl chain); 3.44-3.53 (m, 1H, —CH$_2$—CH$_2$—O— in phytanyl chain); 3.77-3.84 (m, 1H, —CH$_2$—CH$_2$—O— in phytanyl chain); 4.52 (dd, 1H, H-5b); 4.65-4.74 (m, 2H, H-4, H-5a); 5.25 (d, 1H, H–1); 5.66 (d, 1H, H-2); 5.87 (dd, 1H, H-3); 7.25-8.11 (m, 15H, H—Ar). 1-O-β-(3,7,11,15-tetramethylhexadecyl)-D-ribopyranoside (β-Rib(Phyt)), I. The 1-O-β-(3,7,11,15-tetramethylhexadecyl)-2,3,5-tri-O-benzoyl-D-ribopyranoside 0.85 g (1.14 mmol) was de-benzoylated in dry CH$_3$OH (30 mL) containing a catalytic amount of CH$_3$ONa. After overnight reaction at ambient temperature the CH$_3$OH was evaporated in vacuo and the mixture was separated by column chromatography (silica gel, chloroform:methanol=8:1, v/v) and pure I was obtained. (43% yield; colorless oil; $R_f=0.36$ (chloroform:methanol=8:1, v/v)). ESI (+) m/z 453 [M+Na]$^+$, calculated for C$_{25}$H$_{50}$O$_5$, 430 [M]$^+$. $^1$H NMR (CDCl$_3$, δ, ppm): 0.84-0.88 (15H, CH$_3$ in phytanyl chain); 1.02-1.60 (m, 24H, 10 CH$_2$ and 4 CH in phytanyl chain); 3.05-3.81 (m, 3H, H-4, H-5b, —CH$_2$— CH$_2$O— in phytanyl chain); 4.03-4.08 (m, 2H, H-2, H-5a); 4.33 (dd, 1H, H-3); 4.94 (s, 1H, H–1, β-anomer); 3.41-3.54 (m, 3H, 2-OH, —CH$_2$—CH$_2$—O— in phytanyl chain); 1.61 (br, 1H, 1-OH).

Preparation of Wired Glucose Oxidase Anodes.

Rotating vitreous carbon electrodes (0.196 cm$^2$, Pine Instruments, Raleigh, N.C.) were polished using 0.05 μm alumina, rinsed, sonicated for 10 min and dried, then made hydrophilic by exposure to O$_2$ plasma (10 min, 1 Torr O$_2$). 9-μL aliquots of a mixture of 11.9 μL of glucose oxidase solution in water (10 mg/ml), 14.4 μL of the wiring redox polymer (X-7) solution (10 mg/mL) in water, 8.8 μL of PEGDGE in water (10 mg/mL) and 40 μL of water were applied by pipetting onto the electrode surface. Total bio-electrocatalyst loading was 215 μg/cm$^2$, of which the wiring redox polymer was 90 μg/cm$^2$. The film left after the water evaporated formed was cured overnight at room temperature.

Preparation of the LLC Cubic Phases.

The β-Rib(Phyt)/Vitamin E acetate/H$_2$O LLC was prepared by adding 1 to 10 weight % of Vitamin E acetate (VitEA) to the β-Rib(Phyt)) in an Eppendorf tube. The mixture was centrifuged in the closed tube for 5 minutes in a 5412 Eppendorf centrifuge at 15,000 G, twice the weight of the organic matter of water was added, and the mixture was vortexed and centrifuged several times until a low viscosity, homogenous emulsion was obtained. More water was then added to 20× the organic matter and the mixture was again centrifuged to produce the LLC cubic phase used for coating the electrodes, comprising 7 weight % VitEA in β-Rib(Phyt).

The LLC cubic phases were prepared at least 48 hrs before use. Under a polarizing microscope (Boreal Laboratories, 100×, St. Catharines, Ontario, Canada), their films were dark and featureless, except at their rim (where water was lost by evaporation). The β-Rib(Phyt)/Vitamin E acetate/H$_2$O LLC cubic phase was stable for at least six months in a tightly capped vial.

Application of LLC Cubic Phases Layers to the Electrodes by Doctor-Blading.

0.1, 0.2 and 0.4 mm nominal thickness plastic (polyester) or stainless steel spacers with 6 mm holes were placed on the polished electrocatalyst-coated or uncoated vitreous carbon electrodes. Their holes were filled with the LLC using a pipette tip, the excess LLC was removed with a blade and the spacers were lifted off. The weights of the LLC films were 2-2.5 mg at 0.1 mm nominal spacer thickness, 5.5-6.0 mg at 0.2 mm nominal thickness, and 10.0 to 12.5 mg at 0.4 mm nominal thickness.

Phase Diagrams.

The phase diagrams of the β-Rib(Phyt)-containing compositions were obtained by placing the 10 mg LLC samples in excess water and observing the appearance or disappearance of birefringence between crossed polarizers while the temperature was slowly raised.

Electrochemical Instrumentation and Cell.

The electrodes were rotated using a Pine Instruments (Grove, Pa.) rotator. A Model CHI832 potentiostat (CH-Instruments, Austin, Tex.) was used. The three-electrode cell, with a platinum wire counter electrode and a Ag/AgCl (3 M NaCl) reference electrode was maintained at 37.5° C. by an isothermal circulator (Fisher Scientific, Pittsburgh, Pa.). The reported potentials are versus this reference.

Example 8

Phase Diagram of the β-Rib(Phyt)/VitEA/H$_2$O System

The 1-O-β-(3,7,11,15-tetramethylhexadecyl)-D-ribopyranoside amphiphile was synthesized and its phase diagram was tailored by adding vitamin E acetate, to form a cubic phase. The phase was stable through the 20° C.-90° C. temperature range in excess of water and had the desired glucose-transport characteristics.

Figure 13:
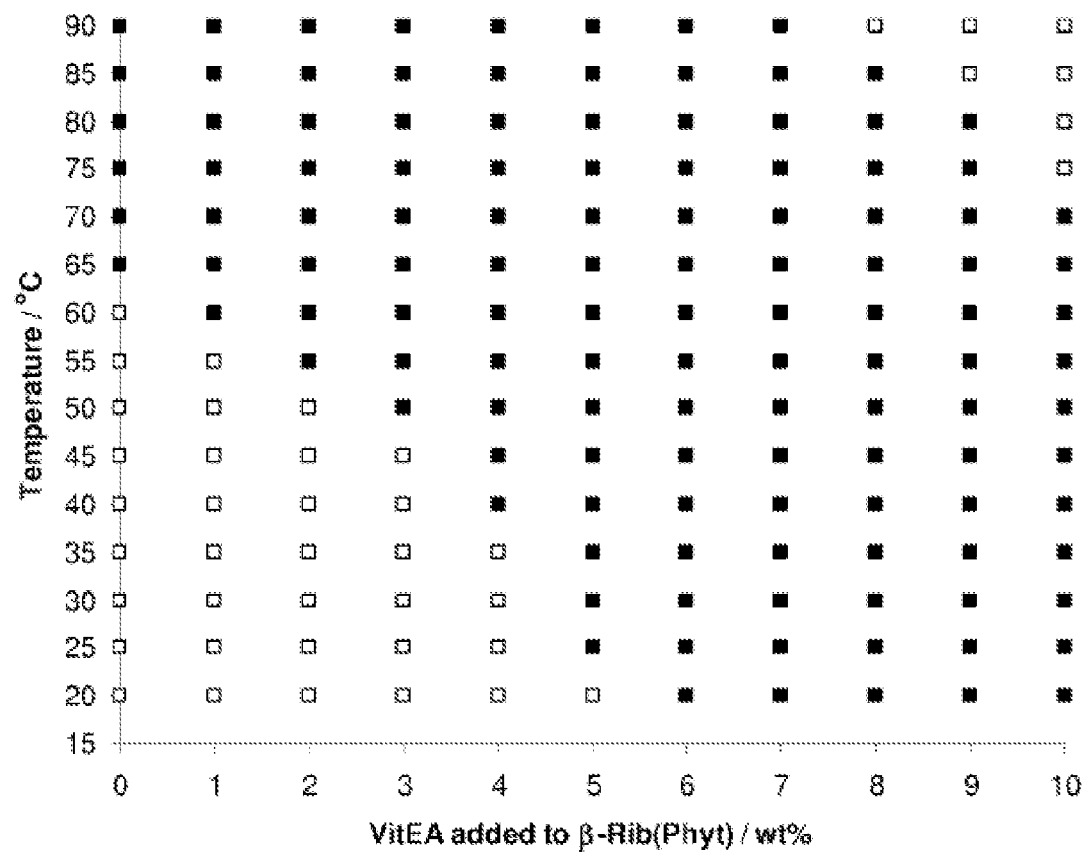
FIG. 13 shows the effect of adding Vitamin E acetate to β-Rib(Phyt)-H$_2$O on the phase formed at 20× water-excess. Hollow squares—birefringent; solid squares—isotropic, cubic phase LLC.

The β-Rib(Phyt)-H$_2$O system is non-isotropic at ambient temperature, but is cubic-isotropic above 60-65° C. It remains cubic-isotropic at temperatures also above 90° C., the upper limit of this study. (FIG. 13) Because VitEA suppresses the phase transition temperature of the phytantriol-H$_2$O system, and because β-Rib(Phyt) and phytantriol contain the same hydrophobic chain, VitEA was used to suppress the phase transition temperature of the β-Rib(Phyt)-H$_2$O (95 wt. % water) system. As seen in FIG. 13, VitEA was not only effective in suppressing the phase transition temperature of β-Rib(Phyt)-H$_2$O but it allowed accurate tailoring of the temperature range through which the phase was cubic-isotropic. At 5.5 wt % VitEA the system became viscous, isotropic i.e. non-birefringent at ambient temperature. The upper temperature limit of stability of the isotropic phase was also lowered by VitEA. At 8 weight % VitEA, birefringence was observed at 90° C. and at 10% weight % VitEA, already at 75° C.

β-Rib(Phyt) and β-Xyl(Phyt) are epimers, differing only in the stereochemistry of their C-3 carbon of their sugars. The difference causes, nevertheless, an almost 40° C. upshift of the temperature at which the cubic phase is formed, attributed to the strong hydrogen-bonding of the aligned Rib-head-groups. Incorporation of increasing amounts of VitEA perturbs the alignment and lessens the hydrogen bonding. This is the case also in dry samples of β-Rib(Phyt), which become less viscous when VitEA is added.

Example 9

Figure 14:
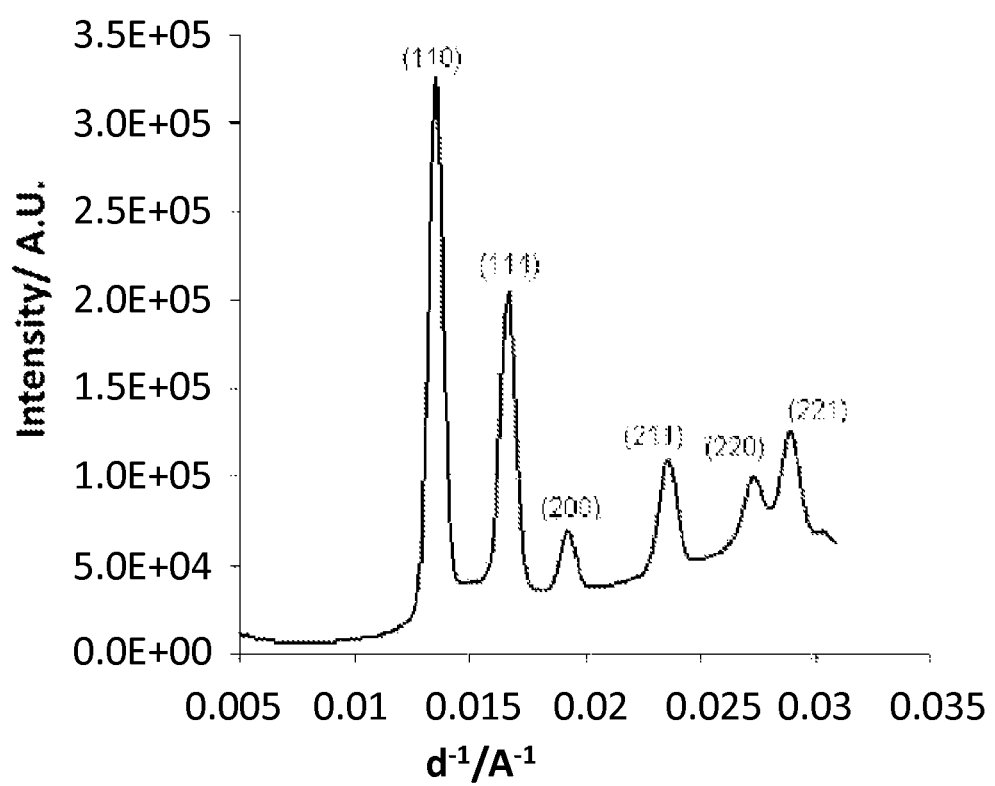
FIG. 14 shows SAXS (small angle X-ray scattering) profiles. Top: β-Rib(Phyt)/VitEA (7 wt %)/H$_2$O, 95 wt % H$_2$O. Center: MO/H$_2$O, 95 wt % H$_2$O. Bottom: MO/H$_2$O, 42 wt % H$_2$O. Left, 20° C.; right, 38° C.
Figure 14:
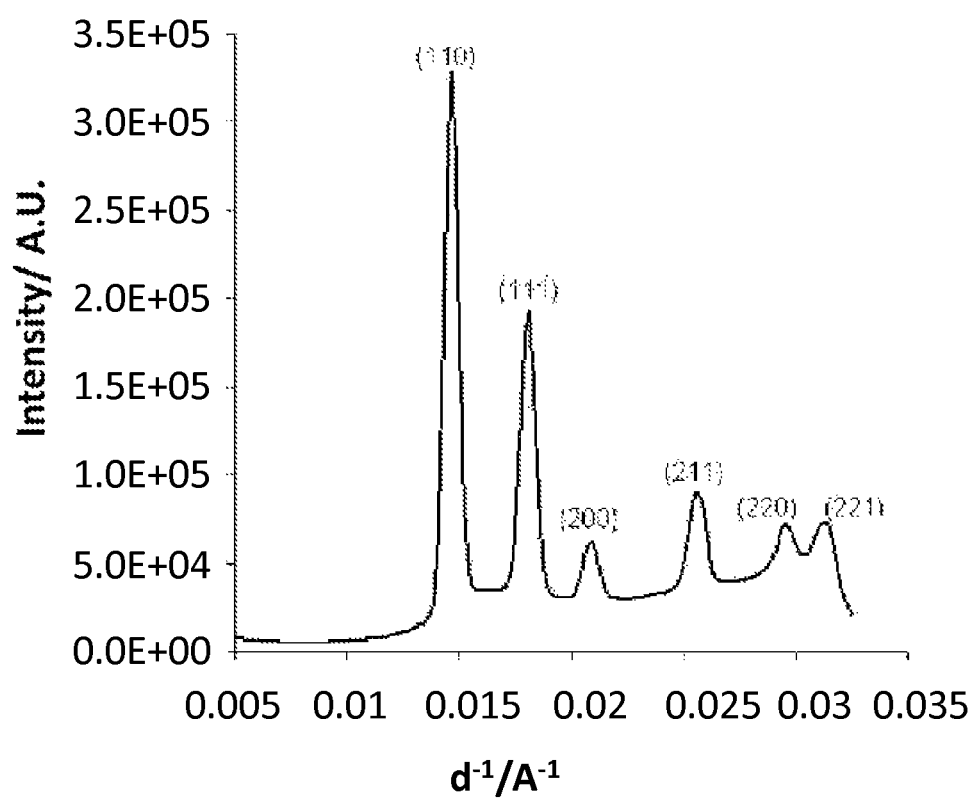
Figure 14:
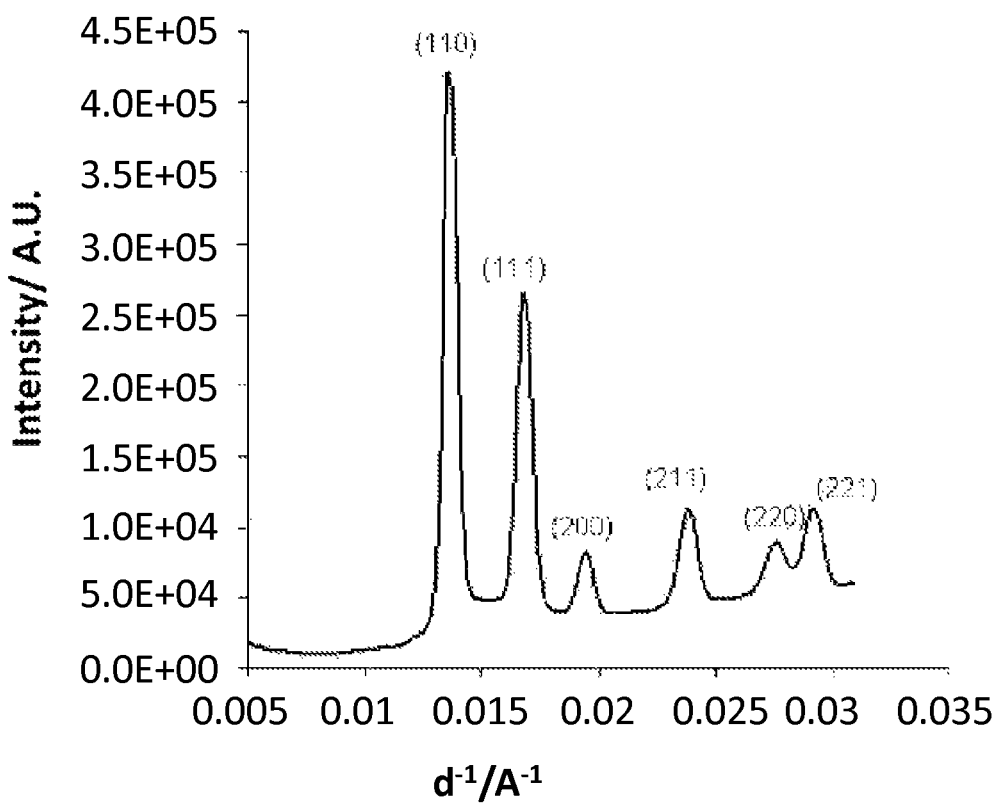
Figure 14:
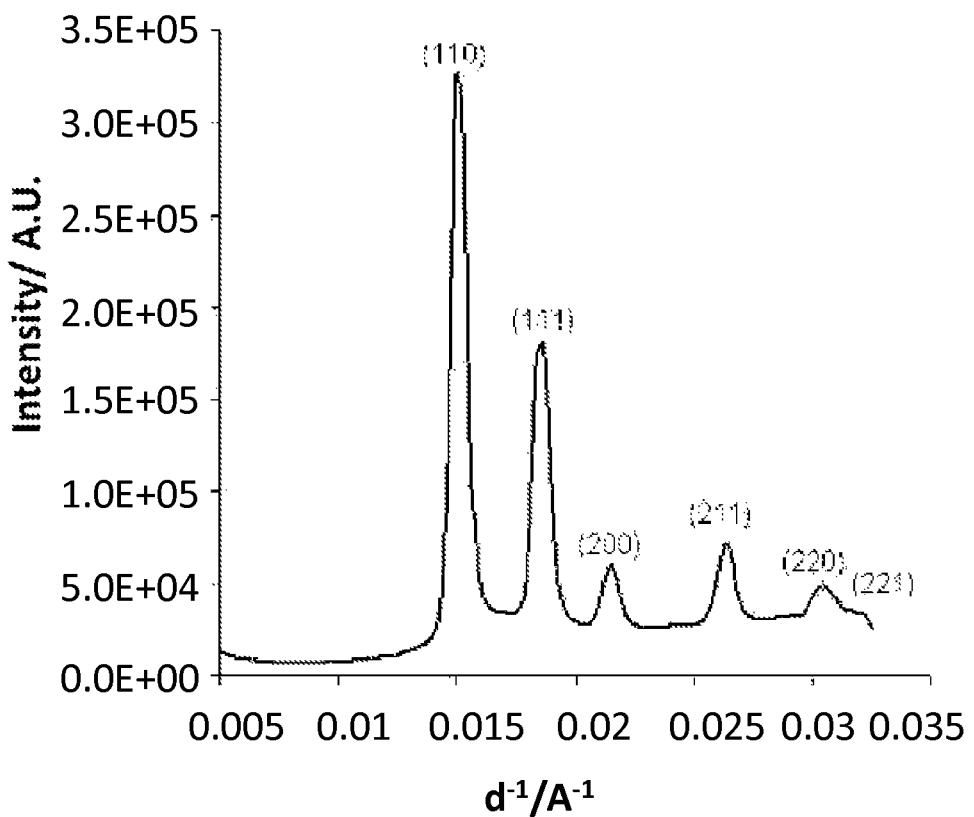
Figure 14:
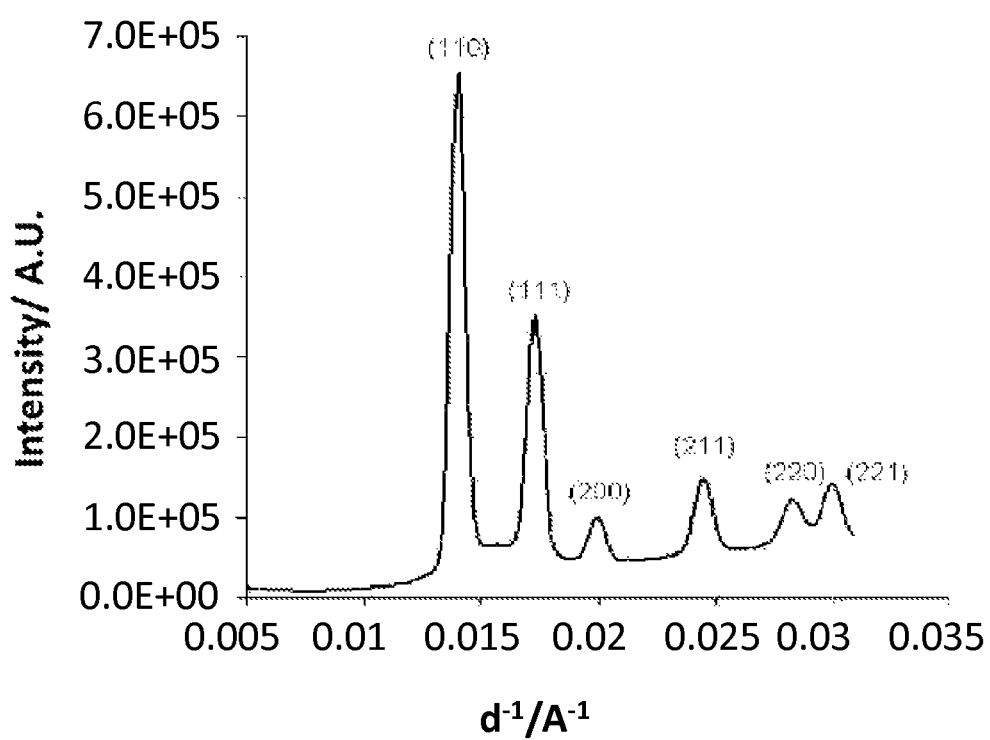
Figure 14:
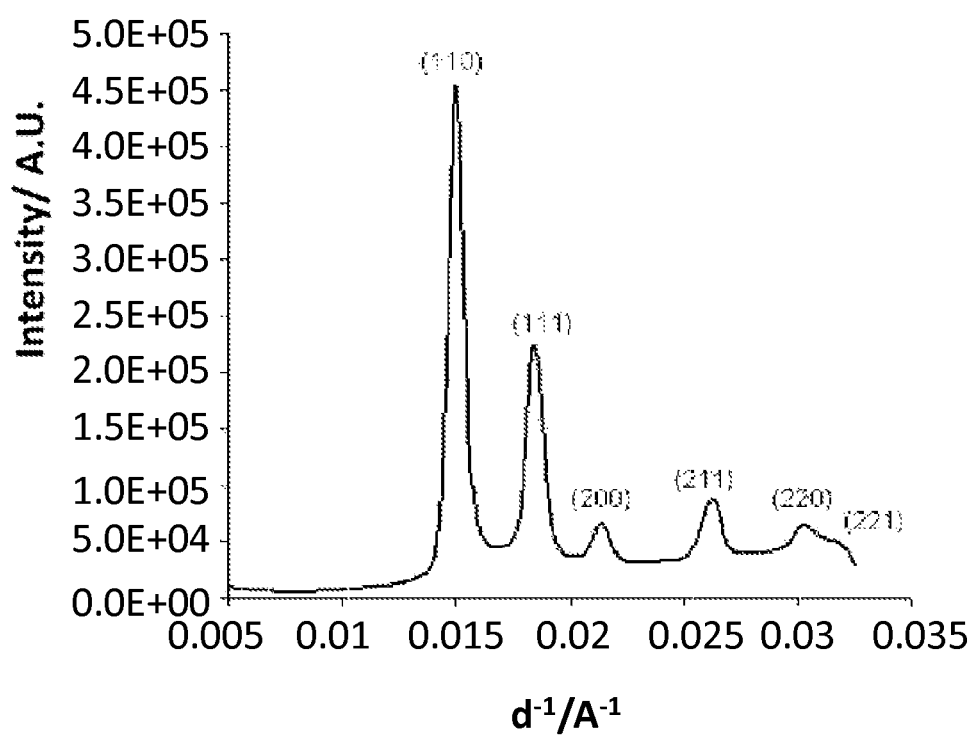

Small Angle X-Ray Analysis of the Structure of the β-Rib(Phyt)-7% Wt. Of VitEA-H$_2$O (95%) Phase Because of the 20° C.-90° C. stability range of the phase, it was selected for structural analysis by small-angle X-ray scattering (SAXS). FIG. 14 shows its 20° C. and 38° C. SAXS scattering profiles in the presence a large excess of water, 5 wt. % amphiphile, 95 wt. % water. Scattering data were obtained also for the monoolein/H$_2$O reference system at 58 and 5 weight % amphiphile content. At 20° C. the β-Rib(Phyt)-VitEA-H$_2$O (95%) system formed a diamond type cubic phase of the Pn3m space group, similar to the space group of the classical monoolein-system. Up to sixth order (110), (111), (200), (211), (220), (221) diffraction peaks were seen at ambient temperature. The lattice constant for the β-Rib(Phyt)-VitEA-H$_2$O (95%) system was similar to that of the 5 weight % monoolein cubic phase (Table 6) and was slightly larger than that of the monoolein system at low hydration (58 weight % lipid content). The systems retained their cubic Pn3m structure at 38° C., where their lattice parameters were smaller than at 20° C. (Table 6).

TABLE 6

Lattice constants at 20° C. and 38° C.

| | Lattice constant at 20° C. [Å] | Lattice constant at 38° C. [Å] |
|---|---|---|
| β-Rib(Phyt)-VitEA (7 wt %)H$_2$O, 95% H$_2$O | 103.9 | 95.8 |
| MO/H$_2$O, 95% H$_2$O | 102.8 | 93.1 |
| MO/H$_2$O, 42% H$_2$O | 100.1 | 93.5 |

Example 10

Stability of the β-Rib(Phyt)-VitEA-Water LLC Cubic Phase Film on Electrodes

The films are stable on vitreous carbon electrodes coated with a 0.1 mm thick β-Rib(Phyt)/VitEA (7 wt %)/H$_2$O film in 0.15 M NaCl, pH 7.3, 0.02 M phosphate buffer, the electrodes poised at 0.15 V vs. Ag/AgCl. H$_2$O$_2$, is generated in glucose oxidase-catalyzed O$_2$-oxidation of glucose, rapidly damaged the monoolein:H$_2$O LLC, the β-Rib(Phyt)/VitEA (7 wt %)/H$_2$O LLC persisted in 2 mM of H$_2$O$_2$ for 24 hrs. The films, which are stable at neutral pH, are unstable in strong acids because of hydrolysis of the β-glycoside bond of β-Rib(Phyt). Although VitEA is hydrolyzed in both acids and bases, partial hydrolysis does not de-stabilize the cubic phase because β-Rib(Phyt) forms the phase at ambient temperature not only with VitEA, but also with α-tocopherol, the alcohol produced in its hydrolysis.

In addition, the LLC also offers the advantage of enabling a lesser temperature dependence of the current, lessening the need to monitor and correct for variations in temperature and making it feasible to use sensors that are implanted less deeply than 0.5 cm, possibly allowing use of 0.4 cm long (deep) and even 0.3 mm long (deep) subcutaneously implanted sensors.

A measure of the usefulness of an LLC glucose-transport limiting over-layers is shape and size-retention upon dehydration during storage and re-hydration upon implantation in tissue. When 0.1 mm thick, sharp-cornered, 4 mm×4 mm squares of cubic-phase monoolein-H$_2$O, phytantriol-H$_2$O and β-Rib(Phyt)-7 wt. % VitEA-H$_2$O films were formed by doctor-blading on polyester sheets and dried for 2 h under ambient conditions, the phytantriol films turned into liquid drops, while the monoolein and the Rib(Phyt)-7 wt. % VitEA films retained their size and shape. When re-hydrated with a 150 μL drop of distilled water, both the monoolein-H$_2$O and the β-Rib(Phyt)-7 wt. % VitEA-H$_2$O films re-assumed their cubic-isotropic structure, but the monoolein-H$_2$O changed its shape and size. Only the β-Rib(Phyt)-7 wt. % VitEA-H$_2$O film retained its original size and shape. Nevertheless, when it was fully dehydrated by overnight storage in vacuo in a desiccator over P$_2$O$_5$, the β-Rib(Phyt)-7 wt. % VitEA film also turned into a liquid drop, showing that a some water is necessary for shape and size retention. The 0.1 thick mm sharp-cornered 4 mm×4 mm squares of β-Rib(Phyt)-7 wt. % VitEA-H$_2$O did not migrate measurably on polyester sheets in a week under ambient conditions. The rehydration times for full recovery of the cubic LLC phases of dried amphiphilic precursor films, i.e. complete disappearance of birefringence between crossed polarizers, were 1.5 min for monoolein-H$_2$O, 5.0 min for phytantriol-H$_2$O and 8.0 min for β-Rib(Phyt)-VitEA (7 wt. %)-H$_2$O.

Example 11

Figure 15:
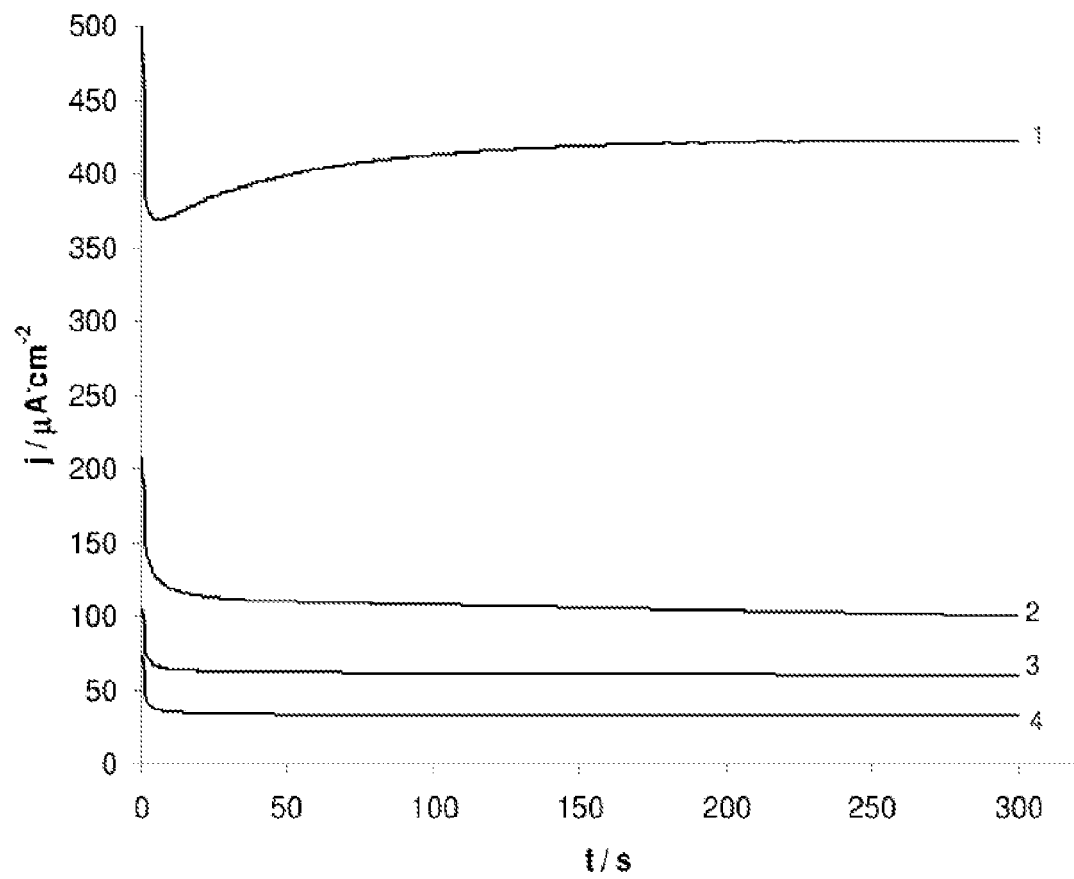
FIG. 15 shows glucose electrooxidation current densities of at different β-Rib(Phyt)-7 wt. % VitEA-H$_2$O LLC film thicknesses: (1) 0 mm; (2) 0.1 mm; (3) 0.2 mm; (4) 0.4 mm. 5 mm diameter vitreous carbon electrodes coated with wired glucose oxidase rotating at 100 rpm poised at 0.15 V vs. Ag/AgCl; 50 mM glucose in deoxygenated 0.15 M NaCl pH 7.4 0.02 M phosphate buffer; 37.5° C.
Figure 16:
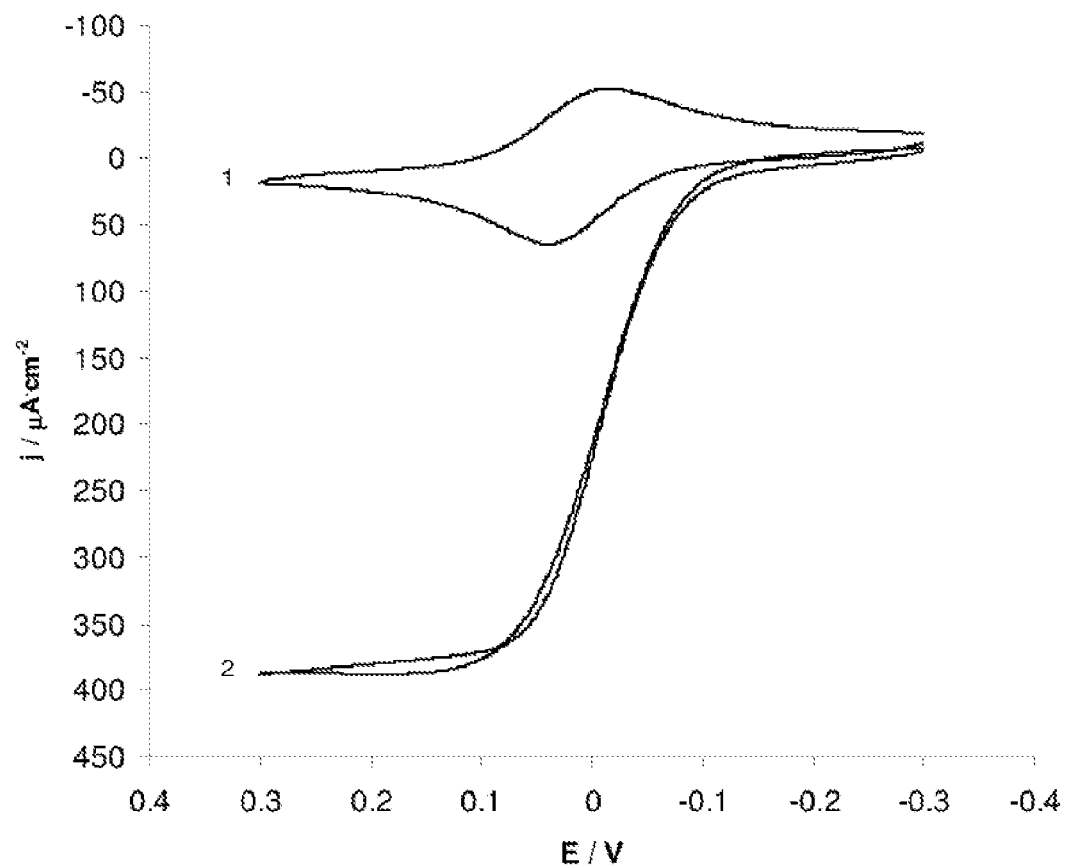
FIG. 16 shows cyclic voltammograms (1) without glucose; (2) for 50 mM glucose. 5 mm diameter vitreous carbon electrodes coated with wired glucose oxidase rotating at 100 rpm poised at 0.15 V vs. Ag/AgCl; 50 mM glucose in deoxygenated 0.15 M NaCl. pH 7.4 0.02 M phosphate buffer; 37.5° C.
Figure 17:
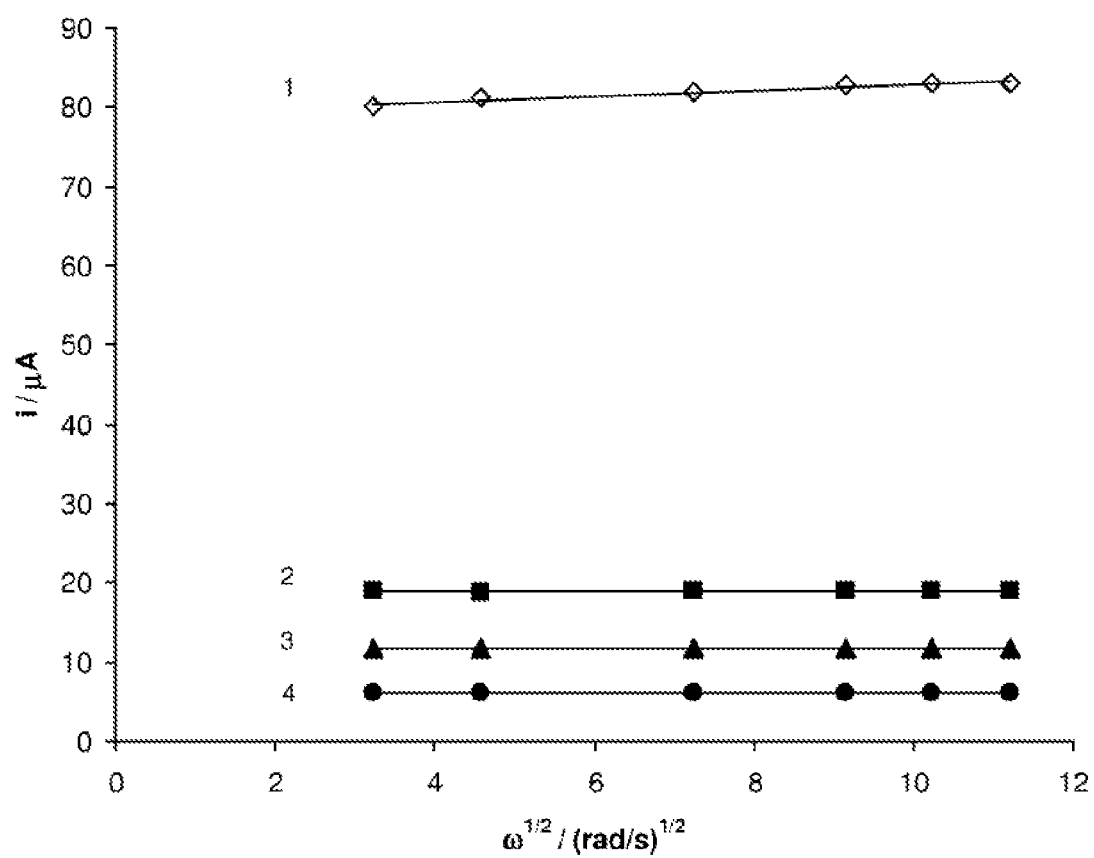
FIG. 17 shows Levich plots of the electrodes of FIG. 15. Conditions as in FIG. 15.

Dependence of the Glucose Electrooxidation Current on the β-Rib(Phyt)-7 wt. % VitEA-H$_2$O Cubic-Phase LLC Film Thickness FIG. 15 shows that the β-Rib(Phyt)-7 wt. % VitEA-H$_2$O film reduces the glucose electrooxidation current, and that the thicker the film is, the smaller is the current. The inverse of the current increases approximately linearly with the current. As seen in FIG. 16, the current reaches its plateau at 0.1 V vs. Ag/AgCl. The Levich plots of FIG. 17 confirm that the angular velocity of the rotating LLC coated electrodes, i.e. the solution-phase glucose transport to these electrodes, does not affect the current, the current depending on the glucose transport through the LLC film, not to it.

Figure 18:
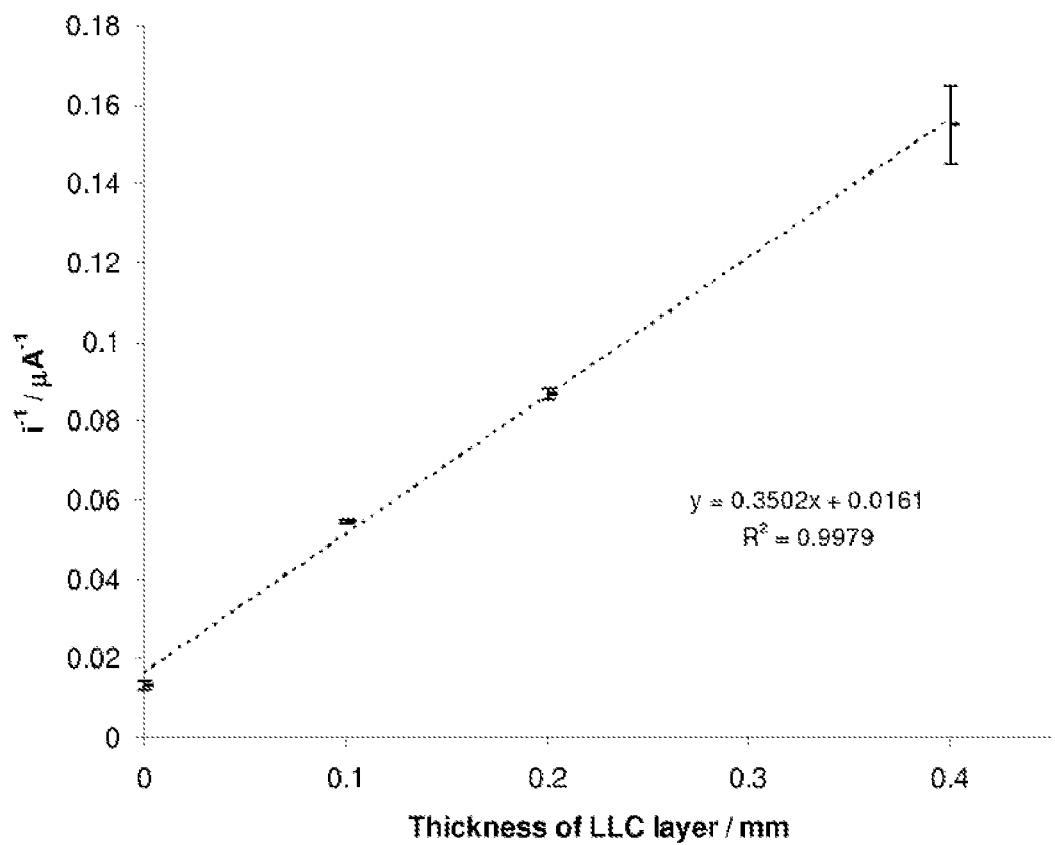
FIG. 18 shows a plot of the reciprocal of the current vs. the thickness of the LLC layer. Each data point is for two electrodes prepared at different times. Conditions as in FIG. 15.

FIG. 18 shows that the inverse of the glucose flux, i.e. the inverse of the current, increases linearly with the thickness of the membrane, implying that the current increases with the inverse of the LLC film thickness. The fit of data at all thicknesses and their tight reproducibility in triplicate experiments suggest that the films could be reproducibly manufactured.

Example 12

Calibration Curves in Deoxygenated and Aerated Solutions

Figure 19:
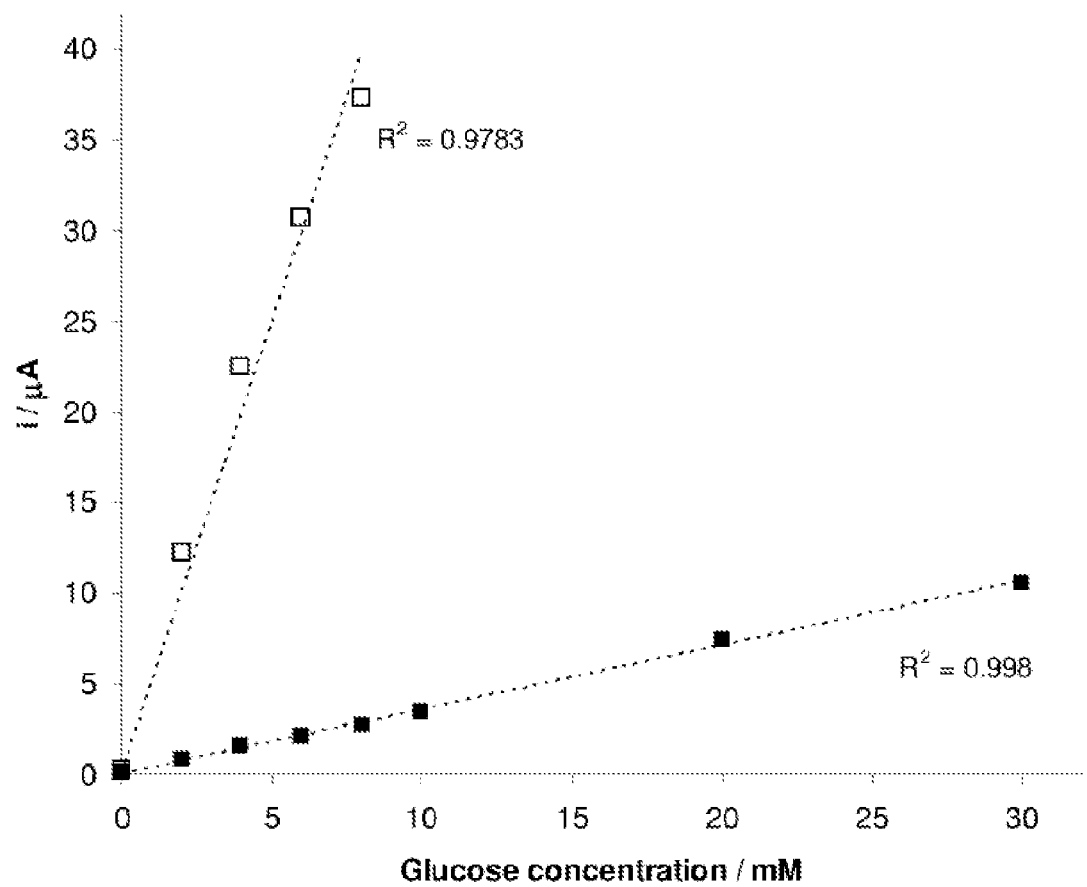
FIG. 19 shows the glucose concentration dependence of the current after 10 min equilibration in oxygenated solutions. Hollow squares, wired glucose oxidase electrode without the LLC. Solid squares, coated with 0.1 mm thick β-Rib(Phyt)-7 wt. % VitEA-H$_2$O LLC. Inset—same for a deoxygenated solution. Other conditions as in FIG. 15.
Figure 19:
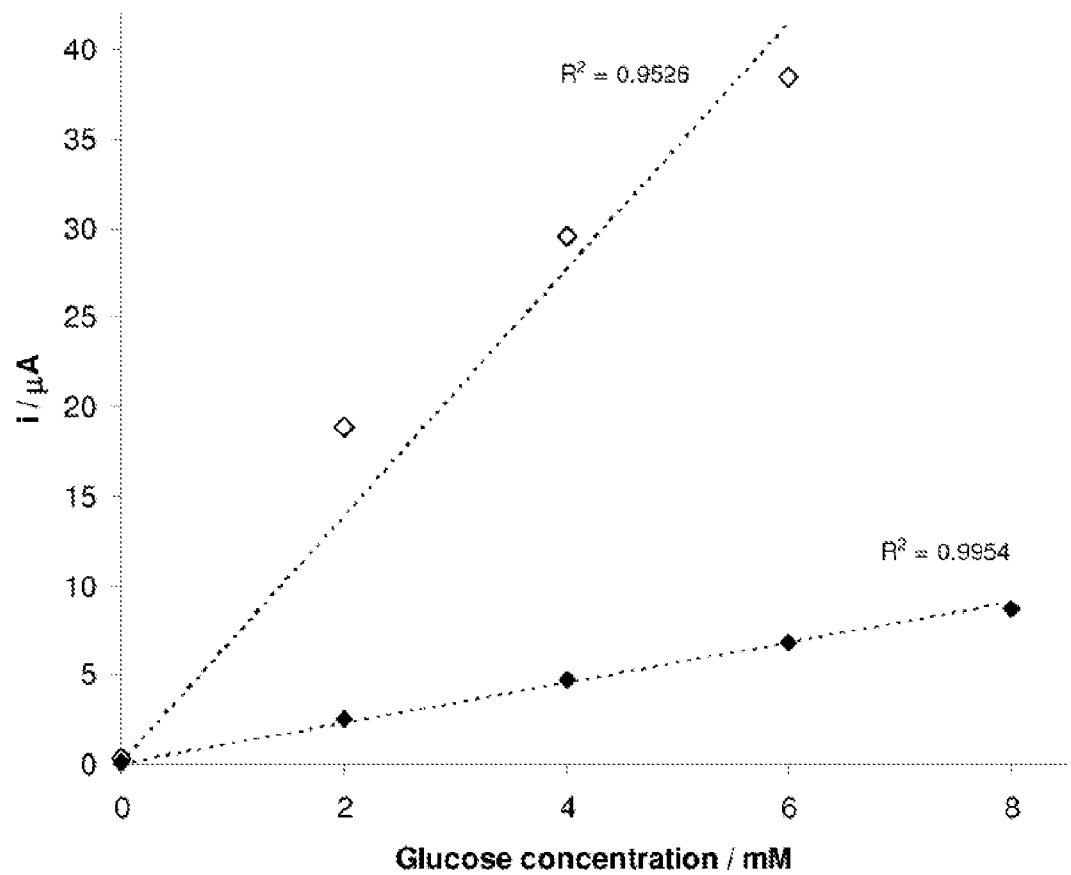
Figure 20:
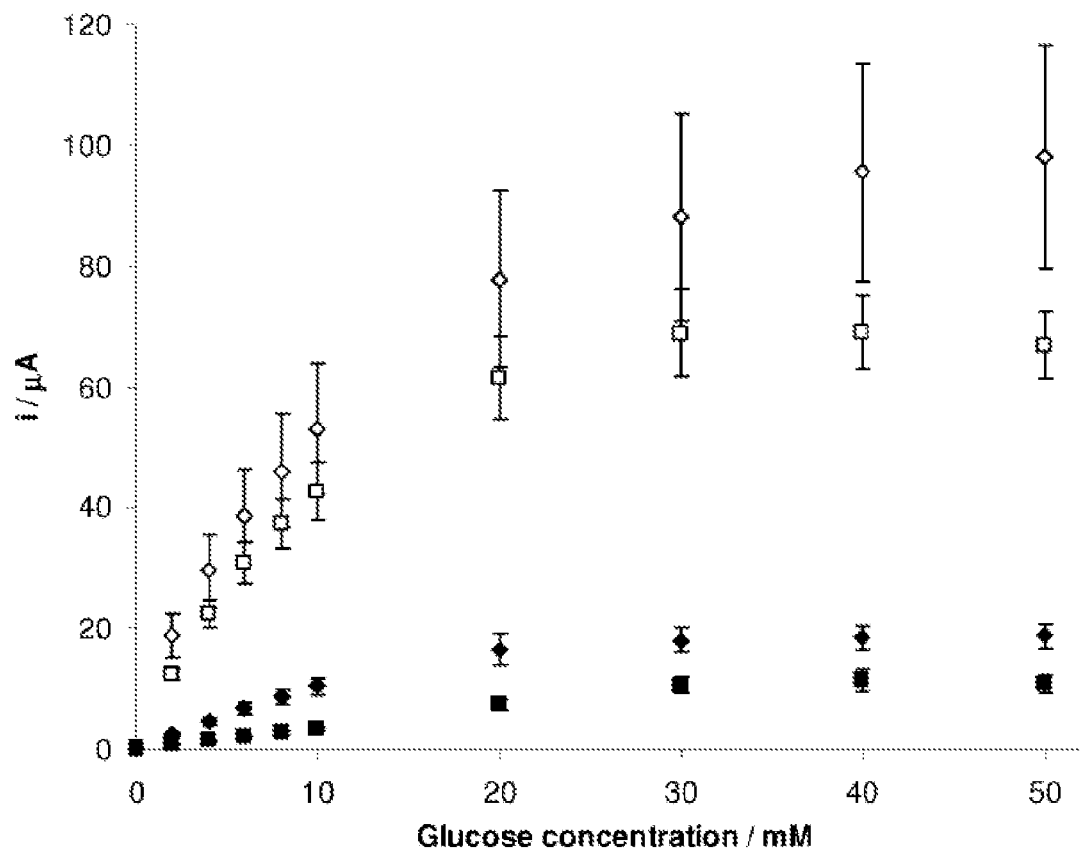
FIG. 20 shows the glucose concentration dependence of the current after 10 min equilibration in de-oxygenated and aerated solutions. Hollow rhombs: without the LLC film; deoxygenated solution; Hollow squares: electrode without the LLC, aerated solution; solid rhombs: coated with 0.1 mm thick β-Rib(Phyt)-7 wt. % VitEA-H$_2$O LLC, deoxygenated solution; solid squares: with 0.1 mm thick β-Rib(Phyt)-7 wt. % VitEA-H$_2$O LLC, aerated solution.

As seen in FIG. 19, the β-Rib(Phyt)-7 wt. % VitEA-H$_2$O cubic-phase LLC film limits the diffusion of glucose and assures that all the glucose-influx is reacted even at the highest glucose concentration of encountered in diabetes, about 30 mM Like the now used polymer films it extends the range through which the current increases linearly with the glucose concentration. Nevertheless, because $O_2$ is not only water-soluble, but is even more soluble in lipids and other amphiphiles, it permeates rapidly to the wired glucose oxidase electrocatalyst and a substantial fraction of the electrons generated when glucose is oxidized to gluconolactone reacts with $O_2$ rather than being collected by the glucose-electrooxidizing anode. Hence, the glucose-electrooxidation current is reduced by dissolved $O_2$. (FIGS. 19 and 20) At 50 mM glucose concentration, it is lower in an aerated solution by about 32% than it is in a deoxygenated solution. When the same electrode is shielded by a 0.1 mm thick β-Rib(Phyt)-7 wt. % VitEA-$H_2O$ film 43% of the current is lost. With the electrodes rotated to enhance $O_2$-transport and with the glucose-concentration kept low, so as to increase the $O_2$/glucose concentration ratio, the loss of current to $O_2$ is severe. While the sensitivity of the electrode without the LLC drops upon aeration by 28%, from 35.2 $\mu A \cdot mM^{-1} \cdot cm^{-2}$ to 25.4 $\mu A \cdot mM^{-1} \cdot cm^{-2}$, it drops by 68% from 5.7 $\mu A \cdot mM^{-1} \cdot cm^{-2}$ to 1.8 $\mu A \cdot mM^{-1} \cdot cm^{-2}$ when coated with the 0.1 mm thick β-Rib(Phyt)-7 wt. % VitEA-$H_2O$ cubic-phase.

Example 13

Activation Energy of the LLC Covered Glucose Oxidase Anode

Figure 21:
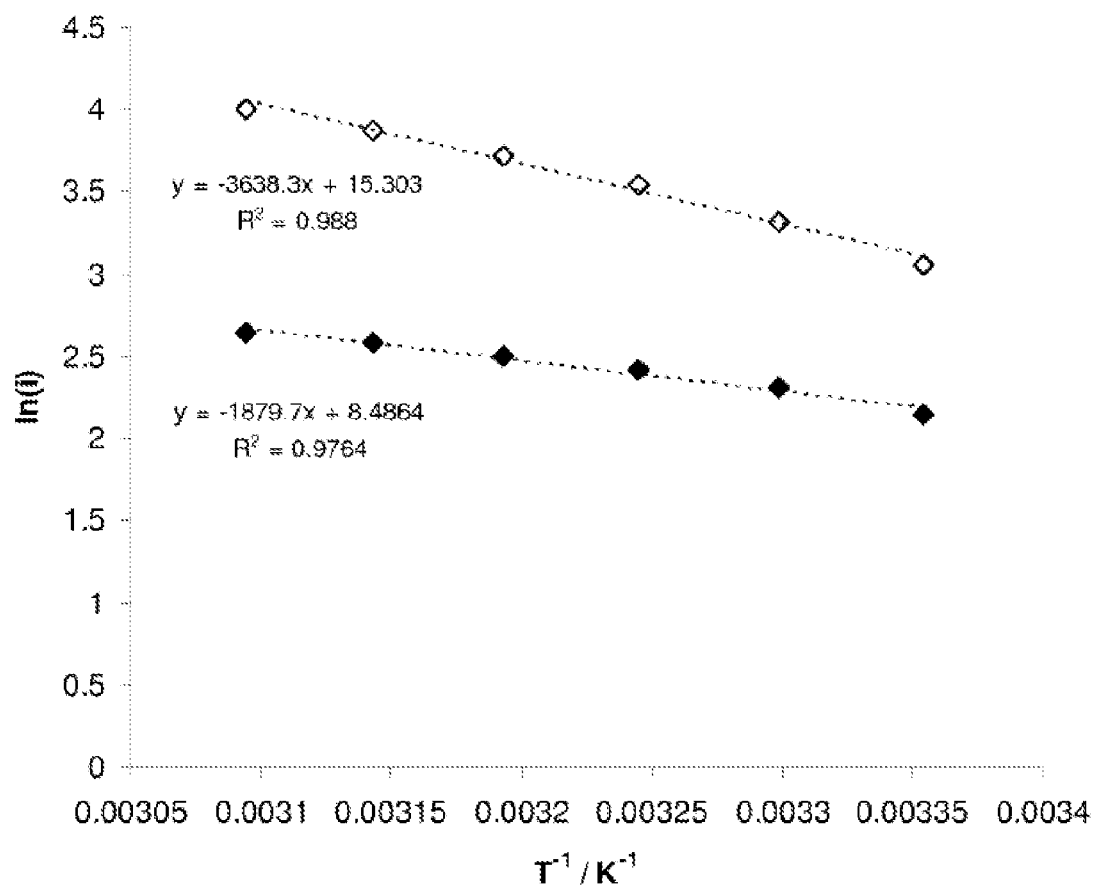
FIG. 21 shows Arrhenius plots for the glucose-electrooxidation current in de-oxygenated solutions. Conditions as in FIG. 15. Hollow rhombs without, solid rhombs with a 0.1 mm thick β-Rib(Phyt)-7 wt. % VitEA —$H_2O$ LLC membrane.

FIG. 21 shows Arrhenius plots for wired glucose oxidase anodes, with and without the 0.1 mm thick β-Rib(Phyt)-7 wt. % VitEA-$H_2O$ cubic-phase coatings. When the rate, i.e. the current is controlled by the electrode kinetics, the activation energy is 30.3 kJ/mol. When it is controlled by the permeation of glucose through the LLC, the activation energy is halved, dropping to 15.6 kJ/mol. The lesser dependence of the current on temperature facilitates calibration and use of the intended subcutaneously implanted sensors.

Example 14

Stability Under Shear Stress

Figure 22:
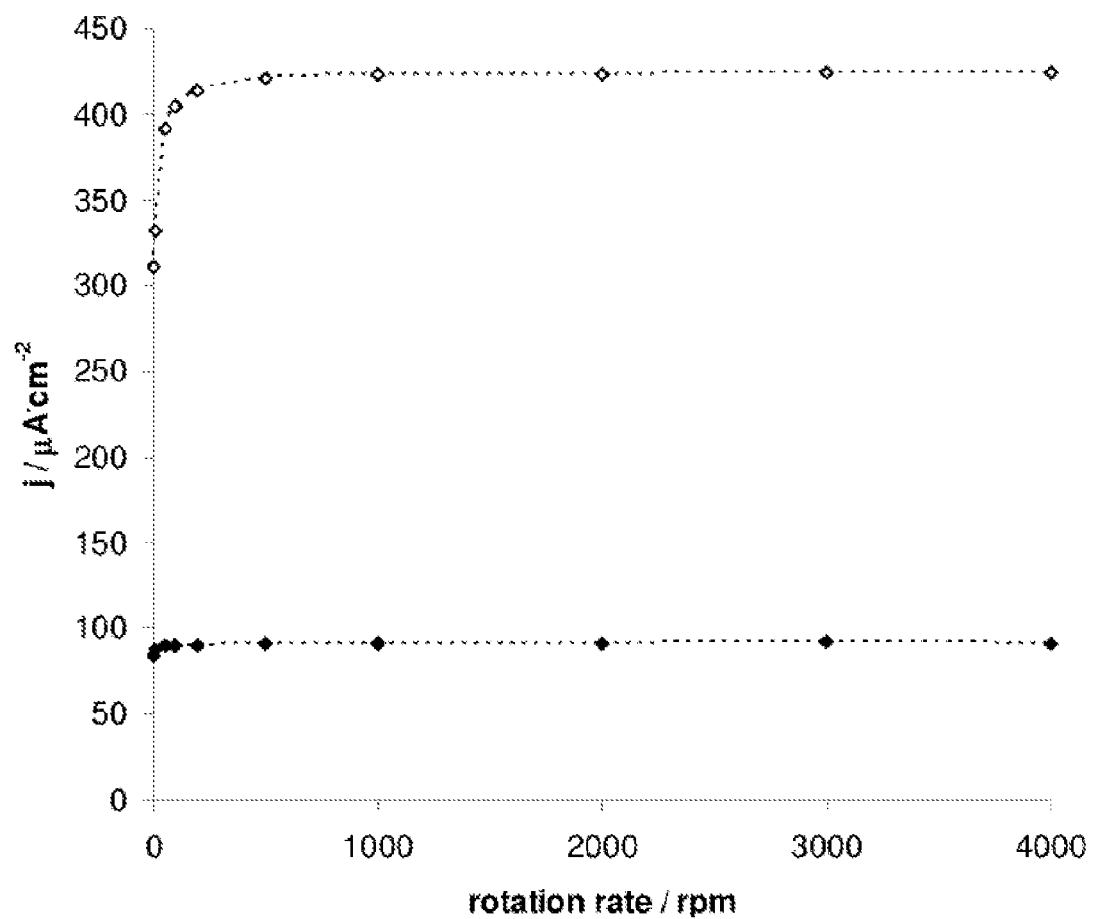
FIG. 22 shows shear-strengths of films of the wired glucose oxidase electrocatalyst and of the electrocatalyst overcoated with the 0.1 mm thick β-Rib(Phyt)-7 wt. % VitEA-$H_2O$ LLC. The figure shows that both withstand the 1 N $m^{-2}$ maximal shear stress acting on a 5 mm diameter electrodes rotating at 4000 rpm. Conditions as in FIG. 15; data taken after 10 min of equilibration. Hollow rhombs— without LLC, solid rhombs—sensor with the LLC.

Upon its subcutaneous insertion the sensor is sheared and when in a contracting-expanding tissue, such as muscle, it is repeatedly sheared. To investigate the persistence of the β-Rib(Phyt)-7 wt. % VitEA-$H_2O$ films under shear stress, steady state current densities were measured for 5 mm diameter electrodes rotating at angular velocities up to 4000 rpm, where the maximum shear stress is about 1 N $m^{-2}$. FIG. 22 shows that the current density of electrodes did not decrease because of shearing-off of their bioelectrocatalyst and that the current density of the 0.1 mm thick β-Rib(Phyt)-7 wt. % VitEA-$H_2O$ film coated electrodes did not increase because of shearing off of their glucose flux-limiting film.

Example 15

Response Time of the Glucose Sensor

Figure 23:
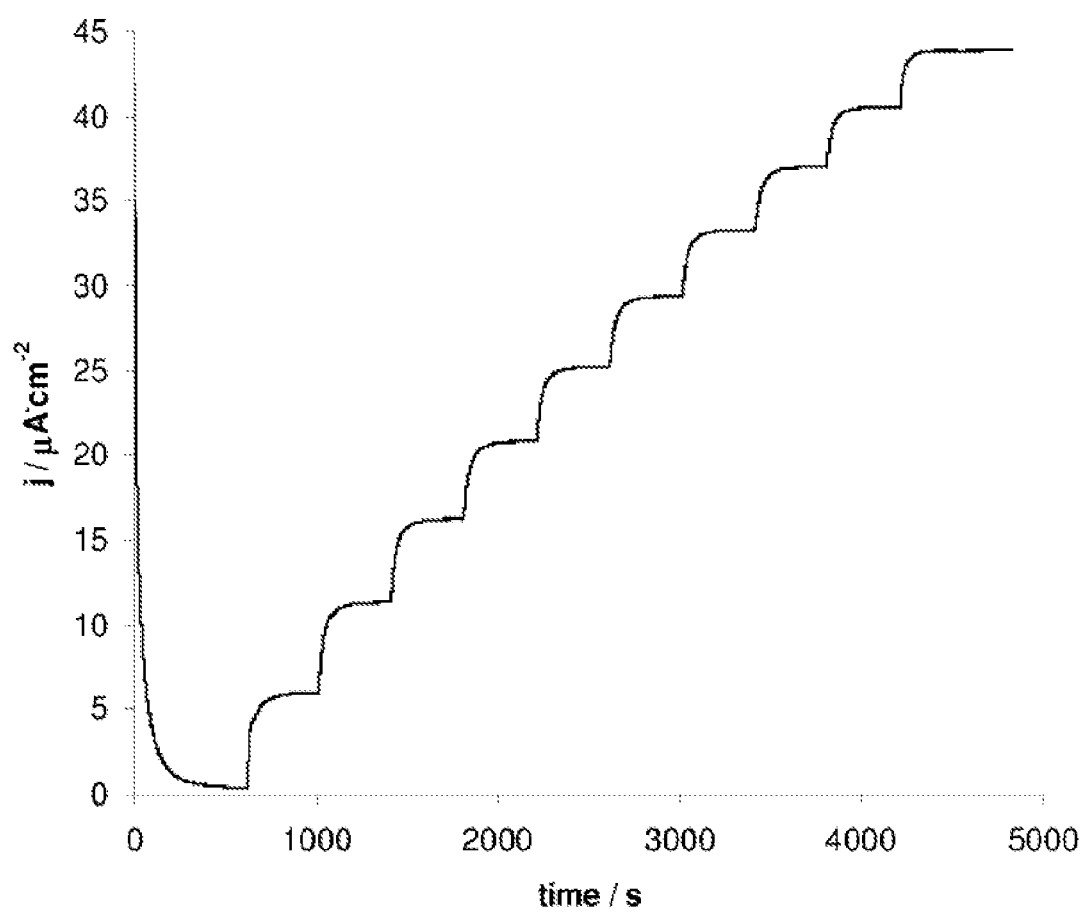
FIG. 23 shows rise-times of the current density upon increasing the glucose concentration by 1 mM increments. Electrode coated with an 0.1 mm thick β-Rib(Phyt)-7 wt. % VitEA-$H_2O$ LLC. Other conditions as in FIG. 15.

Slowing of the glucose-flux to the electrode necessarily increases the response-time to a change in the glucose concentration of the solution. FIG. 23 and Table 7 show the rise times of the glucose electrooxidation current when the glucose concentration is increased in 1 mM steps. As seen in the Table, the rise-time to 90% of the final current is about 2 min, fast enough for diabetes management.

TABLE 7

Glucose-electrooxidation current-rise times for anodes coated with a 0.1 mm thick film of β-Rib(Phyt)-7 wt. % VitEA-$H_2O$

| Glucose concentration change initial-final, mM | Time to 50% of the final current, s | Time to 90% of the final current. s | Time to 99% of the final current, s |
|---|---|---|---|
| 0-1 | 29 | 114 | 273 |
| 1-2 | 31 | 105 | 264 |
| 2-3 | 29 | 103 | 270 |
| 3-4 | 32 | 104 | 248 |
| 4-5 | 32 | 107 | 267 |
| 5-6 | 33 | 108 | 261 |
| 6-7 | 40 | 122 | 269 |
| 7-8 | 41 | 108 | 235 |
| 8-9 | 30 | 91 | 207 |
| 9-10 | 30 | 73 | 160 |

Example 16

Stability of the Sensitivity

In our probing for factors that affect the stability of the sensitivity of LLC-overcoated electrodes we operated these under more severe conditions than the conditions under which they would operate when implanted in a diabetic person. The electrodes were purposely overstressed by (a) operation at 50 mM glucose concentration, about 7 times the average in the subcutaneous interstitial fluid of a diabetic person and about 10 times the average in the subcutaneous fluid of a non-diabetic person; (b) operation in serum, where the protein concentration greatly exceeds that in the subcutaneous interstitial fluid; (c) maintaining an ~0.2 mM $O_2$-concentration by aeration of the electrolyte or serum, about twice that in the subcutaneous interstitial fluid; and (d) rotating the 5 mm electrodes at 100 rpm to enhance $O_2$-transport and to also enhance the shearing-off of material. Electrodes implanted in a diabetic person operate under quasi-stagnant conditions.

Through our operating at 50 mM glucose and rotation at 100 rpm, we maximally stressed both the glucose electrooxidation kinetics and the glucose $O_2$-oxidation kinetics. Any loss of rate of electron transfer from glucose to glucose oxidase, from glucose oxidase to the wire, and from the wire to the carbon-electrode is detected. Furthermore, because not the entire glucose influx is electrooxidized, even if the membrane provides the 2-30 mM linear glucose-response, the glucose oxidase molecules that are too far from the carbon surface to be effectively wired produce $H_2O_2$ which damages the bioelectrocatalyst. The local $H_2O_2$ concentration and thus the damage it causes are additionally raised by our enhancing the $O_2$-flux by rotating the electrode at 100 rpm. There would have been no such damage if the FAD-glucose oxidase were replaced by a glucose dehydrogenase of which $O_2$ is not a co-substrate such as the FAD-glucose dehydrogenase reported by Tsujimura et al., *Bioscience biotechnology and biochemistry* 70 (3): 654-659, 2006.

A degradation mechanism of some of the investigated LLCs was hydrolysis by serum lipases and formation of adducts with serum proteins. In a qualitative stability test, 20 mg samples of the cubic phases (a) MO/$H_2O$; (b) β-Rib(Phyt)/VitEA (7 wt. %)/$H_2O$; and (c) phytantriol/$H_2O$ were mixed with 1.5 mL of bovine serum at 37.5° C. The phytantriol/$H_2O$, (cubic to hexagonal phase transition temperature 42° C.) became promptly inhomogeneous; and the MO/$H_2O$ became turbid more rapidly than the β-Rib(Phyt)/VitEA (7 wt. %)/$H_2O$. After two days, nearly all the MO/$H_2O$ was consumed, i.e. reacted with serum and precipitated; about half of the phytantriol/$H_2O$ LLC remained intact and about half reacted with serum, apparently hydrolyzed by serum lipases; at the same time, most—about 60%—of the β-Rib(Phyt)/VitEA remained intact and isotropic. When wired glucose oxidase electrodes were over-coated with the hydrolysis-prone or protein-complexation-prone LLCs, their current densities increased as their mass-transport limiting layer was lost, then their current densities decrease as their bioelectrocatalyst is damaged or lost. When the preferred 0.1 mm thick β-Rib(Phyt)/VitEA (7 wt. %)/$H_2O$ membrane was applied to the wired glucose oxidase electrodes and the electrodes were rotated at 100 rpm for 48 h, the serum remained clear, and the LLC layer appeared to be intact except for yellowing and showing small superficial etch-marks. The LLC was, however, damaged: examination under the polarizing microscope showed birefringence and upon rinsing with water, the intact-appearing LLC came off and emulsified. The least hydrolysis and protein-complexation prone β-Rib(Phyt)/VitEA (7 wt. %)/$H_2O$-coated wired glucose oxidase anodes were damaged by $H_2O_2$, a by-product of wired glucose oxidase-catalyzed electrooxidation of glucose in air, in which a part of the electrons is diverted to glucose-oxidase catalyzed $O_2$-reduction. They are not damaged by this mechanism when the oxygen is not a co-substrate of the glucose oxidase or dehydrogenase used. For example, FAD-dependent glucose dehydrogenase of which oxygen is not a co-substrate has been reported by Tsujimura et al., *Bioscience biotechnology and biochemistry* 70 (3): 654-659, 2006 and can be used in the lyotropic liquid crystal comprising implanted glucose sensors.

In serum, where the protein concentration is much higher than in the subcutaneous interstitial fluid in which the electrode would operate, the current decayed initially rapidly most likely because of protein adsorption on the β-Rib(Phyt)-7 wt. % VitEA-$H_2O$, which plugged part of its superficial pores.

At 50 mM glucose concentration, the diverted fraction of electrons increases when the electrode is rotated, because the rate of $O_2$-reduction, the concentration of which is 250 times smaller than that of glucose is mass transport limited, while the concentration of glucose is not mass transport limited. We thus accelerated the damage by rotating the electrodes at 100 rpm in 50 mM glucose-containing aerated buffer or serum, with the electrodes poised at 0.15 V vs. Ag/AgCl. To confirm that the damage was $H_2O_2$-caused, we tested for dependence of the damage on the volume of the buffer solution in which the electrode rotated. When the damage is primarily $H_2O_2$-caused, the decay of the current density accelerates with the inverse of the volume of the buffer, i.e. with the evolved $H_2O_2$ concentration. We found such acceleration irrespective of the electrodes being or not being over-coated with the 0.1 mm thick β-Rib(Phyt)-7 wt. % VitEA-$H_2O$. The half lives of the over-coated electrodes averaged 9 h when the buffer volume was 50 mL and 13 h when the volume was 800 mL. Without the over-coatings, the half lives in 800 mL buffer-volume averaged 15 h, consistent with slower leaching and higher local $H_2O_2$ concentration when the electrodes were over-coated.

Figure 24:
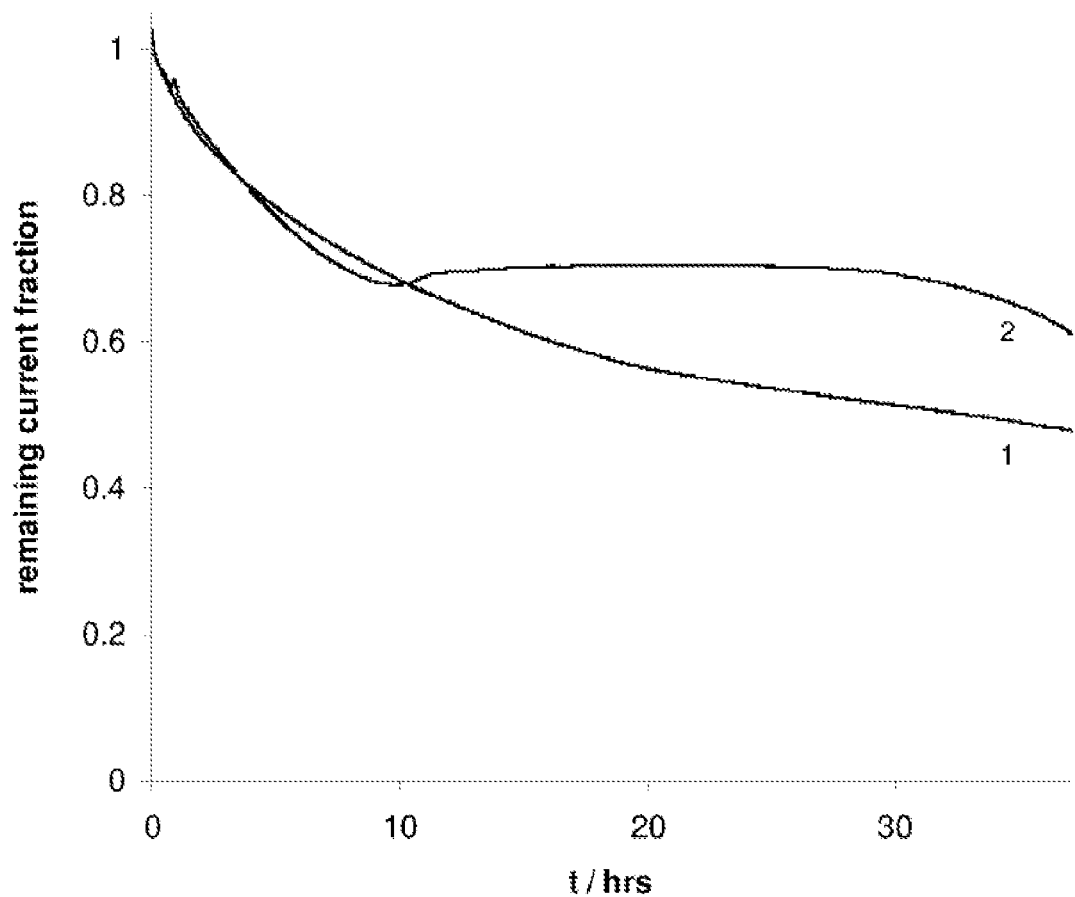
FIG. 24 shows the time dependence of the residual fraction of the current of 5 mm diameter wired glucose oxidase anodes in 50 mL, of 50 mM glucose, antibiotic-antimycotic—stabilized aerated fetal calf serum at 37.5° C. 100 rpm; 0.15 V vs. Ag/AgCl. The wired glucose oxidase layer on the electrodes was overcoated with albumin (72.9 wt %)-catalase (25.9 wt %) crosslinked with glutaraldehyde (1.2 wt %). (1) without; (2) with a 0.1 mm thick β-Rib (Phyt)/7 wt. % VitEA/$H_2O$ overcoating.

In serum, a glutaraldehyde-crosslinked albumin/catalase coating of the wired glucose oxidase layer considerably improved the stability after the initial rapid loss, attributed to protein-adsorption. (FIG. 24). Not only were the half-lives of electrodes both without LLC-overcoating and with LLCs overcoating increased respectively to 32 hr and 36 hr, but in the LLC-coated electrode we observed the hoped for stable operation plateau between t=10 h and t=30 h, in which the glucose electrooxidation current was constant within ±5%. (FIG. 24) Considering that the damage is primarily $H_2O_2$-caused, and considering that the $O_2$-flux to electrodes in the stagnant subcutaneous fluid is smaller than that to electrodes rotating at 100 rpm in aerated serum, we consider it likely that the sensitivity of the subcutaneously implanted β-Rib(Phyt)-7 wt. % VitEA-$H_2O$ wired glucose oxidase electrodes will be constant for a longer period, possibly for about week The bicontinuous β-Rib(Phyt)-based lyotropic liquid crystalline cubic phase is stabilized by hydrophobic bonds between the long hydrocarbon chains and by the hydrogen-bonds between the ribose head-groups of its amphiphile. The thermodynamically stable phase has a Pn3m structure and remains stable at high hydration. The temperature range through which it is stable can be adjusted by adding vitamin E acetate. β-Rib(Phyt)/VitEA (7 wt. %)/$H_2O$ is cubic and stable through the 20° C.-90° C. range and is mechanically so strong that it is not sheared off the edge of a 5 mm diameter electrode rotating at 4000 rpm, on which the shear stress is ~1 N m$^{-2}$. β-Rib(Phyt)/VitEA (7 wt. %) also retains its shape upon dehydration-hydration. After a 0.1 mm thick glucose-transport limiting layer is coated by doctor-blading on the glucose electrooxidation catalyst, the current increases linearly with the glucose concentration through the 2-30 mM range relevant to diabetes-management. The anode reaches 90% of its ultimate current in less than 2 min. The activation energy for glucose transport through the liquid crystalline layer is 15.6 kJ/mol. Because of the small activation energy, the current is less temperature-dependent than that of polymer-coated anodes. The main factors affecting the stability of the sensitivity of the LLC-over-coated electrodes are protein-concentration and $H_2O_2$-concentration, which is reduced by a catalase-containing layer on the glucose electrooxidation catalyst.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of monitoring the concentration of an analyte, the method comprising:
   positioning at least a portion of an electrochemical sensor beneath the surface of the skin of a subject, wherein the electrochemical sensor comprises:

a working electrode comprising an analyte-responsive enzyme in contact with the electrode and a non-crosslinked cubic phase lyotropic liquid crystal membrane disposed on top of the analyte-responsive enzyme; and a counter electrode or reference electrode or a counter/reference electrode in communication with the working electrode;

applying a potential between the working electrode and the counter electrode to electrolyze the analyte and generate hydrogen peroxide;

measuring the generated hydrogen peroxide; and determining the concentration of the analyte from the measured hydrogen peroxide.

2. The method according to claim 1, wherein the analyte-responsive enzyme is a glucose-responsive enzyme.

3. The method according to claim 2, wherein the glucose-responsive enzyme is a glucose oxidase.

4. The method according to claim 1, wherein the cubic phase lyotropic liquid crystal membrane forms a diamond type cubic phase.

5. The method according to claim 1, wherein the cubic phase lyotropic liquid crystal membrane withstands a shear stress of about 1 N m$^{-2}$.

6. The method according to claim 1, wherein sensor has a decrease dependence of current on temperature when the current is controlled by the permeation of the analyte through the cubic phase lyotropic liquid crystal membrane.

7. The method according to claim 1, wherein the cubic phase lyotropic liquid crystal is substantially non-hydrolyzable in the presence of a lipase.

8. The method according to claim 7, wherein the cubic phase lyotropic liquid crystal comprises a compound of the formula:

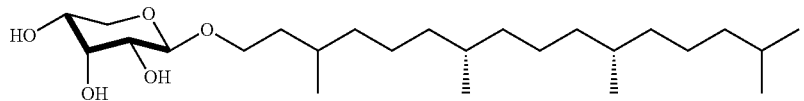

9. The method according to claim 8, wherein the cubic phase lyotropic liquid crystal comprises Vitamin E acetate.

10. The method according to claim 1, wherein the sensor comprises an anticlotting agent.

11. The method according to claim 10, wherein the anticlotting agent is heparin.

12. The method according to claim 10, wherein the cubic phase lyotropic liquid crystal comprises the anticlotting agent.

13. The method according to claim 1, wherein the cubic phase lyotropic liquid crystal membrane is adapted to limit the flux of glucose or lactate thereacross.

14. The method according to claim 1, wherein the analyte is glucose.

* * * * *